US011155605B2

(12) United States Patent
Nussenzweig et al.

(10) Patent No.: US 11,155,605 B2
(45) Date of Patent: Oct. 26, 2021

(54) NUCLEIC ACIDS ENCODING BROADLY NEUTRALIZING GLYCAN-DEPENDENT 8ANC195 ANTIBODY VARIANTS THAT BIND TO AN EPITOPE SPANNING BOTH HIV-1 ENV SUBUNITS

(71) Applicants: The Rockefeller University, New York, NY (US); California Institute of Technology, Pasadena, CA (US)

(72) Inventors: Michel Nussenzweig, New York, NY (US); Pamela J. Bjorkman, La Canada Flintridge, CA (US); Louise Scharf, Porter Ranch, CA (US); Johannes Scheid, New York, NY (US)

(73) Assignees: THE ROCKEFELLER UNIVERSITY, New York, NY (US); CALIFORNIA INSTITUTE OF TECHNOLOGY, Pasadena, CA (US)

(*) Notice: Subject to any disclaimer, the term of this patent is extended or adjusted under 35 U.S.C. 154(b) by 0 days.

(21) Appl. No.: 16/578,833

(22) Filed: Sep. 23, 2019

(65) Prior Publication Data
US 2020/0140528 A1    May 7, 2020

Related U.S. Application Data

(63) Continuation of application No. 15/115,547, filed as application No. PCT/US2015/013924 on Jan. 30, 2015, now Pat. No. 10,421,803.

(60) Provisional application No. 61/934,359, filed on Jan. 31, 2014.

(51) Int. Cl.
| | | |
|---|---|---|
| *C07K 16/10* | (2006.01) | |
| *A61K 39/42* | (2006.01) | |
| *A61P 31/18* | (2006.01) | |
| *A61K 39/21* | (2006.01) | |
| *C07K 14/005* | (2006.01) | |
| *G01N 33/569* | (2006.01) | |

(52) U.S. Cl.
CPC .......... *C07K 16/1063* (2013.01); *A61K 39/21* (2013.01); *A61K 39/42* (2013.01); *A61P 31/18* (2018.01); *C07K 14/005* (2013.01); *G01N 33/56988* (2013.01); *C07K 2299/00* (2013.01); *C07K 2317/21* (2013.01); *C07K 2317/24* (2013.01); *C07K 2317/55* (2013.01); *C07K 2317/76* (2013.01); *C07K 2317/92* (2013.01); *C12N 2740/16111* (2013.01); *G01N 2333/162* (2013.01)

(58) Field of Classification Search
CPC ................ C07K 16/1063; A61K 39/42; C12N 2740/16111
See application file for complete search history.

(56) References Cited

U.S. PATENT DOCUMENTS

2013/0251726 A1    9/2013    Mascola et al.

FOREIGN PATENT DOCUMENTS

| WO | 1993019785 A1 | 10/1993 |
| WO | 2012158948 A1 | 11/2012 |

OTHER PUBLICATIONS

West et al., "Computational analysis of anti-HIV-1 antibody neutralization panel data to identify potential functional epitope residues," PNAS (Jun. 25, 2013); 110(26): 10598-10603.
West Jr. et al., "Single-Chain Fv-Based Anti-HIV Proteins: Potential and Limitations," Journal of Virology (Jan. 2012); 86(1): 195-202.
Abela et al., "Cell-Cell Transmission Enables HIV-1 to Evade Inhibition by Potent CD4bs Directed Antibodies," PLoS Pathogens (Apr. 2012); 8(4): 1-21.
Kwong et al., "Broadly neutralizing antibodies and the search for an HIV-1 vaccine: the end of the beginning," Nat. Rev. Immunol.(Sep. 2013); 13: 693-701.
Gong et al., "Candidate Antibody-Based Therapeutics Against HIV-1," Biodrugs (2012); 26(3)): 143-162.
Caskey et al., "Broadly neutralizing anti-HIV-1 monoclonal antibodies in the clinic", Nature Medicine, vol. 25, 2019, pp. 547-553.
Dashti et al., "Broadly Neutralizing Antibodies against HIV: Back to Blood", Trends in Molecular Medicine, vol. 25, No. 3, 2019.
McCoy, "The expanding array of HIV broadly neutralizing antibodies", Retrovirology, 2018, 15:70.
Parsons et al., "Importance of Fc-mediated functions of anti-HIV-1 broadly neutralizing antibodies", Retrovirology, 2018, 15:58.
Possas et al., "HIV cure: global overview of bNAbs' patents and related scientific publications", Expert Opinion on Therapeutic Patents, 2018, vol. 28, No. 7, pp. 551-560.
Sok et al., "Recent progress in broadly neutralizing antibodies to HIV", Nature Immunology, 2018, vol. 19, pp. 1179-1188.
Liu et al., "Broadly neutralizing antibodies for HIV-1: effecacies, challenges and opportunities", Emerging Microbes & Infections, 2020, vol. 9.
Mahomed et al., "Clinical Trials of Broadly Neutralizing Monoclonal Antibodies for Human Immunodeficiency Virus Prevention: A Review", The Journal of Infectious Diseases, 2021, 13;223(3), pp. 370-380.

*Primary Examiner* — Jeffrey S Parkin
(74) *Attorney, Agent, or Firm* — Fox Rothschild LLP

(57) ABSTRACT

The present invention relates to broadly neutralizing anti-HIV-1 antibodies and isolated antigens. Also disclosed are related methods and compositions.

11 Claims, 23 Drawing Sheets
Specification includes a Sequence Listing.

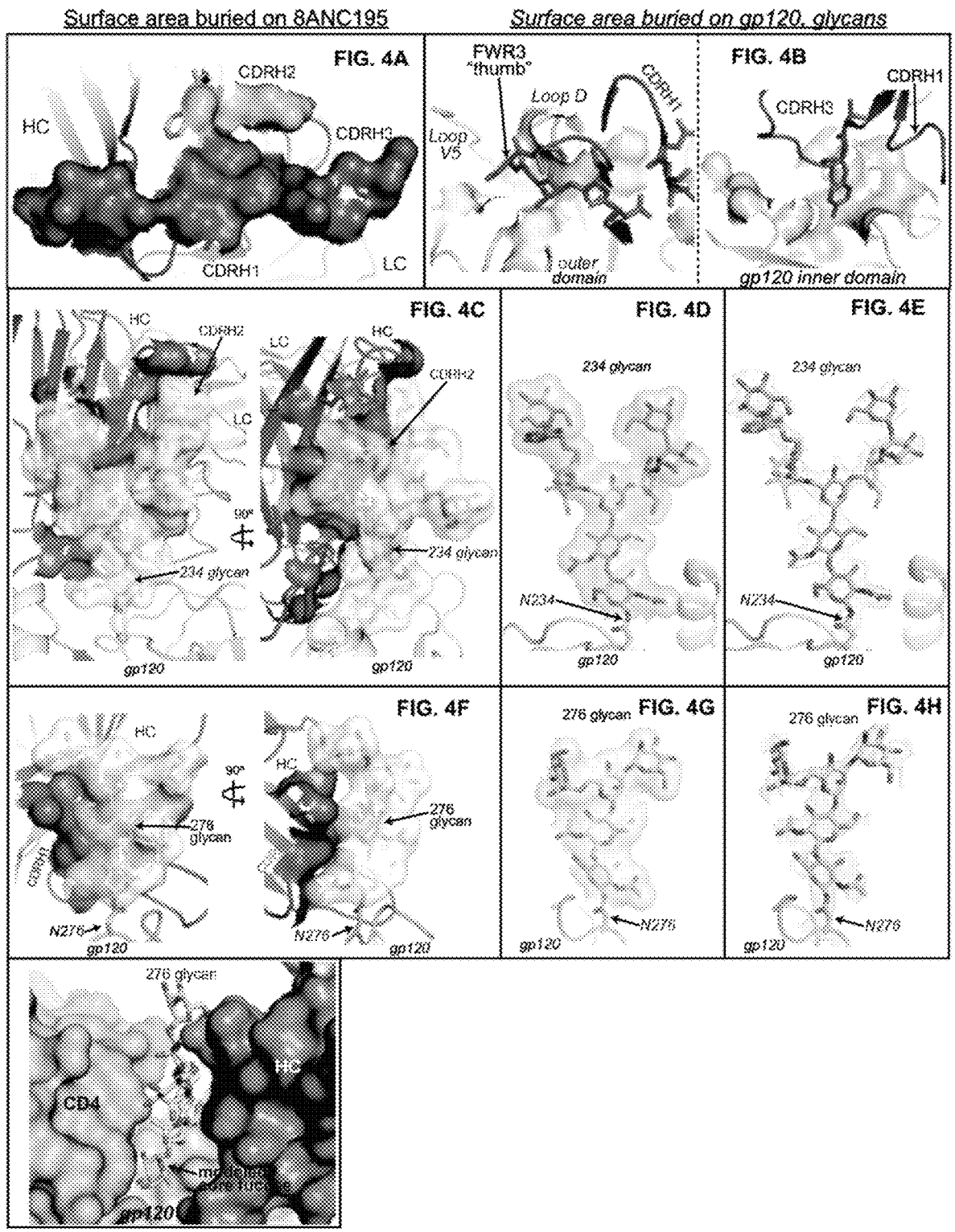

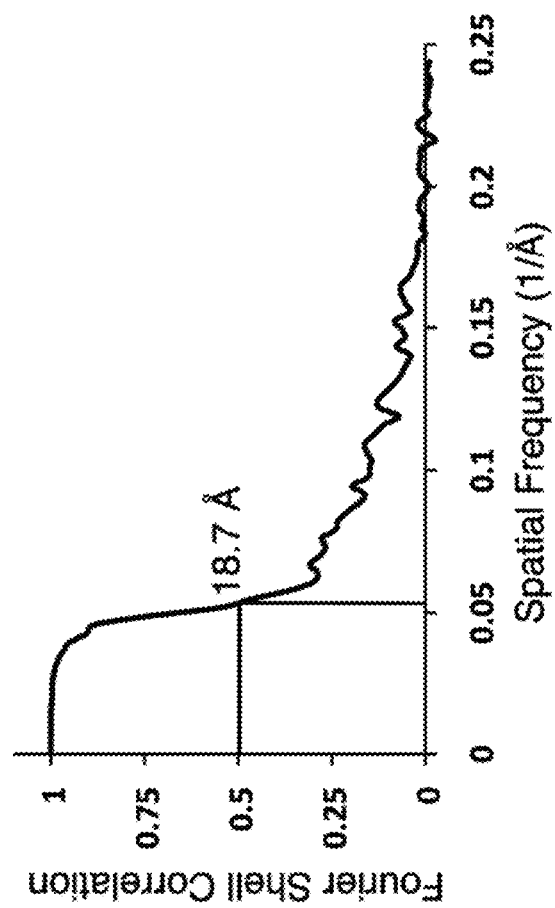
FIG. 6C
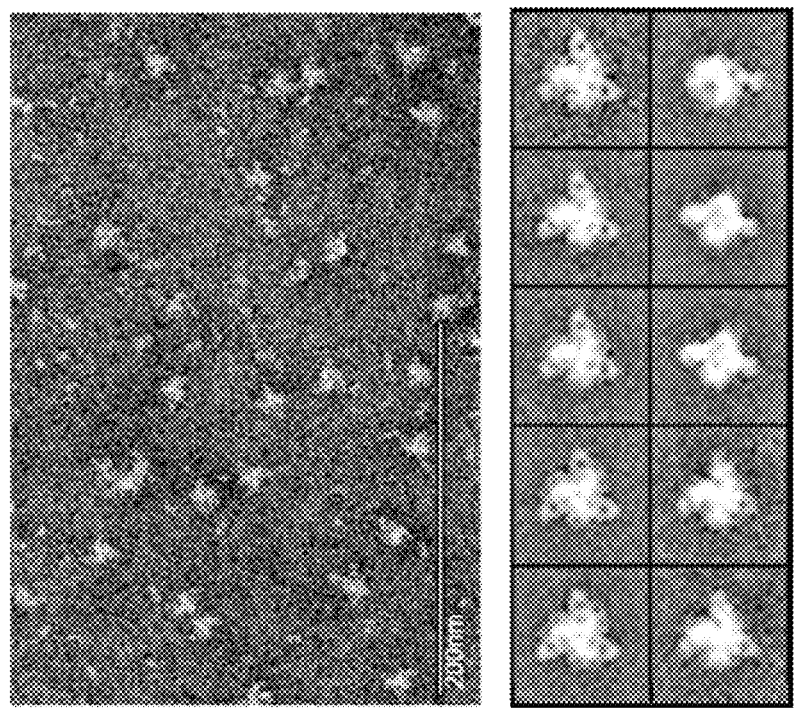
FIG. 6A
FIG. 6B

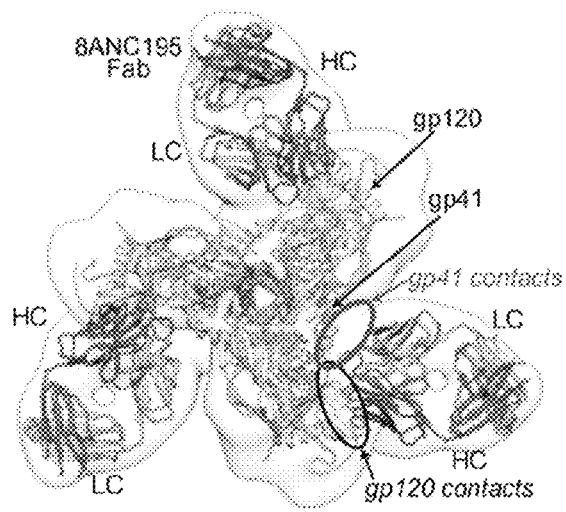
FIG. 8A
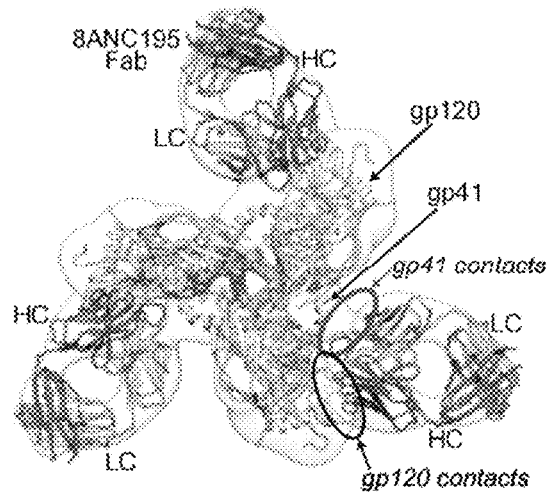
FIG. 8B
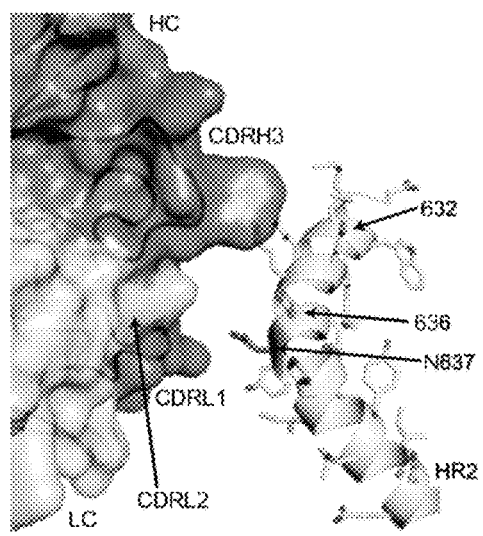
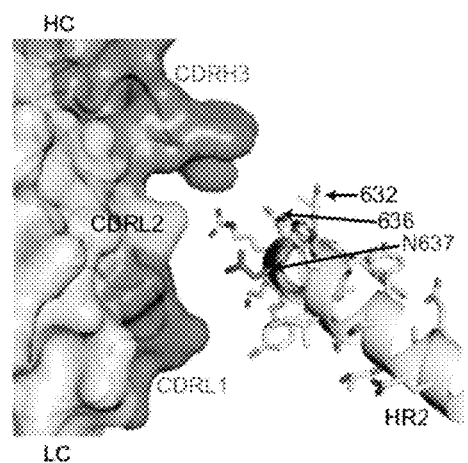
FIG. 8C
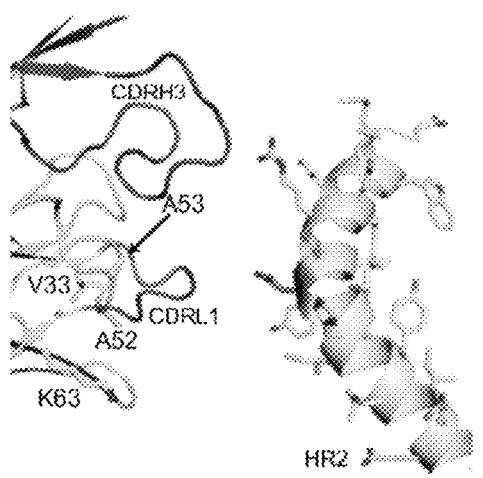
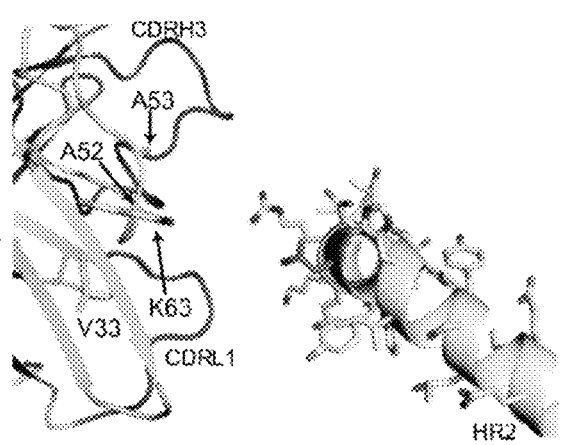
FIG. 8D

FIG. 10A

| HC | FWR1 | CDR1 | FWR2 | CDR2 | FWR3 | CDR3 |
|---|---|---|---|---|---|---|
| | 10 | 20 | 30 | 40 | 50 | 60 | 70 | 80 | 90 | 100 | 110 | 120 |
| VH1-69GL | QVQLVQSGAEVKKPGSSVKVSCKASG | GTFSSYAIS | WVRQAPGQGLEWMG | GIIPIFGTANYAQKFQ | GRVTITADE | STSTAYMELSSLRSEDTAVYYCAR | |
| 8ANC2080 | QLLVQSGEVKKPGSSVKVSCKAG | TF | YA | WVRQAPGQ | LE | G | A | F | GRV | TA | E | TAVY | C | TSTYDKWSGLHHDGVMAFSS |
| 8ANC3035 | QLLVQSGEVKKPGSSVKVSCKAG | TF | YA | WVRQAPGQ | LE | G | A | F | GRV | TA | E | TAVY | C | TSTYDKWSGLHHDGVMAFSS |
| 8ANC3369 | QLLVQSGEVKKPGSSVKVSCKAG | TF | YA | WVRQAPGQ | LE | G | A | F | GRV | TA | E | TAVY | C | TSTYDKWSGLHHDGVMAFSS |
| 8ANC3625 | QLLVQSGEVKKPGSSVKVSCKAG | TF | YA | WVRQAPGQ | LE | G | A | F | GRV | TA | E | TAVY | C | TSTYDQRSGLHHDGVMAFSS |
| 8ANC3040 | QLLVQSGEVKKPGSSVKVSCKAG | TF | YA | WVRQAPGQ | LE | G | A | F | GRV | TA | E | TAVY | C | TSTYDKWSGLHHDGVMAFSS |
| 8ANC3288 | QLLVQSGEVKKPGSSVKVSCKAG | TF | YA | WVRQAPGQ | LE | G | A | F | GRV | TA | E | TAVY | C | TSTYDKWSGLHHDGVMAFSS |
| 8ANC3630 | QLLVQSGEVKKPGSSVKVSCKAG | TF | YA | WVRQAPGQ | LE | G | A | F | GRV | TA | E | TAVY | C | TSTYDKWSGLHHDGVMAFSS |
| 8ANC3430 | QLLVQSGEVKKPGSSVKVSCKAG | TF | YA | WVRQAPGQ | LE | G | A | F | GRV | TA | E | TAVY | C | TSTYDKWSGLHHDGVMAFSS |
| 8ANC3484 | QLLVQSGEVKKPGSSVKVSCKAG | TF | YA | WVRQAPGQ | LE | G | A | F | GRV | TA | E | TAVY | C | TSTYDKWSGLHHDGVMAFSS |
| 8ANC3044 | QLLVQSGEVKRPGSSVKVSCKAG | TF | YA | WVRQAPGQ | LE | G | A | F | GRV | TA | E | TAVY | C | TSTYDKWSGLHHDGVMAFSS |
| 8ANC3509 | QLLVQSGEVKKPGSSVKVSCKAG | TF | YA | WVRQAPGQ | LE | G | A | F | GRV | TA | E | TAVY | C | TSTYDKWSGLHHDGVMAFSS |

FIG. 10B

| LC | FWR1 | CDR1 | FWR2 | CDR2 | FWR3 | CDR3 |
|---|---|---|---|---|---|---|
| | 10 | 20 | 30 | 40 | 50 | 60 | 70 | 80 | 90 | 100 |
| VK1-5GL | DIQMTQSPSTLSASVGDRVTITC | RASQSISS | WLAWYQQKPGKAPKLLIY | DASSLES | GVPSRFSGSGSGTEFTLTISSLQPDDFATYYC | QQYNSYS | |
| 8ANC2080 | DIQMTQSPSTLSASVGDRVTITC | RASQSI | WYQQ | PGKAP | LLIY | S | GVPSRFSGS | GT | FTLTI | LQ | DF | YYC | QQY | LYGTFG |
| 8ANC3035 | DIQMTQSPSTLSASVGDRVTITC | RASQSI | AWYQQ | PGKAP | LLIY | S | GVPSRFSGS | GT | FTLTI | LQ | DF | YYC | QQY | LYGTFG |
| 8ANC3369 | DIQMTQSPSTLSASVGDRVTITC | RASQSI | AWYQQ | PGKAP | LLIY | S | GVPSRFSGS | GT | FTLTI | LQ | DF | YYC | QQY | LYGTFG |
| 8ANC3625 | DIQMTQSPSTLSASVGDRVTITC | RASQSI | AWYQQ | PGKAP | LLIY | S | GVPSRFSGS | GT | FTLTI | LQ | DF | YYC | QQY | LYGTFG |
| 8ANC3040 | DIQMTQSPSTLSASVGDRVTITC | RASQSI | AWYQQ | PGKAP | LLIY | S | GVPSRFSGS | GT | FTLTI | LQ | DF | YYC | QQY | LYGTFG |
| 8ANC3288 | DIQMTQSPSTLSASVGDRVTITC | RASQSI | WLAWYQQ | PGKAP | LLIY | S | GVPSRFSGS | GT | FTLTI | LQ | DF | YYC | QQY | LYGTFG |
| 8ANC3630 | DIQMTQSPSTLSASVGDRVTITC | RASQSI | WLAWYQQ | PGKAP | LLIY | S | GVPSRFSGS | GT | FTLTI | LQ | DF | YYC | QQY | LYGTFG |
| 8ANC3430 | DIQMTQSPSTLSASVGDRVTITC | RASQSI | AWYQQ | PGKAP | LLIY | S | GVPSRFSGS | GT | FTLTI | LQ | DF | YYC | QQY | LYGTFG |
| 8ANC3484 | DIQMTQSPSTLSASVGDRVTITC | RASQSI | WLAWYQQ | PGKAP | LLIY | S | GVPSRFSGS | GT | FTLTI | LQ | DF | YYC | QQY | LYGTFG |
| 8ANC3044 | DIQMTQSPSTLSASVGDRVTITC | RASQSI | AWYQQ | PGKAP | LLIY | S | GVPSRFSGS | GT | FTLTI | LQ | DF | YYC | QQY | LYGTFG |
| 8ANC3509 | DIQMTQSPSTLSASVGDRVTITC | RASQSI | WLAWYQQ | PGKAP | LLIY | S | GVPSRFSGS | GT | FTLTI | LQ | DF | YYC | QQY | LYGTFG |

FIG. 11A

~ 800x10⁶ PBMCs → 1.1x10⁶ Memory B Cells

[Flow cytometry plot: CD19 vs IgG] → Bulk Sort Without Antigen

FIG. 11B

Amplification with Clone Specific Primers

Heavy Chain

```
8ANC195...CAGGTGCCCAGTGCCAGATCACACCTCGTGCAA...
    Prim1 5' GGTGTACATTCCAGATACACCTTGTACCA 3'
    Prim2 5' CAGGTGTCCAGTCTCAGATACA 3'

8ANC195...AACCCTCATCTCCGTCTCCGGCC...
    Prim1 3' AACCCTCATCTCCGTCTCCGC 5'
```

FWR1 →
                            J-Gene →

128 sequences, 100% clonal relatives of 8ANC195

Light Chain

```
8ANC195...GACATCCAGATGACCCAGTCTCCTTCCACCCTG&CTGCATCTATAGGT...
    Prim1 5' GACATCCAGATGACCCAGTCTCCACCCTGCATCTATAGGT 3'
    Prim2 5' GACATCCAGATGACCCAGTCTCCTCCACCCTGTCATCT 3'

8ANC195...CCAGGGACTTCGGCCAAGGGACTAAAGTTGAGGTGAAAC...
    Prim1 3' AAGGGACTAAAGTTGAGCCGAAAC 5'
    Prim2 3' GACCTTCGGCCAAGGGACTAAAGTTGAGGTGAAAC 5'
```

FWR1 →
                            J-Gene →

100 sequences, 100% clonal relatives of 8ANC195

FIG. 11C

[Phylogenetic tree - Heavy Chain, scale 0.05]

[Phylogenetic tree - Light Chain, scale 0.0060]

| IC₅₀ Virus | y52_HCκ5_LC | 8ANC195 |
|---|---|---|
| REJO4541.67 | 0.035 | 0.08 |
| PVO.4 | 0.018 | 0.52 |
| YU2.DG | 0.065 | 0.79 |
| 3415.v1.c1 | 0.120 | 2.404 |
| 3365.v2.c20 | >50 | >30 |
| ZM53M.PB12 | 3.134 | 9.626 |
| ZM109F.PB4 | >50 | >30 |
| 3016.v5.c45 | 0.017 | 0.195 |
| 231965.c1 | 0.094 | 0.514 |
| X1254_c3 | 0.504 | 1.524 |
| 251-18 | 0.048 | 0.284 |
| R1166.c1 | 0.319 | 0.986 |
| H086.8 | 0.175 | 0.095 |
| Du172.17 | 0.841 | 10.797 |
| 250-4 | >50 | >50 |

FIG. 16A
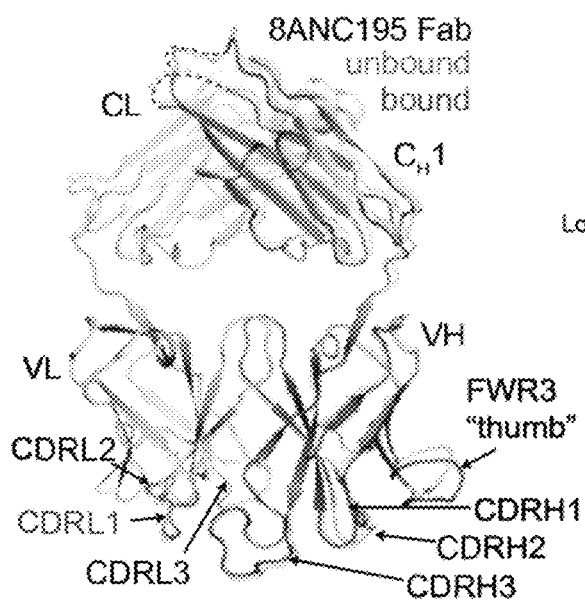
FIG. 16C
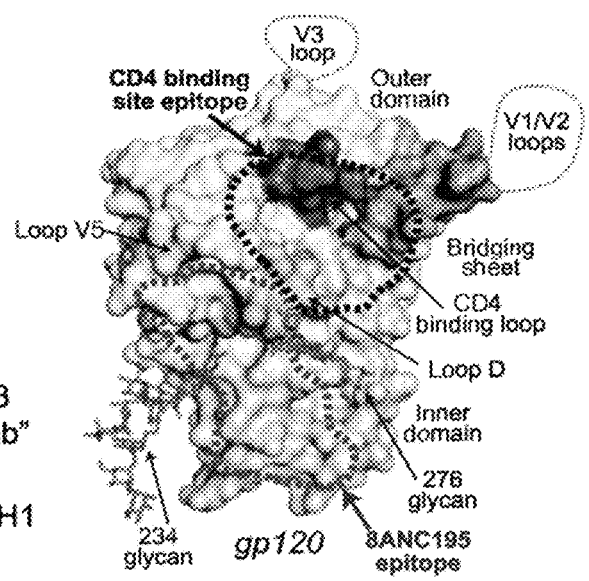
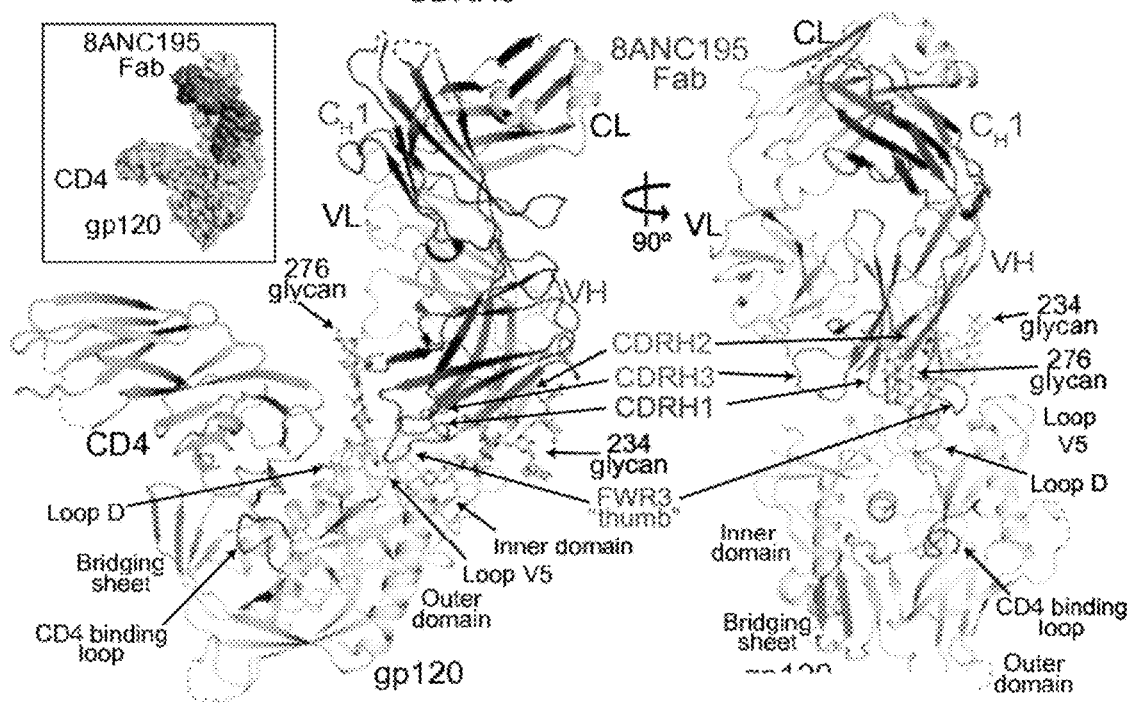
FIG. 16B

FIG. 17A
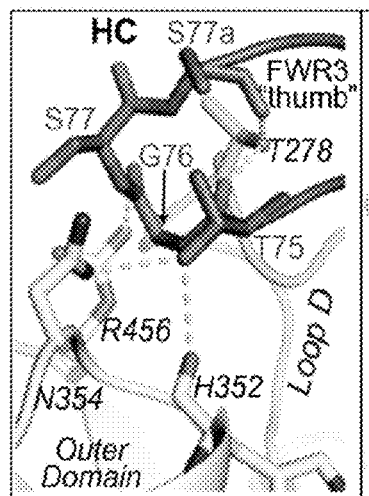
FIG. 17B
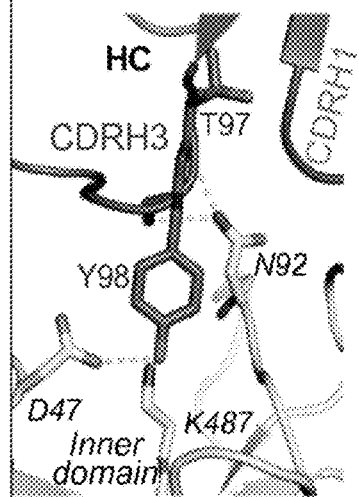
FIG. 17C
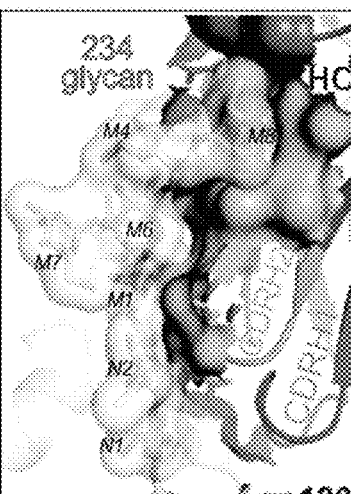
FIG. 17D
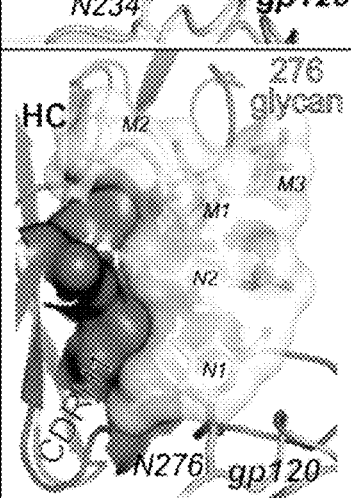
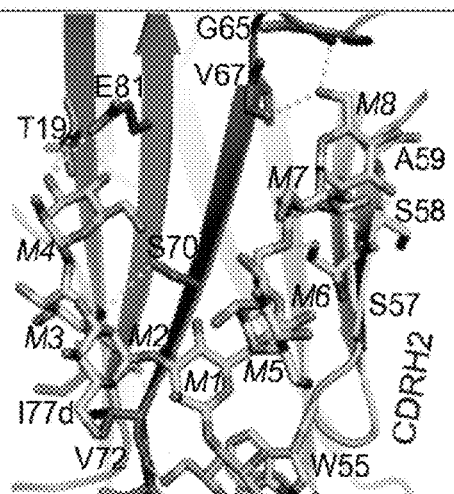
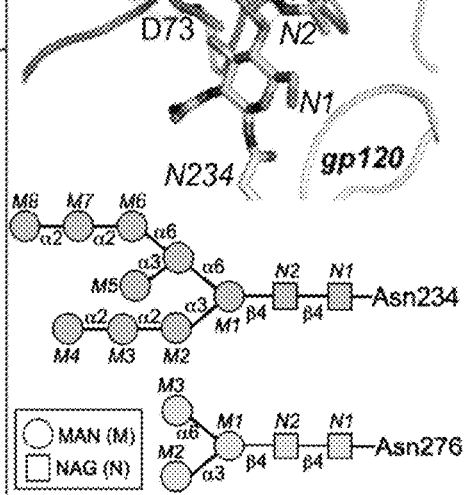
FIG. 17E

FIG. 18A
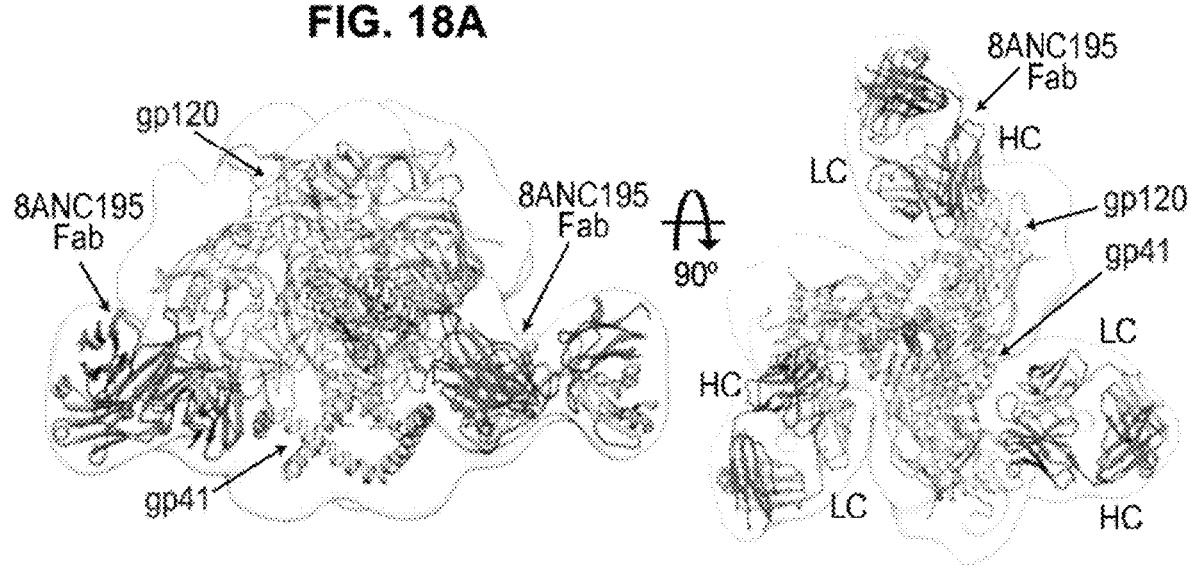
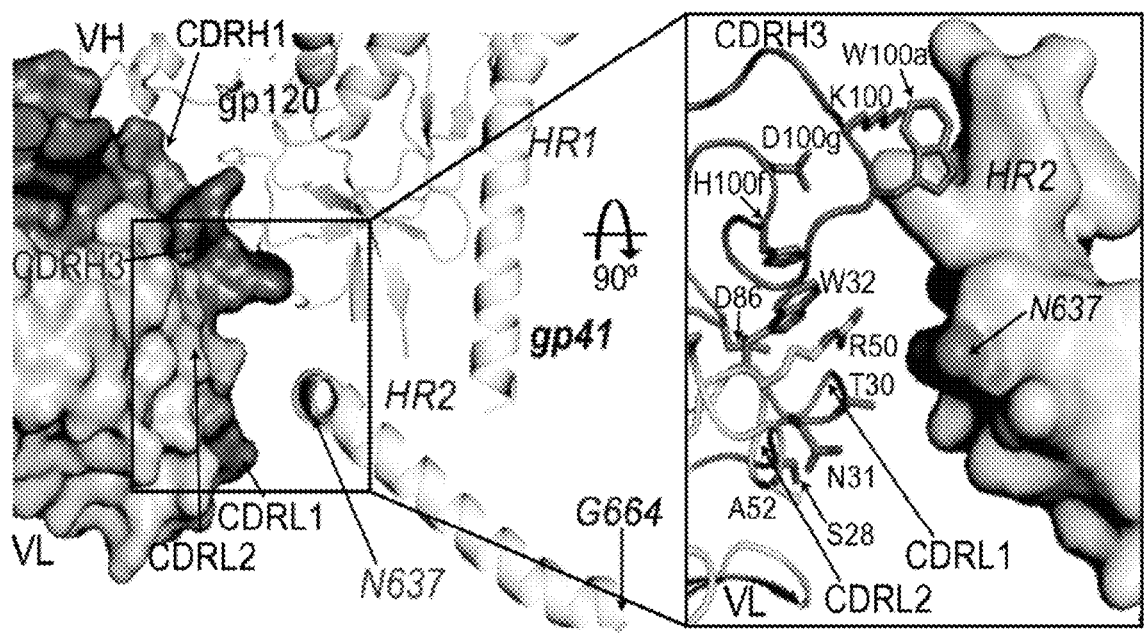
FIG. 18B

FIG. 19A
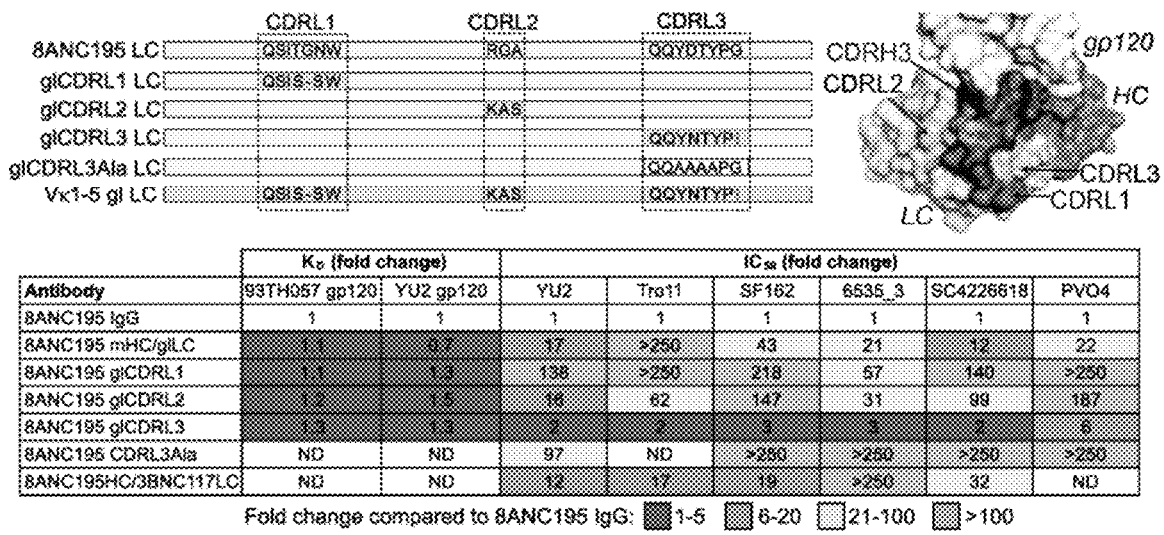
FIG. 19B
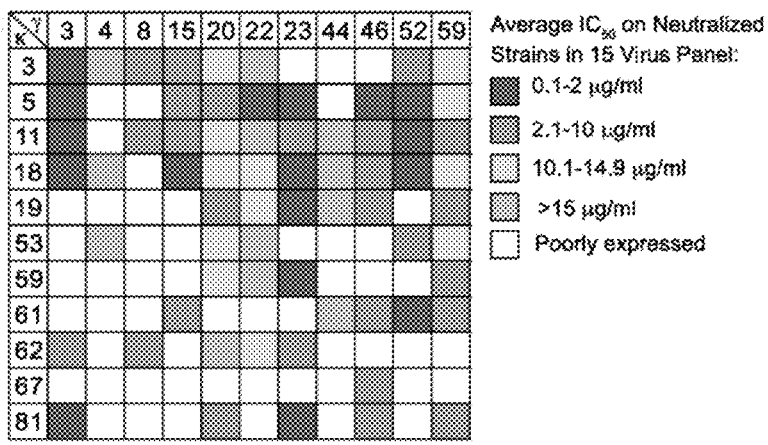
FIG. 19C

NUCLEIC ACIDS ENCODING BROADLY NEUTRALIZING GLYCAN-DEPENDENT 8ANC195 ANTIBODY VARIANTS THAT BIND TO AN EPITOPE SPANNING BOTH HIV-1 ENV SUBUNITS

CROSS-REFERENCE TO RELATED APPLICATIONS

This application is a Continuation of U.S. patent application Ser. No. 15/115,547, filed Jul. 29, 2016, now U.S. Pat. No. 10,421,803, which is the U.S. National Phase of International Patent Application No. PCT/US2015/013924, filed Jan. 30, 2015, which claims priority to U.S. Provisional Application No. 61/934,359 filed Jan. 31, 2014, the contents of which are incorporated herein by reference.

STATEMENT REGARDING FEDERALLY SPONSORED RESEARCH OR DEVELOPMENT

The invention disclosed herein was made, at least in part, with Government support under Grant Nos. HIVRAD P01 AI100148 and 1UM1 AI100663-01 from the National Institutes of Health. Accordingly, the U.S. Government has certain rights in this invention.

BACKGROUND OF THE INVENTION

The only target of neutralizing anti-HIV-1 antibodies is the envelope (Env) spike, a heterotrimer of gp120 and gp41 subunits. Single cell-based antibody cloning techniques have recently uncovered a large number of antibodies that can potently neutralize highly diverse HIV-1 variants by targeting Env (Klein et al., *Science* 341, 1199 (2013)). When transferred passively, broadly neutralizing antibodies (bNAbs) can prevent infection by HIV-1 or SHIV in humanized mice and macaques, respectively. Moreover, combinations of bNAbs can also suppress established HIV-1 and SHIV infections (Klein et al., *Nature* 492, 118 (2012); Barouch et al., *Nature* 503, 224 (2013); Shingai et al., *Nature* 503, 277 (2013)).

Most of the bNAbs characterized to date target one of four major sites of vulnerability on HIV-1 Env: on gp120, the CD4 binding site, the V2 loop, and the base of the V3 loop, and on gp41, the membrane proximal region (Klein et al., *Science* 341, 1199 (2013); Burton et al., *Science* 337, 183 (2012); Mascola et al., *Immunological Reviews* 254, 225 (2013)). 8ANC195 is among a small group of bNAbs that does not appear to target any of these sites. Although only two of the B cells originally isolated from the 8ANC195 donor, an HIV-1 elite controller, belonged to the 8ANC195 clone, the antibodies produced by this clone complemented the neutralizing activity of antibodies produced by a more expanded B cell clone that targeted the CD4 binding site (Scheid et al., *Science* 333, 1633 (2011)).

8ANC195 is classified as a bNAb because it neutralized 66% of viruses in a diverse viral panel (Scheid et al., *Science* 333, 1633 (2011)). Like other anti-HIV-1 bNAbs, 8ANC195 is highly somatically mutated, including insertions and deletions in the complementarity determining regions (CDRs) and framework regions (FWRs) of its heavy chain (HC) and light chain (LC). Although initial efforts to map the 8ANC195 epitope were unsuccessful (Ibid.) computational analyses of neutralization data predicted that intact potential N-linked glycosylation sites (PNGSs) at positions $234_{gp120}$ and $276_{gp120}$ were essential for its activity. These predictions were confirmed by evaluating the neutralization potency of 8ANC195 against mutant HIV-1 strains in vitro and in vivo (West, Jr. et al., *Proceedings of the National Academy of Sciences of the United States of America* 110, 10598 (2013); Chuang et al., *Journal of Virology* 87, 10047 (2013)). However, the precise 8ANC195 epitope on HIV-1 Env has heretofore remained elusive.

SUMMARY OF INVENTION

This invention relates, in part, to the isolation of broadly-neutralizing antibodies (bNAbs) directed at an epitope on the HIV-1 envelope spike that spans the gp120 and gp41 subunits.

In one embodiment, the antibody comprises a heavy chain having one of the following amino acid sequences:

```
                                   (g52; SEQ ID NO: 1)
QIHLVQSGTEVKKPGSSVTVSCKAYGVNTFGLYAVNWVRQAPGQSLEYIG

QIWRWKSSASHHFRGRVLISAVDLTGSSPPISSLEIKNLTSDDTAVYFCT

TTSTYDRWSGLHHDGVMAFSSWGQGTLISVSAASTKG;

(g23; SEQ ID NO: 2)
QIHLVQSGTEVKKPGSSVTVSCKAYGVNTFGLYAVNWVRQAPGQSLEYIG

QIWRWKSSASHHFRGRVIISAVDLTGSSPPISSLEIKNLTSDDTAVYFCT

TTSTSDYWSGLHHDGVMAFSSWGQGTLISVSAASTKG;

(g8; SEQ ID NO: 3)
QIHLVQSGTGVKKPGSSVTVSCKAYGVNTFGLYAVNWVRQAPGQGLEYIG

QIWRWKSSASHHFRGRVLISAVDLTGSSPPITSLEIKNVTSDDTAVYFCT

TTSTYDKWSGLYHDGVMAFSSWGQGTLISVSAASTKG;

(g20; SEQ ID NO: 4)
QIHLVQSGTEVKKPGSSVAVSCKAYGVNTFGLYAVNWVRQAPGQSLEYIG

QIWRWKSSASHDFRGRVIISAVDLTGSSPPISSLEIKNLTSDDTAVYFCT

ATSTPDYWSGLHHDGVMAFSSWGQGTLISVSAASTKG;

(g59; SEQ ID NO: 5)
QIHLVQSGTEVKKPGSSVTVSCKAYGVNTFGLYAVNWVRQAPGQGLEYIG

QIWRWKSSASHHFRGRVLISAVDLTGSSPPISSLEIKNVTSDDTAVYFCT

TTSTYDEWSDLHHDGVMAFSSWGQGTLISVSAASTKG;

(g62; SEQ ID NO: 6)
QIHLVQSGTEVKKPGSSVTVSCKAYGVNTFGLYAVNWVRQAPGQSLEYIG

QIWRWKSSASHHFRGRVLISAVDLTGSSPPISSLEIKNLTSDDTAVYFCT

TTSTYDKWSGLHHDGVMAFSSRGQGTLISVSAASTKG;

(g22; SEQ ID NO: 7)
QIHLVQSGTEVKKPGSSVTVSCKAYGVNTFGLYAVNWVRQAPGQSLEYIG

QIWRWKSSASHHFRGRVLISAVDLTGPSPPISSLEIKNLTSDDTAVYFCT

TTSTYDKWSGLHHDGVMAFSSWGQGTLISVSAASTKG;

(g15; SEQ ID NO: 8)
QIHLVQSGTEVKKPGSSVTVSCKAYGVNTFGLYAVNWVRQAPGQSLEYIG

QIWRWKSSASHHFRGRVIISAVDLTGSSPPISSLEIKNLTSDDTAVYFCT

TASTYDKWSGLHHDGVMAFSSWGQGTLISVSAASTKG;

(g4; SEQ ID NO: 9)
QIHLVQSGTEVKKPGSSVTVSCKAYGVNTFGLYAVNWVRQAPGQSLEYIG

QIWRWKSSASHHFRGRVIISAVDLTGSSPPISPLEIKNLTSDDTAVYFCT

TTSTSDRWSGLHHDGVMAFSSWGQGTLISVSAASTKG;
```

(g46; SEQ ID NO: 10)
QIHLVQSGTEVKKPGSSVTVSCKAYGVNTFGLYAVNWVRQAPGQGLEYIG

QIWRWKSSASHHFRGRVLISAVDLTGSSPPISSLEIKNVTSDDTAVYFCT

TTSTYDKWSGLHHDGVVAFSSWGQGTLISVSAASTKG;

(g44; SEQ ID NO: 11)
QIHLVQSGTEVKKPGSSVTVSCKAYEVNTFGLYAVNWVRQAPGQSLEYIG

QIWRWKSSASHHFRGRVLISAVDLTGSSPPISSLEIKNVTSDDTAVYFCT

TTSTHDKWSGLHHDGVMAFSSWGQGTLISVSAASTKG;

(g50; SEQ ID NO: 12)
QIHLVQSGTEVKKPGSSVTVSCKAYGVNTFGLYAVNWVRQAPGQGLEYIG

QIWRWKSSASHHFRGRVLISAIDLTGSSPPISSLEIKNVTSDDTAVYFCT

TMSTYDKWSGLHHDGVMAFSSWGQGTLISVSAASTKG;

(g3; SEQ ID NO: 13)
QIHLVQSGTEVKKPGSSVTVSCKAYGVNTFGLYAVSWVRQAPGQRLEYIG

QIRRWKSSASHHFRGRVTVSAVDPTGSSPPISSLEIRDLTTDDTAVYFCT

TTSTSDYWSGLHNERGTAFSSWGQGTLISVSAASTKG;

(3040HC; SEQ ID NO: 14)
QIHLVQSGTEVKKPGSSVTVSCKAYGVNTFGLYAVNWVRQAPGQSLEYIG

QIWRWKSSASHHFRGRVLISAVDLTGSSPPISSLEIKNLTSDDTAVYFCT

TTSTYDQWSGLHHDGVMAFSSWGQGTLISVSAASTKG;

(3430HC; SEQ ID NO: 15)
QIHLVQSGTEVKKPGSSVTVSCKAYGVNTFGLYAVNWVRQAPGQSLEYIG

QIWRWKSSASHHFRGRVIISAVDLTGSSPPISSLEIKNLTSDDTAVYFCT

TTSTSDYWSGLHHDGVMAFSSWGQGTLISVSAASTKG;

(3484HC; SEQ ID NO: 16)
QIHLVQSGTEVKKPGSSVTVSCKAYGVNTFGLYAVNWVRQAPGQSLEYIG

QIWRWKSSASHHFRGRVLISAVDLTGSSPPISSLEIKNLTSDDTAVYFCT

TTSTYDRWSGLHHDGVMAFSSWGQGTLISVSAASTKG;

(3044HC: SEQ ID NO: 17)
QIHLVQSGTEVRKPGSSVTVSCKAYGVNTFGLYAVNWVRQAPGQSLEYIG

QIWRWKSSASHHFRGRVLISAVDLTGSSPPISSLEIKNLTSDDTAVYFCT

TTSTYDKWSGLHHDGVMAFSSWGQGTLISVSAASTKG;
and (3630HC: SEQ ID NO: 18)
QIHLVQSGTEVKKPGSSVTVSCKAYGVNTFGLYAVNWVRQAPGQSLEYIG

QIWRWKSSASHHFRGRVLISAVDLTGSSPPISSLEIKNLTSDDTAVYFCT

TTSTYDRWSGLHHDGVMAFSSWGQGTLISVSAASTKG.

In one embodiment, the antibody comprises a light chain having one of the following amino acid sequences:

(k3; SEQ ID NO:19)
DIQMTQSPSTLSASIGDTVRISCRASQSITGNWLAWYHQRPGKAPRLLIYR

GSRLLGGVPSRFSGSAAGTDFTLTIANLQAEDFGTFYCQQYDTYPGTFGQG

TKVEVKRTVAAPSVF;

(k5; SEQ ID NO: 20)
DIQMTQSPSTLSASTGDTVRISCRASQSITGNWVAWYQQRPGKAPRLLIYR

GAALLGGVPSRFRGSAAGTDFTLTIGNLQAEDFGTFYCQQYDTYPGTFGQG

TKVEVKRTVAAPSVF;

(k59; SEQ ID NO: 21)
DIQMTQSPSTLSASIGDTVRISCRASQSITGGWLAWYHQRPGKAPRLLIYR

GSRLLGGVPSKFSGSAAGTDFTLTIANLQAEDFGTFYCQQYDTYPGTFGQG

TKVEVKRTVAAPSVF;

(k62; SEQ ID NO: 22)
DIQMTQSPSTLSASIGDTVRISCRASQSITGGWLAWYHQRPGKAPRLLIYR

GSRLVGGVPSRFSGSAAGTDFTLTIGNLQAEDFGTFYCQQYDTYPGTFGQG

TKVEVKRTVAAPSVF;

(k18; SEQ ID NO: 23)
DIQMTQSPSTLSASVGDTVRISCRASQSITGGWLAWYHQRPGKAPRLLIYR

GSRLLGGVPSRFSGSAAGADFTLTIANLQAEDFGTFYCQQYDTYPGTFGQG

TKVEVKRTVAAPSVF;

(k53; SEQ ID NO: 24)
DIQMTQSPSTLSASIGDTVMISCRASQSITGGWLAWYHQRPGKAPRLLIYR

GSKLLGGVPSRFSGSAAGTGFTLTIGNLQAEDFGTFYCQQYDTYPGTFGQG

TKVEVKRTVAAPSVF;

(k61; SEQ ID NO: 25)
DIQMTQSPSTLSASIGDTVRISCRASQSITGNWVAWYHQRPGKAPRLLIYR

GAALLGGVPSRFSGSAAGTDFTLTIGNLQAEDFGTFYCQQYDTYPGTFGQG

TKVEVKRTVAAPSVF;

(k11; SEQ ID NO: 26)
DIQMTQSPSTLSASVGGTVRISCRASQSITGGWLAWYHQRPGKAPRLLIYR

GSRLLGGVPSRFSGSAAGTDFTLTIANLQAEDFGTFYCQQYDTYPGTFGQG

TKVEVKRTVAAPSVF;

(k19; SEQ ID NO: 27)
DIQMTQSPSTLSASVGDTVRISCRASQSITGGWLAWYHQRPGKAPRLLIYR

GSRLLGGVPSRFSGSAAGTGFTLTIGNLQAEDFGTFYCQQYDTYPGTFGQG

TKVEVKRTVAAPSVF;

(k81; SEQ ID NO: 28)
DIQMTQSPSTLSASIGDTVRISCRASQSITGGWVAWYHQRPGKAPRLLIYR

GSRLLGGVPSRFSGSAAGTDFTLTIGNLQAEDFGTFYCQQYDTYPGTFGQG

TKVEVKRTVAAPSVF (3040LC; SEQ ID NO: 29)
DIQMTQSPSTLSASIGDTVRISCRASQSITGNWVAWYQQRPGKAPRLLIYR

GAALLGGVPSRFSGSAAGTDFTLTIGNLQAEDFGTFYCQQYDTYPGTFGQG

TKVEVKRTVAAPSVF;

(3430LC; SEQ ID NO: 30)
DIQMTQSPSTLSASVGDTVRISCRASQSITGGWLAWYHQRPGKAPRLLIYR

GSRLLGGVPSRFSGSAAGTDFTLTIANLQAEDFGTFYCQQYDTYPGTFGQG

TKVEVKRTVAAPSVF;

-continued (3484LC; SEQ ID NO: 31)
DIQMTQSPSTLSASIGDTVRISCRASQSITGNWVAWYQQRPGKAPRLLIYR

GAALLGGVPSRFRGSAAGTDFTLTIGNLQAEDFGTFYCQQYDTYPGTFGQG

TKVEVKRTVAAPSVF;

(3044LC; SEQ ID NO: 32)
DIQMTQSPSTLSASIGDTVRISCRASQSITGNWVAWYQQRPGKAPRLLIYR

GAALLGGVPSRFSGSAAGTDFTLTIGNLQTEDFGTFYCQQYDTYPGTFGQG

TKVEVKRTVAAPSVF;
and (3630LC; SEQ ID NO: 33)
DIQMTQSPSTLSASIGDTVRISCRASQSITGGWLAWYHQRPGKAPRLLIYR

GSRLLGGVPSRFSGSAAGTDFTLTIANLQAEDFGTFYCQQYDTYPGTFGQG

TKVEVKRTVAAPSVF.

Accordingly, one aspect of this invention features an isolated polypeptide comprising the sequence of any one of SEQ ID NOs: 1-33. The invention also provides an isolated anti-HIV antibody comprising one or both of a heavy chain comprising the sequence of any one of SEQ ID NOs: 1-18 and a light chain comprising the sequence any one of SEQ ID NOs: 19-33.

The above-mentioned antibody can be a human antibody, a chimeric antibody, or a humanized antibody. It can be an IgG1, IgG2, IgG3, or IgG4. The antibodies of the invention recognize the epitope on the HIV-1 envelope spike recognized by 8ANC195 and are broadly neutralizing.

In another aspect, the invention provides an isolated nucleic acid encoding the isolated polypeptide or anti-HIV-1 antibody described above. Also provided are a vector comprising the nucleic acid and a cultured cell comprising the nucleic acid.

In another aspect, the invention provides a composition comprising at least one of the above-described isolated polypeptide or anti-HIV-1 antibody or a fragment thereof. In one embodiment, the composition comprises a pharmaceutically acceptable carrier.

In another aspect, the invention provides a method of preventing or treating an HIV-1 infection or an HIV-related disease. The method includes steps of identifying a patient in need of such prevention or treatment, and administering to the patient a first therapeutic agent comprising a therapeutically effective amount of at least one of the above-described isolated polypeptide or anti-HIV-1 antibody. The method can further comprise administering a second therapeutic agent, such as an antiviral agent.

In another embodiment, the present invention provides an isolated antigen comprising an epitope-scaffold that mimics the HIV-1 envelope spike epitope of broadly neutralizing antibody 8ANC195. In one aspect, the epitope-scaffold comprises a discontinous epitope and a scaffold. In another aspect, the epitope is derived from HIV-1 gp120 and gp41, and at least part of the scaffold is not derived from gp120 or gp41. In another aspect, the discontinuous epitope comprises amino acids corresponding to amino acid numbers 44-47, 90-94, 97, 234, 236-238, 240, 274-278, 352-354, 357, 456, 463, 466, 487, and 625-641 of gp140 from HIV strain 93TH057 numbered using standard numbering for HIV strain HXBC2. The amino acids corresponding to amino acid numbers 234 and 276 may be glycosylated.

In another aspect, the invention provides an isolated nucleic acid encoding the isolated antigen described above. Also provided are a vector comprising the nucleic acid and a cultured cell comprising the nucleic acid.

In another aspect, the invention provides a composition comprising the isolated antigen. In one embodiment, the composition further comprises a pharmaceutically acceptable carrier. In one embodiment, the composition further comprises an adjuvant.

In another aspect, the present invention provides a method for generating an immune response in a subject in need thereof, comprising administering to said subject a composition comprising the above-described isolated antigen in an amount effective to generate an immune response.

In another aspect, the invention provides a method of preventing or treating an HIV-1 infection or an HIV-related disease. The method includes steps of identifying a patient in need of such prevention or treatment, and administering to the patient a first therapeutic agent comprising a therapeutically effective amount of the above-described antigen. The method can further comprise administering a second therapeutic agent, such as an antiviral agent.

In another aspect, the present invention provides a method for detecting or isolating an HIV-1 binding antibody in a subject comprising obtaining a biological sample from the subject, contacting the sample with the above-described antigen, and conducting an assay to detect or isolate an HIV-1 binding antibody.

The details of one or more embodiments of the invention are set forth in the description below. Other features, objects, and advantages of the invention will be apparent from the description and from the claims.

BRIEF DESCRIPTION OF THE DRAWINGS

Figures 1A, 1B:
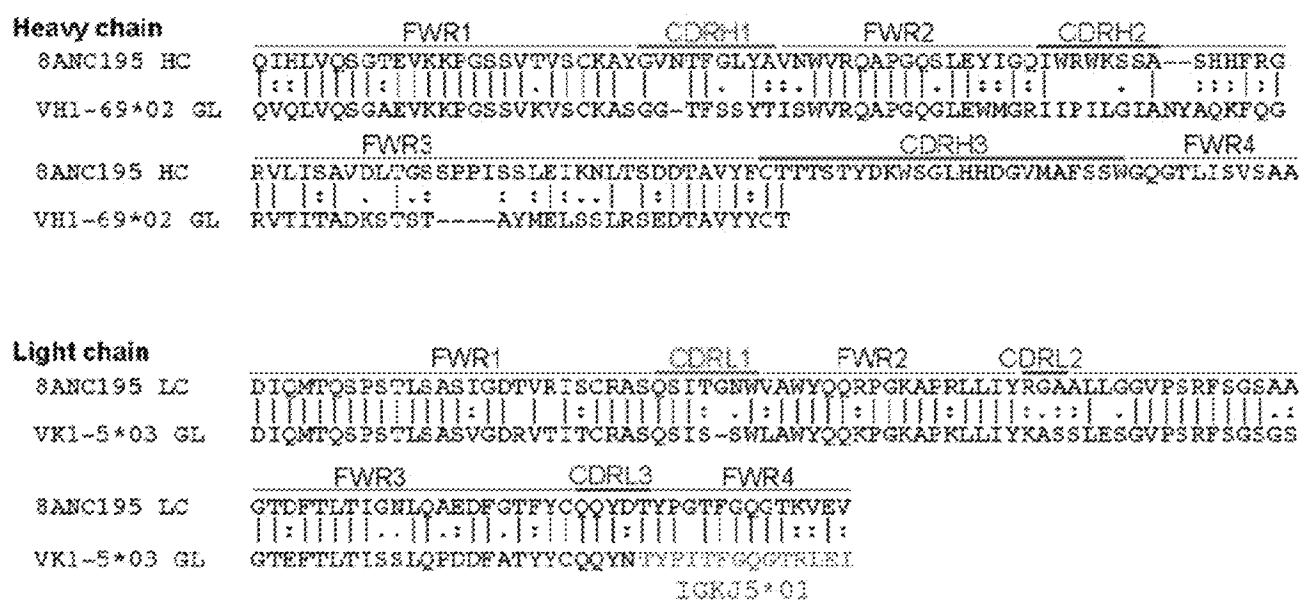

FIGS. 1A and 1B illustrates alignments of (A) VH and (B) VL sequences of mature 8ANC195 and its putative germline progenitor (GL). 8ANC195 HC has the sequence of SEQ ID NO:34. 8ANC195 LC has the sequence of SEQ ID NO:35. GL HC has the sequence of SEQ ID NO:36. GL LC has the sequence of SEQ ID NO:37. Residues forming the CDR loops are labeled (CDR1), (CDR2) and (CDR3). 8ANC195 is one of the most heavily mutated bNAbs isolated to date, with 49 of 103 amino acid mutations in the HC and 25 of 90 in the LC. The HC was too highly somatically mutated to accurately assign D and J gene segments, but the LC showed sufficient homology to assign its J segment as IGKJ5*01.

FIGS. 4A, 4B, 4C, 4D, 4E, 4F, 4G, 4H and 4I illustrates surface area buried at interface of 8ANC195 Fab and gp120. Left panels, surface area buried on 8ANC195 Fab by (A) gp120 protein residues, (C) Asn276gp120 glycan or (E) Asn234gp120 glycan; right panels, surface area buried by 8ANC195 Fab on (B) gp120 protein residues, (D) Asn234gp120 glycan or (F) Asn276gp120 glycan. Atoms buried at these interfaces are shown as surface representations overlaid onto ribbon diagrams of 8ANC195 Fab and gp120 or stick representations of glycans. 8ANC195 Fab: HC; LC; CDRH1; CDRH2; CDRH3; gp120: inner domain; outer domain; loop D; loop V5; Asn234gp120 glycan: Asn276gp120 glycan. 2Fo-Fc annealed omit electron density maps (grey mesh, σ=1) used to build (E) Asn234$_{gp120}$ glycan and (H) Asn276$_{gp120}$ glycan. (I) Modeled fucose residue α1-6-linked to the first N-acetylglucosamine residue of the Asn276$_{gp120}$ glycan shows that the core fucose of a complex-type N-glycan could be accommodated by the 8ANC195. Glycan residues are shown as sticks, and gp120, 8ANC195 HC and CD4 are shown as surface representations.

FIGS. 6A, 6B and 6C illustrates green EM refinement statistics. (A) Electron micrograph at 52,000× magnification and −0.8 μm defocus. (B) Reference-free 2D class averages of the SOSIP trimer in complex with 8ANC195 Fab showing various orientations. (C) Fourier Shell Correlation (FSC) graph resulting from refinement. The resolution was determined as 18.7 Å at an FSC cut-off of 0.5.

FIGS. 8A, 8B, 8C and 8D illustrates EM reconstruction of 8ANC195 Fab/BG505 SOSIP.664 showing gp41 contacts. Top view of EM density with the X-ray structures of BG505 SOSIP.664 (PDB ID 4NCO; gp120, grey; gp41) and 8ANC195 Fab (HC; LC with a map contour level of 0.0176 (A) and 0.030 (B). Areas of contact between 8ANC195 and gp41 are marked with circles, those between 8ANC195 and gp120 with black circles. (C,D) Close-up of 8ANC195 LC and HR2 region in EM complex structure (HR2 coordinates in PDB 4NCO with presumptive sidechains for strain YU2 added to the polyalanine coordinates). (C) Fab is shown as a surface representation with highlights (CDRL1; CDRL2; CDRH3, and gp41 HR2 is shown as a ribbon diagram. The position of Asn637gp41 was deduced from the position of the C-terminus of the SOSIP.664 trimer (Gly664gp41). (D) 8ANC195 HC and LC residues (sticks) positioned to contact HR2, with side chains of surface-exposed residues that vary between newly isolated 8ANC195 (T/K) variants shown as sticks.

FIGS. 10A and 10B depict the alignment of amino acid sequences of all distinct single cell versions of the 8ANC195 clone. HC (10A) and LC (10B) sequences were aligned with the respective germline genes. Mutations introduced by somatic hypermutation are indicated. In (10A), the HC sequences are as follows: VH1-69GL (SEQ ID NO: 61), 8ANC2080 (SEQ ID NO: 62), 8ANC3035 (SEQ ID NO: 63), 8ANC3369 (SEQ ID NO: 64), 8ANC3625 (SEQ ID NO: 65), 8ANC3040 (SEQ ID NO: 66), 8ANC3288 (SEQ ID NO: 67), 8ANC3630 (SEQ ID NO: 43), 8ANC3430 (SEQ ID NO: 40), 8ANC3484 (SEQ ID NO: 41), 8ANC3044 (SEQ ID NO: 42), and 8ANC3509 (SEQ ID NO: 72). In (10B), the LC sequences are as follows: VK1-5GL (SEQ ID NO: 73), 8ANC2080 (SEQ ID NO: 74), 8ANC3035 (SEQ ID NO: 75), 8ANC3369 (SEQ ID NO:

76), 8ANC3625 (SEQ ID NO: 77), 8ANC3040 (SEQ ID NO: 78), 8ANC3288 (SEQ ID NO: 79), 8ANC3630 (SEQ ID NO: 49), 8ANC3430 (SEQ ID NO: 46), 8ANC3484 (SEQ ID NO: 47), 8ANC3044 (SEQ ID NO: 48), and 8ANC3509 (SEQ ID NO: 84).

FIGS. 11A, 11B, and 11C are directed to Bulk Sorted Variants of 8ANC195. (11A) Strategy of bulk memory B cell sorting without antigen. (11B) PCR strategy for the amplification of 8ANC195 HC and LC clone members. Shown are the priming sites aligned with the original nucleotide sequence of 8ANC195 at the respective sites. Mismatches with the respective germline genes are indicated. Primers 1 and 2 for the 8ANC195 HC FWR1 have SEQ ID Nos: 50 and 51, respectively. The 8ANC195 HC FWR1 original nucleotide sequence is SEQ ID NO: 85. Primers 1 and 2 for the 8ANC195 LC FWR1 have SEQ ID Nos: 52 and 53, respectively. The 8ANC195 LC FWR1 original nucleotide sequence is SEQ ID NO: 86. The primer for the 8ANC195 HC J-gene has SEQ ID NO: 54. The 8ANC195 HC J-gene original nucleotide sequence is SEQ ID NO: 87. Primers 1 and 2 for the 8ANC195 LC J-gene have SEQ ID Nos: 55 and 56, respectively. The 8ANC195 LC J-gene original nucleotide sequence is SEQ ID NO: 88. (11C) Phylogenetic tree of 128 isolated HC and 100 LC sequences. Representative members chosen for alignment are indicated.

Figures 12A, 12B:
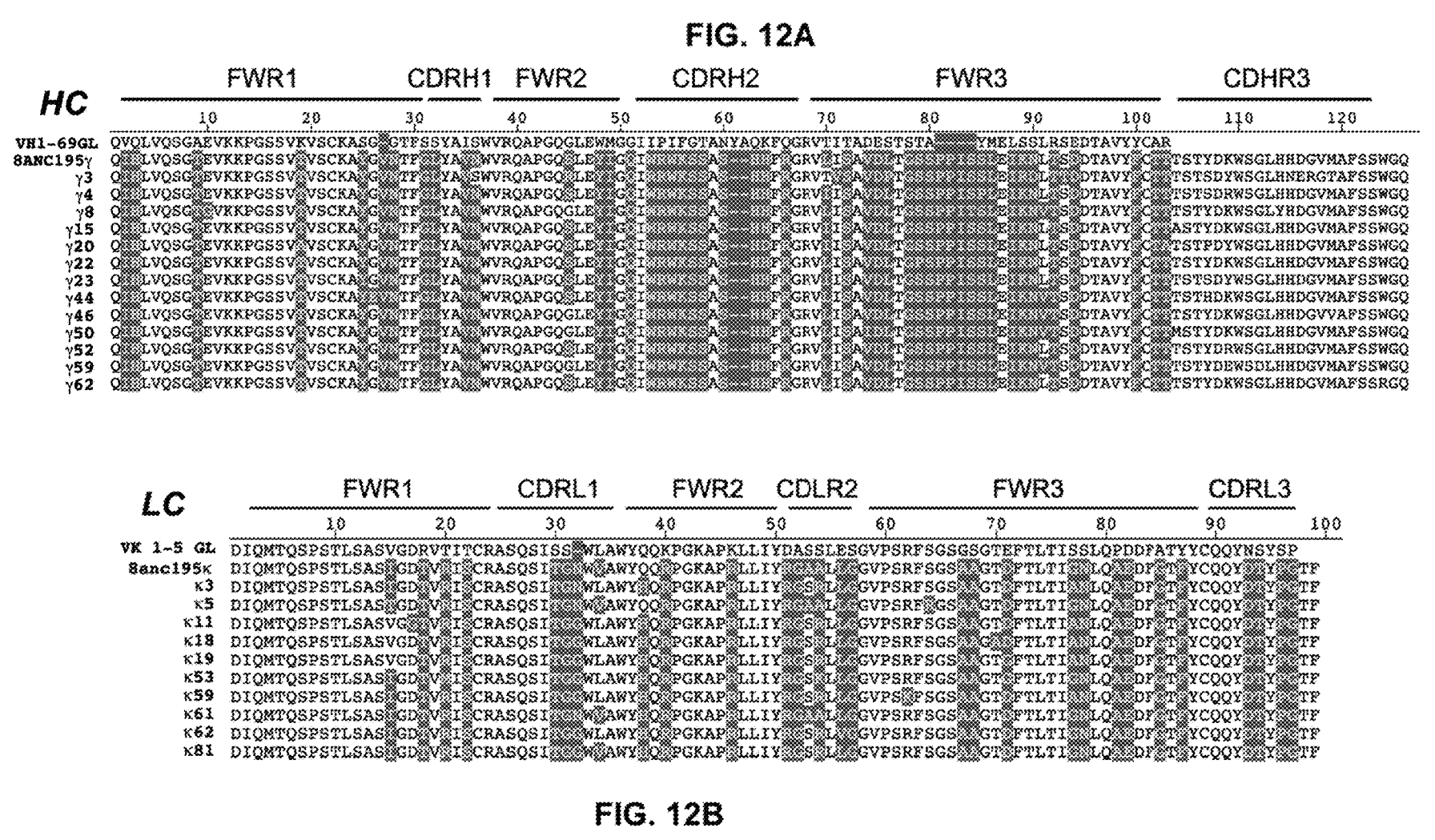

FIGS. 12A and 12B depict alignment of amino acid sequences of selected bulk sorted versions of the 8ANC195 clone. HC (12A) and LC (12B) sequences were aligned with the respective germline genes as well as the original 8ANC195 sequence. All mutations introduced by somatic hypermutation are indicated. In (12A), the HC sequences are as follows: VH1-69GL (SEQ ID NO: 61), 8ANC195γ (SEQ ID NO: 89), γ3 (SEQ ID NO: 90), γ4 (SEQ ID NO: 91), γ8 (SEQ ID NO: 92), γ15 (SEQ ID NO: 93), γ20 (SEQ ID NO: 94), γ22 (SEQ ID NO: 95), γ23 (SEQ ID NO: 96), γ44 (SEQ ID NO: 97), γ46 (SEQ ID NO: 98), γ50 (SEQ ID NO: 99), γ52 (SEQ ID NO: 100), γ59 (SEQ ID NO: 101), and γ62 (SEQ ID NO: 102). In (12B), the LC sequences are as follows: VK 1-5 GL (SEQ ID NO: 103), 8anc195κ (SEQ ID NO: 104), κ3 (SEQ ID NO: 105), κ5 (SEQ ID NO: 106), κ11 (SEQ ID NO: 107), κ18 (SEQ ID NO: 108), κ19 (SEQ ID NO: 109), κ53 (SEQ ID NO: 110), κ59 (SEQ ID NO: 111), κ61 (SEQ ID NO: 112), κ62 (SEQ ID NO: 113), and κ81 (SEQ ID NO: 114).

Figures 13A, 13B:
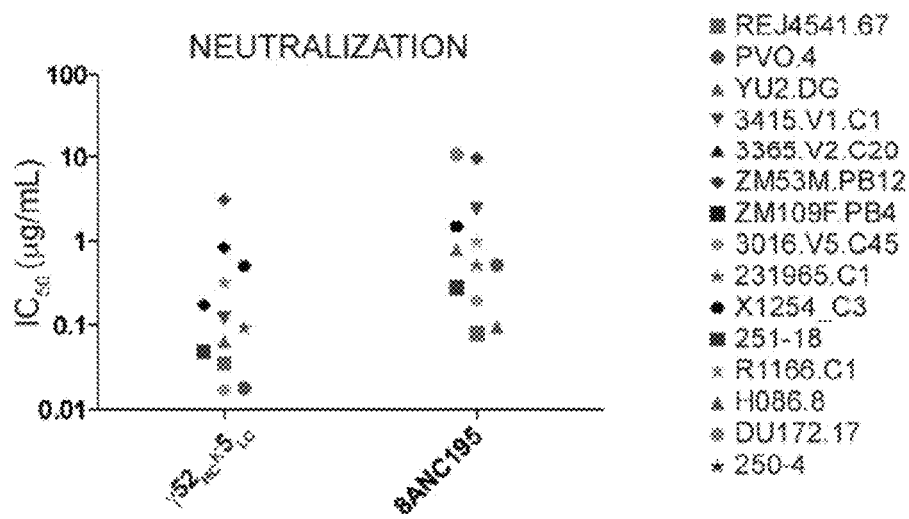

FIGS. 13A and 13B show that $\gamma 52_{HC} \kappa 5_{LC}$ is more potent than 8ANC195. $IC_{50}$ values of γ52HC κ5LC and 8ANC195 against Tier 2 15 virus panel shown as dot plot (A) and Table (B). NT, not tested.

Figure 14A:
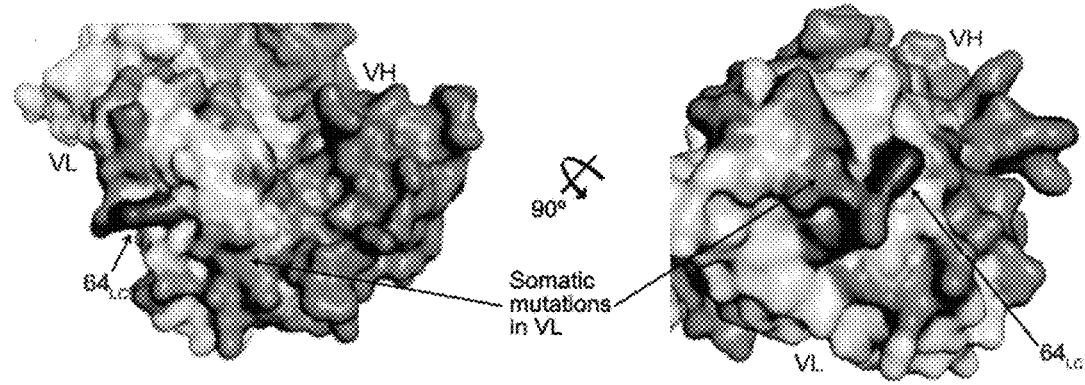
Figure 14B:
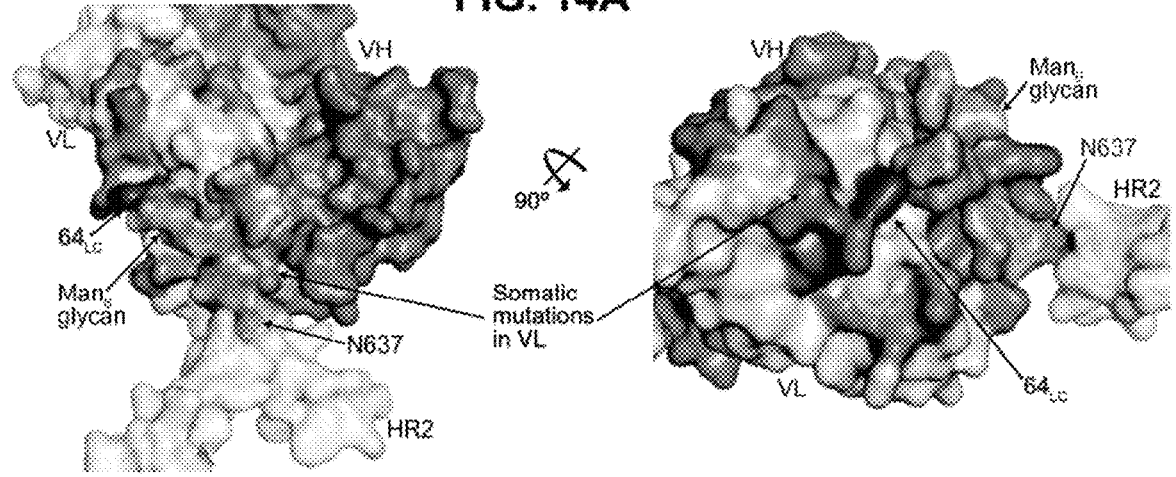
Figure 14C:
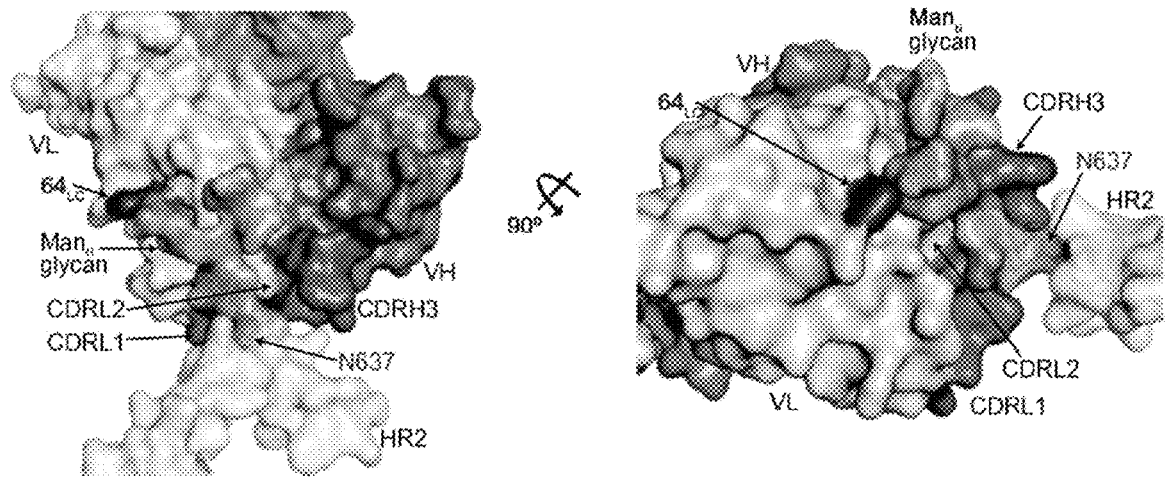

FIGS. 14A, 14B and 14C show that somatic mutations in the 8ANC195 LC CDRs and FWRs could affect contacts with gp41. (A) Surface representation of 8ANC195 Fab (HC; LC; somatically mutated, surface-exposed LC residues; residue $64_{LC}$). (B) Surface representation of 8ANC195 Fab and BG505 gp41 HR2 with a modeled Man6 sugar attached to Asn637gp41. (C) Surface representation of 8ANC195 Fab (CDRL1; CDRL2; CDRH3; residue $64_{LC}$) and BG505 gp41 HR2 with a modeled Man6 sugar attached to Asn637gp41.

Figure 15:
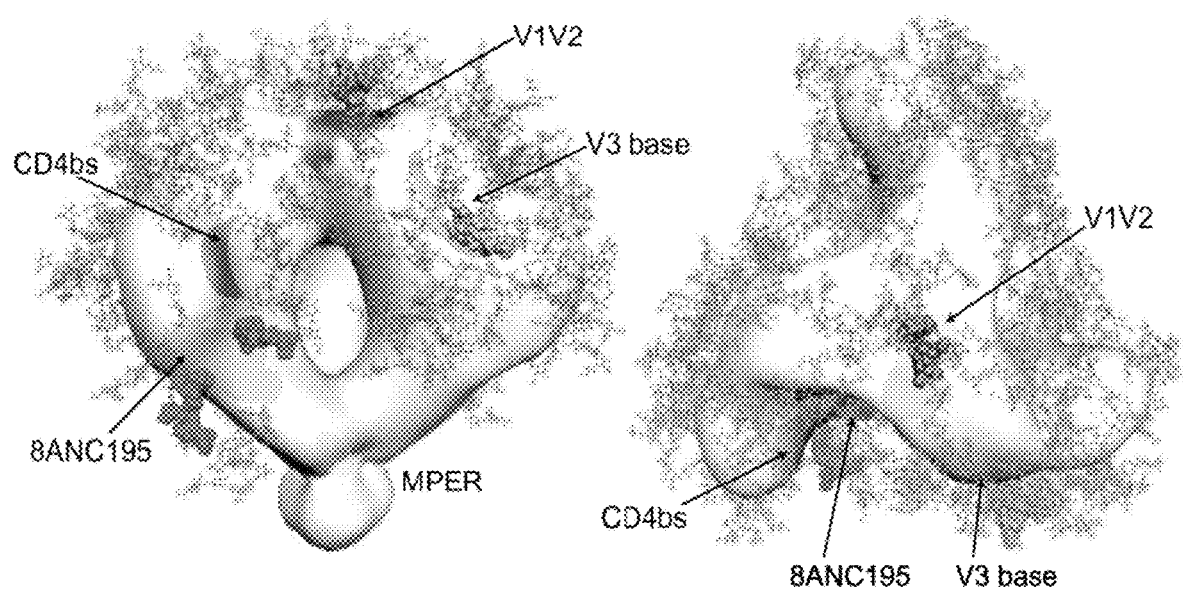

FIG. 15 illustrates locations of bNAb epitopes on HIV-1 Env Trimer. EM density map of Env trimer including MPER region showing approximate epitope locations for antibodies targeting the 8ANC195 epitope, CD4 binding site, V3 loop/Asn332 glycan (332 glycan shown as spheres), V1/V2 loop/Asn160 glycan (160 glycan shown as spheres), and MPER.

FIGS. 16A, 16B and 16C illustrate crystal structures of 8ANC195 Fab and 8ANC195/gp120/sCD4 complex. (A) Superimposition of unbound and bound (HC and LC) structures of 8ANC195 Fab shown as ribbon diagrams. CDR loops are highlighted (CDRH1/CDRL1; CDRH2/CDRL2; CDRH3; CDRL3) and a "thumb"-like loop formed by an insertion in FWR3 is indicated. Disordered loops are shown as dashed lines. (B) Space-filling model (inset) and ribbon diagram of ternary complex of 8ANC195 (HC and LC), sCD4, and 93TH057 gp120 core (inner domain; outer domain; bridging sheet; loop D; loop V5; CD4 binding loop). Ordered glycans attached to $Asn234_{gp120}$ and $Asn276_{gp120}$ are shown as sticks. Fab CDR loops are indicated as in (A). sCD4 was omitted from the right panel for clarity. (C) Approximate locations of bNAb epitopes on a surface representation of the gp120 core. The epitopes of V3 and V1/V2 antibodies include regions of loops (dotted lines) not present in the gp120 core structure. CD4 binding site and 8ANC195 epitopes are outlined by black (CD4 binding site) and (8ANC195) dots. Glycans included in the 8ANC195 epitope are indicated. Subdomains of gp120 are indicated as in (B).

FIGS. 17A, 17B, 17C, 17D and 17E show contacts made by 8ANC195 HC with gp120 protein residues and glycans. Labels for gp120 protein and glycan residues are italicized. Hydrogen bonds are shown as dashed lines. (A) $FWR3_{HC}$ loop contacts with loop D, loop V5, and outer domain loop. (B) 8ANC195 HC CDRH1 and CDRH3 contacts with gp120 inner domain. (C) Buried surface area between the $Asn234_{gp120}$ glycan (transparent surface with glycan residues shown as sticks) and 8ANC195 (HC FWR residues and CDRH2 are indicated). Antibody atoms buried by glycan interactions are shown as surfaces. (D) Buried surface area between the Asn276 glycan 120 (transparent surface with glycan residues shown as sticks) and 8ANC195 (HC FWR residues and CDRH1 are indicated). Antibody atoms buried by glycan interactions are shown as surfaces. (E) Top: Contacts made by 8ANC195 HC FWR residues and CDRH2 with $Asn234_{gp120}$ glycan. Glycan and protein residues involved in hydrogen bonds are shown as sticks. Bottom: schematic of ordered high mannose glycans on $Asn234_{gp120}$ and $Asn276_{gp120}$ (bottom).

FIGS. 18A and 18B show the EM structure of 8ANC195/Env trimer complex and model of 8ANC195 LC interactions with gp41 HR2. (A) EM reconstruction of 8ANC195 Fab/BG505 SOSIP.664. Side (left) and top (right) views of EM density with the X-ray structures of BG505 SOSIP.664 (PDB ID 4NCO; gp120, gp41) and 8ANC195 Fab fit in two ways: (i) fitting 8ANC195 Fab independently of gp140 coordinates to the EM density (best fit/independently placed), and (ii) by aligning the gp120 of the gp120/8ANC195 complex structure onto the gp120 of PDB 4NCO fit to the EM density. (B) Close-up of 8ANC195 LC/HR2 region of EM complex structure (Fab placement is best fit/independently placed as in (A)). Left: Fab is shown as a surface representation with highlights (CDRL1; CDRL2; CDRH1; CDRH3), and gp140 is shown as a ribbon diagram (gp120; gp41). The position of $Asn637_{gp41}$ was deduced from the position of the C-terminus of the SOSIP.664 trimer ($Gly664_{gp41}$). Right: 8ANC195 HC and LC residues (sticks) positioned to contact HR2, which is shown as a surface representation calculated from HR2 coordinates in PDB 4NCO with presumptive sidechains added to the polyalanine coordinates.

FIGS. 19A, 19B and 19C show effects of LC sequence changes on 8ANC195 neutralization potency. (19A) Sequences of LC CDRs in constructs used with 8ANC195 HC to make chimeric IgGs (left) and location of CDRs on 8ANC195 structure (right). Sequences derived from the mature antibody are shown and those derived from the germline precursor are shown on a grey background. The mutations introduced into CDRL3 in glCDRL3Ala are shown on a white background. The 8ANC195 LC CDRL1 sequence is SEQ ID NO: 115. The glCDRL1 LC CDRL1 sequence is SEQ ID NO: 117. The Vκ1-5 gl LC CDRL1 sequence is SEQ ID NO: 120. The 8ANC195 LC CDRL3 sequence is SEQ ID NO: 116. The glCDRL3 LC CDRL3 sequence is SEQ ID NO: 118. The glCDRL3Ala LC CDRL3 sequence is SEQ ID NO: 119. The Vκ1-5 gl LC CDRL3 sequence is SEQ ID NO: 121. (19B) Effects of changes in 8ANC195 LC on binding to 93TH057 and YU2 gp120s and neutralization of viral strains, expressed as fold changes over results for 8ANC195 IgG. KD and $IC_{50}$ values for these experiments are shown in table S3. (19C) Heat map showing the expression and neutralization of randomly paired HCs and LCs from the bulk sort on a Tier 2 15-virus panel. Average $IC_{50}$ values (arithmetic means) between 0.1 and 2 µg/ml; between 2.1 and 10 µg/ml, between 10.1 and 14.9 µg/ml, and above 15 µm/ml are indicated with varying degrees of shaded squares. Empty squares represent insufficient antibody expression.

Figure 20:
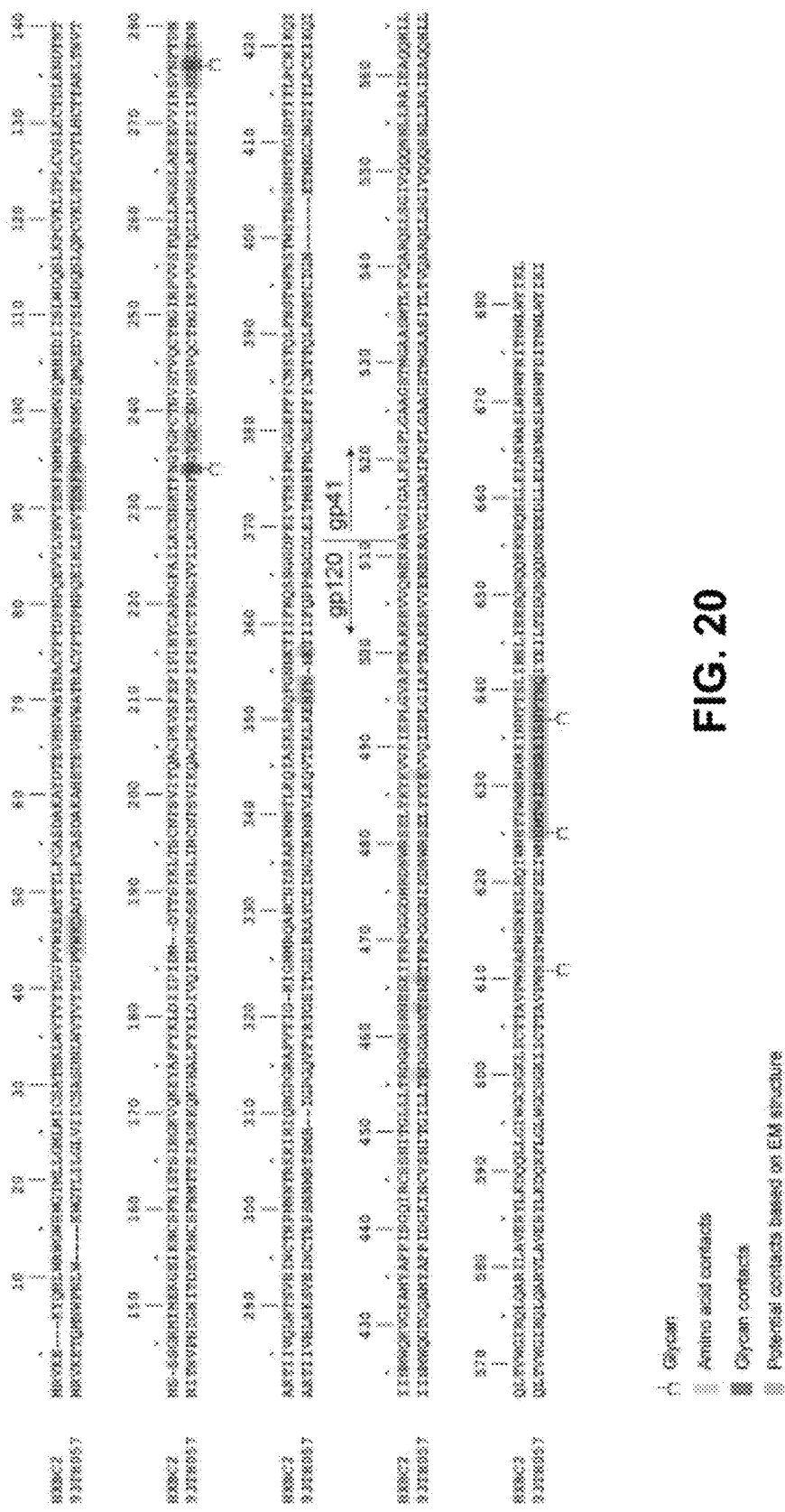

FIG. 20 depicts the alignment of gp140 sequences from HIV strains HXBC2 (SEQ ID NO: 122) and 93TH057 (SEQ ID NO: 123) using standard HXBC2 numbering of amino acid residues. Amino acid residues contacted by 8ANC195 in the complex crystal structure with 93TH057 gp120 core are indicated on the 93TH057 sequence. Glycans contacted by 8ANC195 in the complex crystal structure with 93TH057 gp120 core are shown as the asparagine residues to which they are attached, highlighted in cyan on the 93TH057 sequence. The region of gp41 contacted by 8ANC195 based on the EM complex structure is indicated. Select glycans are shown as diagrams on the asparagine residues to which they are attached.

DETAILED DESCRIPTION OF THE INVENTION

The present invention is based, at least in part, on the identification of the epitope recognized by 8ANC195, a broadly neutralizing antibody to the HIV-1 envelope glycoprotein. The present invention, in one embodiment, provides an isolated antigen comprising the epitope, compositions comprising the antigen, and methods of using the antigen. In other embodiments, the present invention provides isolated ant-HIV-1 antibodies that recognize the epitope on the HIV-1 envelope spike recognized by 8ANC195, compositions comprising the antibodies, and methods of using the antibodies.

In one embodiment, the present invention is directed to an isolated anti-HIV antibody comprising one or both of a heavy chain comprising the sequence of any one of SEQ ID NOs: 1-18 and a light chain comprising the sequence any one of SEQ ID NOs: 19-33. In one preferred embodiment, the heavy chain comprises the sequence of SEQ ID NO:1 and the light chain comprises the sequence of SEQ ID NO:20. In another embodiment, the present invention provides an isolated polypeptide comprising the sequence of any one of SEQ ID NOs: 1-33.

The above-mentioned antibody can be a human antibody, a chimeric antibody, or a humanized antibody. It can be an IgG1, IgG2, IgG3, or IgG4. The antibodies of the invention recognize the epitope on the HIV-1 envelope spike recognized by 8ANC195 and are broadly neutralizing. 8ANC195 is known in the art and disclosed, for example, by Scheid et al., Science, 333, 1633 (2011). The heavy chain of 8ANC195 has the sequence of SEQ ID NO:34 and the light chain of 8ANC195 has the sequence of SEQ ID NO:35.

The term "antibody" (Ab) as used herein includes monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). It is understood in the art that an antibody is a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, and FWR4. The variable regions of the heavy and light chains contain a binding domain that interacts with an antigen while, depending of the isotype, the constant region(s) may mediate the binding of the immunoglobulin to host tissues or factors.

Also included in the definition of "antibody" as used herein are chimeric antibodies, humanized antibodies, and recombinant antibodies, human antibodies generated from a transgenic non-human animal, as well as antibodies selected from libraries using enrichment technologies available to the artisan.

The term "variable" refers to the fact that certain segments of the variable (V) domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta sheet configuration, connected by three hypervariable regions, which form loops connecting, and in some cases forming part of, the beta sheet structure. The hypervariable regions in each chain are held together in close proximity by the FRs and, with the hypervariable regions from the other chain, contribute to the formation of the antigen-binding site of antibodies (see, for example, Kabat et al., Sequences of Proteins of Immunological Interest, 5th Ed. Public Health Service, National Institutes of Health, Bethesda, Md. (1991)).

The term "hypervariable region" as used herein refers to the amino acid residues of an antibody that are responsible for antigen binding. The hypervariable region generally comprises amino acid residues from a "complementarity determining region" ("CDR").

The term "monoclonal antibody" as used herein refers to an antibody obtained from a population of substantially homogeneous antibodies, i.e., the individual antibodies comprising the population are identical except for possible naturally occurring mutations that may be present in minor amounts. The term "polyclonal antibody" refers to preparations that include different antibodies directed against different determinants ("epitopes").

The monoclonal antibodies herein include "chimeric" antibodies in which a portion of the heavy and/or light chain is identical with, or homologous to, corresponding sequences in antibodies derived from a particular species or belonging to a particular antibody class or subclass, while the remainder of the chain(s) is identical with, or homologous to, corresponding sequences in antibodies derived from another species or belonging to another antibody class or subclass, as well as fragments of such antibodies, so long as they exhibit the desired biological activity (see, for example, U.S. Pat. No. 4,816,567; and Morrison et al., Proc. Natl. Acad. Sci. USA, 81:6851-6855 (1984)). Chimeric antibodies include antibodies having one or more human antigen binding sequences (for example, CDRs) and containing one or more sequences derived from a non-human antibody, for example, an FR or C region sequence. In addition, chimeric antibodies included herein are those comprising a human variable region antigen binding sequence of one antibody class or subclass and another sequence, for example, FR or C region sequence, derived from another antibody class or subclass.

A "humanized antibody" generally is considered to be a human antibody that has one or more amino acid residues introduced into it from a source that is non-human. These non-human amino acid residues often are referred to as "import" residues, which typically are taken from an "import" variable region. Humanization may be performed following the method of Winter and co-workers (see, for example, Jones et al., *Nature* 321:522-525 (1986); Reichmann et al., *Nature* 332:323-327 (1988); Verhoeyen et al., *Science* 239:1534-1536 (1988)), by substituting import hypervariable region sequences for the corresponding sequences of a human antibody. Accordingly, such "humanized" antibodies are chimeric antibodies (see, for example, U.S. Pat. No. 4,816,567), where substantially less than an intact human variable region has been substituted by the corresponding sequence from a non-human species.

An "antibody fragment" comprises a portion of an intact antibody, such as the antigen binding or variable region of the intact antibody. Examples of antibody fragments include, but are not limited to, Fab, Fab', F(ab')2, and Fv fragments; diabodies; linear antibodies (see, for example, U.S. Pat. No. 5,641,870; Zapata et al., Protein Eng. 8(10): 1057-1062 [1995]); single-chain antibody molecules; and multispecific antibodies formed from antibody fragments.

"Fv" is the minimum antibody fragment that contains a complete antigen-recognition and antigen-binding site. This fragment contains a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

"Single-chain Fv" ("sFv" or "scFv") are antibody fragments that comprise the VH and VL antibody domains connected into a single polypeptide chain. The sFv polypeptide can further comprise a polypeptide linker between the VH and VL domains that enables the sFv to form the desired structure for antigen binding. For a review of sFv, see, for example, Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins (VH and VL, respectively). They are highly expressed in microbial cell culture, show favorable biophysical properties including, for example, but not limited to, solubility and temperature stability, and are well suited to selection and affinity maturation by in vitro selection systems such as, for example, phage display. DAbs are bioactive as monomers and, owing to their small size and inherent stability, can be formatted into larger molecules to create drugs with prolonged serum half-lives or other pharmacological activities. Examples of this technology have been described in, for example, WO9425591 for antibodies derived from Camelidae heavy chain Ig, as well in US20030130496 describing the isolation of single domain fully human antibodies from phage libraries.

Fv and sFv are the only species with intact combining sites that are devoid of constant regions. Thus, they are suitable for reduced nonspecific binding during in vivo use. sFv fusion proteins can be constructed to yield fusion of an effector protein at either the amino or the carboxy terminus of an sFv. See, for example, Antibody Engineering, ed. Borrebaeck, supra. The antibody fragment also can be a "linear antibody", for example, as described in U.S. Pat. No. 5,641,870 for example. Such linear antibody fragments can be monospecific or bispecific.

In certain embodiments, antibodies of the described invention are bispecific or multispecific. Bispecific antibodies are antibodies that have binding specificities for at least two different epitopes. Exemplary bispecific antibodies can bind to two different epitopes of a single antigen. Other such antibodies can combine a first antigen binding site with a binding site for a second antigen. Alternatively, an anti-HIV arm can be combined with an arm that binds to a triggering molecule on a leukocyte, such as a T-cell receptor molecule (for example, CD3), or Fc receptors for IgG (Fc gamma R), such as Fc gamma RI (CD64), Fc gamma RII (CD32) and Fc gamma RIII (CD16), so as to focus and localize cellular defense mechanisms to the infected cell. Bispecific antibodies also can be used to localize cytotoxic agents to infected cells. Bispecific antibodies can be prepared as full length antibodies or antibody fragments (for example, F(ab')2 bispecific antibodies). For example, WO 96/16673 describes a bispecific anti-ErbB2/anti-Fc gamma RIII antibody and U.S. Pat. No. 5,837,234 discloses a bispecific anti-ErbB2/anti-Fc gamma RI antibody. For example, a bispecific anti-ErbB2/Fc alpha antibody is reported in WO98/02463; U.S.

Pat. No. 5,821,337 teaches a bispecific anti-ErbB2/anti-CD3 antibody. See also, for example, Mouquet et al., Polyreactivity Increases The Apparent Affinity Of Anti-HIV Antibodies By Heteroligation. NATURE. 467, 591-5 (2010).

Methods for making bispecific antibodies are known in the art. Traditional production of full length bispecific antibodies is based on the co-expression of two immunoglobulin heavy chain-light chain pairs, where the two chains have different specificities (see, for example, Millstein et al., Nature, 305:537-539 (1983)). Similar procedures are disclosed in, for example, WO 93/08829, Traunecker et al., EMBO J., 10:3655-3659 (1991) and see also; Mouquet et al., Polyreactivity Increases The Apparent Affinity Of Anti-HIV Antibodies By Heteroligation. NATURE. 467, 591-5 (2010).

Alternatively, antibody variable regions with the desired binding specificities (antibody-antigen combining sites) are fused to immunoglobulin constant domain sequences. The fusion is with an Ig heavy chain constant domain, comprising at least part of the hinge, CH2, and CH3 regions. According to some embodiments, the first heavy-chain constant region (CH1) containing the site necessary for light chain bonding, is present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Techniques for generating bispecific antibodies from antibody fragments also have been described in the literature. For example, bispecific antibodies can be prepared using chemical linkage. For example, Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated then are converted to thionitrobenzoate (TNB) derivatives. One of the Fab'-TNB derivatives then is reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Other modifications of the antibody are contemplated herein. For example, the antibody can be linked to one of a variety of nonproteinaceous polymers, for example, polyethylene glycol, polypropylene glycol, polyoxyalkylenes, or copolymers of polyethylene glycol and polypropylene glycol. The antibody also can be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in, for example, Remington's Pharmaceutical Sciences, 16th edition, Oslo, A., Ed., (1980).

Typically, the antibodies of the described invention are produced recombinantly, using vectors and methods available in the art. Human antibodies also can be generated by in vitro activated B cells (see, for example, U.S. Pat. Nos. 5,567,610 and 5,229,275). General methods in molecular genetics and genetic engineering useful in the present invention are described in the current editions of Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

Human antibodies also can be produced in transgenic animals (for example, mice) that are capable of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice results in the production of human antibodies upon antigen challenge. See, for example, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals can be genetically engineered to produce human antibodies comprising a polypeptide of the described invention.

Various techniques have been developed for the production of antibody fragments. Traditionally, these fragments were derived via proteolytic digestion of intact antibodies (see, for example, Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Fab'-SH fragments can be directly recovered from *E. coli* and chemically coupled to form F(ab')2 fragments (see, for example, Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner.

Other techniques that are known in the art for the selection of antibody fragments from libraries using enrichment technologies, including but not limited to phage display, ribosome display (Hanes and Pluckthun, 1997, *Proc. Nat. Acad.*

Sci. 94: 4937-4942), bacterial display (Georgiou, et al., 1997, *Nature Biotechnology* 15: 29-34) and/or yeast display (Kieke, et al., 1997, *Protein Engineering* 10: 1303-1310) may be utilized as alternatives to previously discussed technologies to select single chain antibodies. Single-chain antibodies are selected from a library of single chain antibodies produced directly utilizing filamentous phage technology. Phage display technology is known in the art (e.g., see technology from Cambridge Antibody Technology (CAT)) as disclosed in U.S. Pat. Nos. 5,565,332; 5,733,743; 5,871,907; 5,872,215; 5,885,793; 5,962,255; 6,140,471; 6,225,447; 6,291650; 6,492,160; 6,521,404; 6,544,731; 6,555,313; 6,582,915; 6,593,081, as well as other U.S. family members, or applications which rely on priority filing GB 9206318, filed 24 May 1992; see also Vaughn, et al. 1996, *Nature Biotechnology* 14: 309-314). Single chain antibodies may also be designed and constructed using available recombinant DNA technology, such as a DNA amplification method (e.g., PCR), or possibly by using a respective hybridoma cDNA as a template.

Variant antibodies also are included within the scope of the invention. Thus, variants of the sequences recited in the application also are included within the scope of the invention. Further variants of the antibody sequences having improved affinity can be obtained using methods known in the art and are included within the scope of the invention. For example, amino acid substitutions can be used to obtain antibodies with further improved affinity. Alternatively, codon optimization of the nucleotide sequence can be used to improve the efficiency of translation in expression systems for the production of the antibody.

The present invention provides for antibodies, either alone or in combination with other antibodies, such as, but not limited to, VRC01, anti-V3 loop, CD4bs, and CD4i antibodies as well as PG9/PG16-like antibodies, that have broad neutralizing activity in serum.

The present invention also relates to isolated polypeptides comprising the amino acid sequences of the light chains and heavy chains of the antibodies of the invention. In one embodiment, the isolated polypeptide comprises the sequence of any one of SEQ ID NOs: 1-33.

The term "polypeptide" is used in its conventional meaning, i.e., as a sequence of amino acids. The polypeptides are not limited to a specific length of the product. Peptides, oligopeptides, and proteins are included within the definition of polypeptide, and such terms can be used interchangeably herein unless specifically indicated otherwise. This term also includes post-expression modifications of the polypeptide, for example, glycosylations, acetylations, phosphorylations and the like, as well as other modifications known in the art, both naturally occurring and non-naturally occurring. A polypeptide can be an entire protein, or a subsequence thereof.

A polypeptide "variant," as the term is used herein, is a polypeptide that typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of techniques well known in the art.

For example, certain amino acids can be substituted for other amino acids in a protein structure without appreciable loss of its ability to bind other polypeptides (for example, antigens) or cells. Since it is the binding capacity and nature of a protein that defines that protein's biological functional activity, certain amino acid sequence substitutions can be made in a protein sequence, and, accordingly, its underlying DNA coding sequence, whereby a protein with like properties is obtained. It is thus contemplated that various changes can be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

Amino acid substitutions generally are based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In another embodiment, the present invention provides an isolated antigen comprising an epitope-scaffold that mimics the HIV-1 envelope spike epitope of broadly neutralizing antibody 8ANC195. On one embodiment, the epitope-scaffold comprises a discontinous epitope and a scaffold, wherein the epitope is derived from HIV-1 gp120 and gp41, and wherein at least part of the scaffold is not derived from gp120 or gp41. In one embodiment, the discontinuous epitope comprises amino acids corresponding to amino acid numbers 44-47, 90-94, 97, 234, 236-238, 240, 274-278, 352-354, 357, 456, 463, 466, 487, and 625-641 of gp140 from HIV strain 93TH057 numbered using standard numbering for HIV strain HXBC2 as depicted in FIG. 20 and disclosed by Korber et al. (1998, Numbering positions in HIV relative to HXBc2, p. III-102-IV-103. In B. Korber, C. L. Kuiken, B. Foley, B. Hahn, F. McCutchan, J. W. Mellors, and J. Sodroski (ed.), Human retroviruses and AIDS. Los Alamos National Laboratories, Los Alamos, N.Mex.). In another embodiment, the amino acids corresponding to amino acid numbers 234 and 276 are glycosylated.

Methods of making epitope-scaffolds are known in the art and disclosed, for example, by Correia et al. *Journal of Molecular Biology* 405, 284 (2011), Correia et al. *Structure* 18, 1116 (2010), Ofek et al. Proc *Natl Acad Sci USA* 107, 17780 (2010), McLellan et al. *J Mol Biol* 409, 853 (2011), Azoitei et al. *Science* 334, 373 (2011) and in US2010/0068217. Briefly, information obtained from the crystallographic analysis disclosed herein is used to design epitope-scaffolds that mimic the 8ANC195 epitope on the HIV-1 envelope spike. First, computational methods are utilized to identify non-HIV scaffold proteins capable of supporting the discontinuous epitope identified herein. Epitope-scaffolds are then designed and produced, and their immunological properties are characterized. For example, in the method of Azoitei et al., the Protein Data Bank (www.pdb.org) is searched for suitable scaffolds for the discontinuous epitope, for example by using an algorithm such as Multigraft Match. An algorithm such as Multigraft Design disclosed by Azoitei et al. is used for scaffold design in which regions of the scaffold are deleted and new segments are built to connect the epitope to the scaffold. Candidate epitope-scaffolds may be expressed in a host cell and purified, and tested for binding to 8ANC195 or another antibody that binds to the epitope recognized by 8ANC195.

The invention also includes isolated nucleic acid sequences encoding part or all of the light and heavy chains of the described inventive antibodies, and fragments thereof. Due to redundancy of the genetic code, variants of these sequences will exist that encode the same amino acid sequences. In one embodiment, the present invention provides an isolated nucleic acid encoding a polypeptide having the sequence of any one of SEQ ID Nos:1-33. In another embodiment, the isolated nucleic acid encodes an antibody comprising a heavy chain comprising the sequence of any one of SEQ ID Nos: 1-18 and a light chain comprising the sequence of any one of SEQ ID Nos:19-33.

The invention also includes isolated nucleic acid sequences that encode the antigen comprising the epitope-scaffold of the invention.

The terms "nucleic acid" and "polynucleotide" are used interchangeably herein to refer to single-stranded or double-stranded RNA, DNA, or mixed polymers. Polynucleotides can include genomic sequences, extra-genomic and plasmid sequences, and smaller engineered gene segments that express, or can be adapted to express polypeptides.

An "isolated nucleic acid" is a nucleic acid that is substantially separated from other genome DNA sequences as well as proteins or complexes such as ribosomes and polymerases, which naturally accompany a native sequence. The term encompasses a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Accordingly, this refers to the nucleic acid as originally isolated and does not exclude genes or sequences later added to the isolated nucleic acid by the hand of man.

A polynucleotide "variant," as the term is used herein, is a polynucleotide that typically differs from a polynucleotide specifically disclosed herein in one or more substitutions, deletions, additions and/or insertions. Such variants can be naturally occurring or can be synthetically generated, for example, by modifying one or more of the polynucleotide sequences of the invention and evaluating one or more biological activities of the encoded polypeptide as described herein and/or using any of a number of techniques well known in the art.

Modifications can be made in the structure of the polynucleotides of the described invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art typically will change one or more of the codons of the encoding DNA sequence.

Typically, polynucleotide variants contain one or more substitutions, additions, deletions and/or insertions, such that the immunogenic binding properties of the polypeptide encoded by the variant polynucleotide is not substantially diminished relative to a polypeptide encoded by a polynucleotide sequence specifically set forth herein.

In some embodiments, the polypeptide encoded by the polynucleotide variant or fragment has the same binding specificity (i.e., specifically or preferentially binds to the same epitope or HIV strain) as the polypeptide encoded by the native polynucleotide. In some embodiments, the described polynucleotides, polynucleotide variants, fragments and hybridizing sequences, encode polypeptides that have a level of binding activity of at least about 50%, at least about 70%, and at least about 90% of that for a polypeptide sequence specifically set forth herein.

The polynucleotides of the described invention, or fragments thereof, regardless of the length of the coding sequence itself, can be combined with other DNA sequences, such as promoters, polyadenylation signals, additional restriction enzyme sites, multiple cloning sites, other coding segments, and the like, such that their overall length can vary considerably. A nucleic acid fragment of almost any length is employed. For example, illustrative polynucleotide segments with total lengths of about 10000, about 5000, about 3000, about 2000, about 1000, about 500, about 200, about 100, about 50 base pairs in length, and the like, (including all intermediate lengths) are included in many implementations of this invention.

Further included within the scope of the invention are vectors such as expression vectors, comprising a nucleic acid sequence according to the invention. Cells transformed with such vectors also are included within the scope of the invention.

The present invention also provides vectors and host cells comprising a nucleic acid of the invention, as well as recombinant techniques for the production of a polypeptide of the invention. Vectors of the invention include those capable of replication in any type of cell or organism, including, for example, plasmids, phage, cosmids, and mini chromosomes. In some embodiments, vectors comprising a polynucleotide of the described invention are vectors suitable for propagation or replication of the polynucleotide, or vectors suitable for expressing a polypeptide of the described invention. Such vectors are known in the art and commercially available.

"Vector" includes shuttle and expression vectors. Typically, the plasmid construct also will include an origin of replication (for example, the ColE1 origin of replication) and a selectable marker (for example, ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells.

As used herein, the term "cell" can be any cell, including, but not limited to, that of a eukaryotic, multicellular species (for example, as opposed to a unicellular yeast cell), such as, but not limited to, a mammalian cell or a human cell. A cell can be present as a single entity, or can be part of a larger collection of cells. Such a "larger collection of cells" can comprise, for example, a cell culture (either mixed or pure), a tissue (for example, endothelial, epithelial, mucosa or other tissue), an organ (for example, lung, liver, muscle and other organs), an organ system (for example, circulatory system, respiratory system, gastrointestinal system, urinary system, nervous system, integumentary system or other organ system), or an organism (e.g., a bird, mammal, or the like).

Polynucleotides of the invention may synthesized, whole or in parts that then are combined, and inserted into a vector using routine molecular and cell biology techniques, including, for example, subcloning the polynucleotide into a linearized vector using appropriate restriction sites and restriction enzymes. Polynucleotides of the described invention are amplified by polymerase chain reaction using oligonucleotide primers complementary to each strand of the polynucleotide. These primers also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the invention, the nucleotide sequences encoding the polypeptide, or functional equivalents, may be inserted into an appropriate expression vector, i.e., a vector that contains the necessary elements for the transcription and translation of the inserted coding sequence. Methods well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

According to another embodiment, the present invention provides methods for the preparation and administration of an HIV antibody composition that is suitable for administration to a human or non-human primate patient having HIV infection, or at risk of HIV infection, in an amount and according to a schedule sufficient to induce a protective immune response against HIV, or reduction of the HIV virus, in a human.

According to another embodiment, the present invention provides methods for the preparation and administration of an HIV antigen composition that is suitable for administration to a human or non-human primate patient having HIV infection, or at risk of HIV infection, in an amount and according to a schedule sufficient to induce a protective immune response against HIV, or reduction of the HIV virus, in a human.

According to another embodiment, the present invention provides a composition comprising at least one antibody or polypeptide of the invention and a pharmaceutically acceptable carrier. The composition may include a plurality of the antibodies having the characteristics described herein in any combination and can further include antibodies neutralizing to HIV as are known in the art. According to another embodiment, the present invention provides a composition comprising at least one antigen of the invention and a pharmaceutically acceptable carrier, can further include antibodies neutralizing to HIV as are known in the art, and can further include an adjuvant.

It is to be understood that compositions can be a single or a combination of antibodies disclosed herein, which can be the same or different, in order to prophylactically or therapeutically treat the progression of various subtypes of HIV infection after vaccination. Such combinations can be selected according to the desired immunity. When an antibody or antigen is administered to an animal or a human, it can be combined with one or more pharmaceutically acceptable carriers, excipients or adjuvants as are known to one of ordinary skilled in the art. The composition can further include broadly neutralizing antibodies known in the art, including but not limited to, VRC01, b12, anti-V3 loop, CD4bs, and CD4i antibodies as well as PG9/PG16-like antibodies.

Further, with respect to determining the effective level in a patient for treatment of HIV, in particular, suitable animal models are available and have been widely implemented for evaluating the in vivo efficacy against HIV of various gene therapy protocols (Sarver et al. (1993b), supra). These models include mice, monkeys and cats. Even though these animals are not naturally susceptible to HIV disease, chimeric mice models (for example, SCID, bg/nu/xid, NOD/SCID, SCID-hu, immunocompetent SCID-hu, bone marrow-ablated BALB/c) reconstituted with human peripheral blood mononuclear cells (PBMCs), lymph nodes, fetal liver/thymus or other tissues can be infected with lentiviral vector or HIV, and employed as models for HIV pathogenesis. Similarly, the simian immune deficiency virus (SIV)/monkey model can be employed, as can the feline immune deficiency virus (FIV)/cat model. The pharmaceutical composition can contain other pharmaceuticals, in conjunction with a vector according to the invention, when used to therapeutically treat AIDS. These other pharmaceuticals can be used in their traditional fashion (i.e., as agents to treat HIV infection).

According to another embodiment, the present invention provides an antibody-based pharmaceutical composition comprising an effective amount of an isolated antibody of the invention, or an affinity matured version, which provides a prophylactic or therapeutic treatment choice to reduce infection of the HIV virus. According to another embodiment, the present invention provides an antigen-based pharmaceutical composition comprising an effective amount of an isolated antigen of the invention, which provides a prophylactic or therapeutic treatment choice to reduce infection of the HIV virus. The pharmaceutical compositions of the present invention may be formulated by any number of strategies known in the art (e.g., see McGoff and Scher, 2000, Solution Formulation of Proteins/Peptides: In McNally, E. J., ed. Protein Formulation and Delivery. New York, N.Y.: Marcel Dekker; pp. 139-158; Akers and Defilippis, 2000, Peptides and Proteins as Parenteral Solutions. In: Pharmaceutical Formulation Development of Peptides and Proteins. Philadelphia, Pa.: Talyor and Francis; pp. 145-177; Akers, et al., 2002, Pharm. Biotechnol. 14:47-127). A pharmaceutically acceptable composition suitable for patient administration will contain an effective amount of the antibody in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. The amount of an excipient that is useful in the pharmaceutical composition or formulation of this invention is an amount that serves to uniformly distribute the antibody throughout the composition so that it can be uniformly dispersed when it is to be delivered to a subject in need thereof. It may serve to dilute the antibody or antigen to a concentration which provides the desired beneficial palliative or curative results while at the same time minimizing any adverse side effects that might occur from too high a concentration. It may also have a preservative effect. Thus, for an active ingredient having a high physiological activity, more of the excipient will be employed. On the other hand, for any active ingredient(s) that exhibit a lower physiological activity, a lesser quantity of the excipient will be employed. Compositions comprising an antigen of the invention may further comprise one or more adjuvants.

The above described antibodies and antibody compositions, comprising at least one or a combination of the antibodies described herein, can be administered for the prophylactic and therapeutic treatment of HIV viral infection.

The above described antigens and antigen compositions, comprising at least one or a combination of the antigens described herein, can be administered for the prophylactic and therapeutic treatment of HIV viral infection.

The present invention also provides kits useful in performing diagnostic and prognostic assays using the antibodies, polypeptides and nucleic acids of the present invention. Kits of the present invention include a suitable container comprising an HIV antibody, an antigen, a polypeptide or a nucleic acid of the invention in either labeled or unlabeled form. In addition, when the antibody, antigen, polypeptide or nucleic acid is supplied in a labeled form suitable for an indirect binding assay, the kit further includes reagents for performing the appropriate indirect assay. For example, the kit may include one or more suitable containers including enzyme substrates or derivatizing agents, depending on the nature of the label. Control samples and/or instructions may also be included. The present invention also provides kits for detecting the presence of the HIV antibodies or the nucleotide sequence of the HIV antibody of the present invention in a biological sample by PCR or mass spectrometry.

"Label" as used herein refers to a detectable compound or composition that is conjugated directly or indirectly to the antibody so as to generate a "labeled" antibody. A label can also be conjugated to a polypeptide and/or a nucleic acid sequence disclosed herein. The label can be detectable by itself (for example, radioisotope labels or fluorescent labels) or, in the case of an enzymatic label, can catalyze chemical alteration of a substrate compound or composition that is detectable. Antibodies and polypeptides of the described invention also can be modified to include an epitope tag or label, for example, for use in purification or diagnostic applications. Suitable detection means include the use of labels such as, but not limited to, radionucleotides, enzymes, coenzymes, fluorescers, chemiluminescers, chromogens, enzyme substrates or co-factors, enzyme inhibitors, prosthetic group complexes, free radicals, particles, dyes, and the like.

Methods for reducing an increase in HIV virus titer, virus replication, virus proliferation or an amount of an HIV viral protein in a subject are further provided. According to another aspect, a method includes administering to the subject an amount of an HIV antibody of the invention effective to reduce an increase in HIV titer, virus replication or an amount of an HIV protein of one or more HIV strains or isolates in the subject. According to another aspect, a method includes administering to the subject an amount of an HIV antigen of the invention effective to reduce an increase in HIV titer, virus replication or an amount of an HIV protein of one or more HIV strains or isolates in the subject.

According to another embodiment, the present invention provides a method of reducing viral replication or spread of HIV infection to additional host cells or tissues comprising contacting a mammalian cell with the antibody, or a portion thereof, which binds to the 8ANC195 antigenic epitope on gp120. According to another embodiment, the present invention provides a method of reducing viral replication or spread of HIV infection to additional host cells or tissues comprising contacting a mammalian cell with the antigen that mimics the 8ANC195 antigenic epitope on gp120.

According to another embodiment, the present invention provides a method for treating a mammal infected with a virus infection, such as, for example, HIV, comprising administering to said mammal a pharmaceutical composition comprising the HIV antibodies disclosed herein. According to one embodiment, the method for treating a mammal infected with HIV comprises administering to said mammal a pharmaceutical composition that comprises an antibody of the present invention, or a fragment thereof. The compositions of the invention can include more than one antibody having the characteristics disclosed (for example, a plurality or pool of antibodies). It also can include other HIV neutralizing antibodies as are known in the art, for example, but not limited to, VRC01, PG9 and b12.

Passive immunization has proven to be an effective and safe strategy for the prevention and treatment of viral diseases. (See, for example, Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999). Passive immunization using human monoclonal antibodies provides an immediate treatment strategy for emergency prophylaxis and treatment of HIV.

According to another embodiment, the present invention provides a method of inducing an HIV antigen-specific immune response in a mammal infected with HIV or at risk of infection with HIV comprising administering to the mammal a pharmaceutical composition comprising the antigen of the invention.

According to another embodiment, the present invention provides a method of inducing an HIV antigen-specific immune response in a mammal infected with HIV or at risk of infection with HIV comprising administering to the mammal a pharmaceutical composition comprising a nucleic acid encoding the antigen of the invention.

Subjects at risk for HIV-related diseases or disorders include patients who have come into contact with an infected person or who have been exposed to HIV in some other way. Administration of a prophylactic agent can occur prior to the manifestation of symptoms characteristic of HIV-related disease or disorder, such that a disease or disorder is prevented or, alternatively, delayed in its progression.

For in vivo treatment of human and non-human patients, the patient is administered or provided a pharmaceutical formulation including an HIV antibody or antigen of the invention. When used for in vivo therapy, the antibodies and antigens of the invention are administered to the patient in therapeutically effective amounts (i.e., amounts that eliminate or reduce the patient's viral burden). The antibodies or antigens are administered to a human patient, in accord with known methods, such as intravenous administration, for example, as a bolus or by continuous infusion over a period of time, by intramuscular, intraperitoneal, intracerobrospinal, subcutaneous, intra-articular, intrasynovial, intrathecal, oral, topical, or inhalation routes. The antibodies can be administered parenterally, when possible, at the target cell site, or intravenously. In some embodiments, antibody is administered by intravenous or subcutaneous administration. Therapeutic compositions of the invention may be administered to a patient or subject systemically, parenterally, or locally. The above parameters for assessing successful treatment and improvement in the disease are readily measurable by routine procedures familiar to a physician.

For parenteral administration, the antibodies or antigens may be formulated in a unit dosage injectable form (solution, suspension, emulsion) in association with a pharmaceutically acceptable, parenteral vehicle. Examples of such vehicles include, but are not limited, water, saline, Ringer's solution, dextrose solution, and 5% human serum albumin. Nonaqueous vehicles include, but are not limited to, fixed oils and ethyl oleate. Liposomes can be used as carriers. The vehicle may contain minor amounts of additives such as substances that enhance isotonicity and chemical stability, such as, for example, buffers and preservatives. The antibodies can be formulated in such vehicles at concentrations of about 1 mg/ml to 10 mg/ml.

The dose and dosage regimen depends upon a variety of factors readily determined by a physician, such as the nature of the infection, for example, its therapeutic index, the patient, and the patient's history. Generally, a therapeutically effective amount of an antibody or antigen is administered to a patient. In some embodiments, the amount of antibody or antigen administered is in the range of about 0.1 mg/kg to about 50 mg/kg of patient body weight. Depending on the type and severity of the infection, about 0.1 mg/kg to about 50 mg/kg body weight (for example, about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art. The above parameters for assessing successful treatment and improvement in the disease are readily measurable by routine procedures familiar to a physician.

A dosage regimen for administration of an antigen to a patient may be a suitable immunization regimen, including for example at least three separate inoculations. The second inoculation may be administered more than at least two weeks after the first inoculation. The third inoculation may be administered at least several months after the second administration.

Other therapeutic regimens may be combined with the administration of the HIV antibody or antigen of the present invention. The combined administration includes co-administration, using separate formulations or a single pharmaceutical formulation, and consecutive administration in either order, wherein preferably there is a time period while both (or all) active agents simultaneously exert their biological activities. Such combined therapy can result in a synergistic therapeutic effect. The above parameters for assessing successful treatment and improvement in the disease are readily measurable by routine procedures familiar to a physician.

The terms "treating" or "treatment" or "alleviation" are used interchangeably and refer to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody or antigen according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to treat a disease or disorder in a subject or mammal.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone; amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, TWEEN; polyethylene glycol (PEG), and PLURONICS.

According to another embodiment, the present invention provides diagnostic methods. Diagnostic methods generally involve contacting a biological sample obtained from a patient, such as, for example, blood, serum, saliva, urine, sputum, a cell swab sample, or a tissue biopsy, with an HIV antibody and determining whether the antibody preferentially binds to the sample as compared to a control sample or predetermined cut-off value, thereby indicating the presence of the HIV virus.

According to another embodiment, the present invention provides methods to detect the presence of the HIV antibodies of the present invention in a biological sample from a patient. Detection methods generally involve obtaining a biological sample from a patient, such as, for example, blood, serum, saliva, urine, sputum, a cell swab sample, or a tissue biopsy and isolating HIV antibodies or fragments thereof, or the nucleic acids that encode an HIV antibody, and assaying for the presence of an HIV antibody in the biological sample. Also, the present invention provides methods to detect the nucleotide sequence of an HIV antibody in a cell. The nucleotide sequence of an HIV antibody may also be detected using the primers disclosed herein. The presence of the HIV antibody in a biological sample from a patient may be determined utilizing known recombinant techniques and/or the use of a mass spectrometer.

According to another embodiment, the present invention provides methods for detecting or isolating an HIV-1 binding antibody in a subject comprising obtaining a biological sample from the subject, contacting said sample with the antigen of the invention, and conducting an assay to detect or isolate an HIV-1 binding antibody.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Example 1

This example describes materials and methods used in EXAMPLES 2-5 below.

Protein Expression and Purification

The antibodies used in this study were produced and purified as in previously-described studies (Diskin et al., Science 334, 1289 (2011).) Briefly, 8ANC195, 3BNC60 and chimeric antibody (mature HC/various LC; γ/κ combinations of newly isolated 8ANC195 variants) IgGs were expressed by transiently transfecting HEK293-6E cells with vectors containing the appropriate heavy and light chain genes. Secreted IgGs were purified from cell supernatants using protein A affinity chromatography (GE Healthcare). For neutralization assays, IgGs were diluted to 1 mg/mL stocks in 20 mM Tris pH 8.0, 150 mM sodium chloride (TBS buffer). 8ANC195 Fab was expressed with a 6×-His tag on the C-terminus of $C_H1$ as described for IgGs and purified using $Ni^{2+}$-NTA affinity chromatography (GE Healthcare) and Superdex 200 16/60 size exclusion chromatography (GE Healthcare).

A truncated gp120 from the HIV-1 strain 93TH057 containing mutations $Asn88Gln_{gp120}$, $Asn289Gln_{gp120}$, $Asn334Gln_{gp120}$, $Asn392Gln_{gp120}$, $Asn448Gln_{gp120}$ was produced by transiently transfecting HEK293-S (GnTI−/−) cells adapted for growth in suspension by the Caltech Protein Expression Center with a pTT5 vector encoding His-tagged gp120. Secreted gp120 was captured on $Ni^{2+}$-NTA resin (GE Healthcare) and further purified using Superdex 200 16/60 size exclusion chromatography (GE Healthcare).

Soluble CD4 domains 1 and 2 (sCD4) and $sCD4_{K75T}$ were produced as described previously (Diskin et al. Nat Struct Mol Biol 17, 608 (2010)). Briefly, the pACgp67b vector encoding 6×-His-tagged sCD4 or $sCD4_{K75T}$ (residues 1-186 of mature CD4) was used to make infectious baculovirus particles using BaculoGold (BD Biosynthesis). Protein was expressed in Hi5 cells, captured on a $Ni^{2+}$-NTA column (GE Healthcare) and further purified using Superdex 200 16/60 size exclusion chromatography (GE Healthcare). To remove an N-linked glycan introduced by mutation in $sCD4_{K75T}$, the protein was treated with Endoglycosidase H (New England Biolabs) for 16 hours at 25° C. and then purified by Superdex 200 16/60 size exclusion chromatography (GE Healthcare).

For complex crystallization trials, purified 8ANC195 Fab, 93TH057 gp120 and EndoH-treated $sCD4_{K75T}$ were incubated at a 1:1:1 molar ratio for 2 hours at 25° C. The complex was purified by Superdex 200 10/300 size exclusion chromatography (GE Healthcare) and the peak corresponding to 8ANC195 Fab/gp120/$sCD4_{K75T}$ complex concentrated to 16 mg/mL in TBS buffer. For crystallization of 8ANC195 Fab alone, the protein was concentrated to 20 mg/mL in TBS buffer.

Purified BG505 SOSIP trimers (Julien et al., PLoS pathogens 9, e1003342 (2013); Lyumkis et al., Science 342, 1484 (2013); Sanders et al., PLoS pathogens 9, e1003618 (2013)) for EM studies were the gift of Dr. John P. Moore (Weill Cornell Medical College).

Crystallization

Crystallization conditions were screened using vapor diffusion in sitting drops set using a Mosquito® crystallization robot (TTP labs) in a final volume of 200 nL per drop (1:1 protein to reservoir ratio) utilizing commercially available crystallization screens (Hampton Research, Microlytic). Initial crystallization hits for 8ANC195 Fab and for 8ANC195 Fab/93TH057 gp120/$sCD4_{K75T}$ complex were identified using the MCSG-1 (Microlytic) and PEGRx (Hampton) screens and then manually optimized. Crystals of 8ANC195 Fab (space group $P4_12_12$, a=66.5 Å, b=66.5 Å, c=219.0 Å; one molecule per asymmetric unit) were obtained upon mixing a protein solution at 11 mg/mL with 0.1M Hepes pH 7, 20% PEG 6,000, 10 mM zinc chloride at 20° C. Crystals were briefly soaked in mother liquor solution supplemented with 20% ethylene glycol before flash cooling in liquid nitrogen. Crystals of the 8ANC195 Fab/93TH057 gp120/$sCD4_{K75T}$ complex (space group $P2_12_12_1$, a=66.5 Å, b=132.5 Å, c=142.8 Å; one molecule per asymmetric unit) were obtained upon mixing a protein solution at 16 mg/mL with 14% polyethylene glycol 3,350, 0.1 M HEPES pH 7.3, 2% benzamidine HCl at 20° C. Crystals were briefly soaked in mother liquor solution supplemented with 30% ethylene glycol before flash cooling in liquid nitrogen.

Crystallographic Data Collection, Structure Solution and Refinement

X-ray diffraction data for 8ANC195 Fab crystals were collected at the Argonne National Laboratory Advanced Photon Source (APS) beamline 23-ID-D using a MAR 300 CCD detector. X-ray diffraction data for 8ANC195 Fab/93TH057 gp120/$sCD4_{K75T}$ complex crystals were collected at the Stanford Synchrotron Radiation Lightsource (SSRL) beamline 12-2 using a Pilatus 6M pixel detector (Dectris). The data were indexed, integrated and scaled using XDS (Kabsch, Acta Crystallogr D Biol Crystallogr 66, 133 (2010)).

The 8ANC195 Fab structure was solved by molecular replacement using Phenix (Adams et al., Acta Crystallogr D Biol Crystallogr 66, 213 (2010)) and the $V_HV_L$ and $C_H1 C_L$ domains of NIH45-46 Fab (PDB code 3U7W) lacking all CDR loops as two separate search models. The model was then refined to 2.13 Å resolution using an iterative approach involving refinement and verification of model accuracy with simulated annealing composite omit maps using the Phenix crystallography package, and manually fitting models into electron density maps using Coot (Emsley et al., Acta Crystallogr D Biol Crystallogr 60, 2126 (2004). The final model ($R_{work}$=21.4%; $R_{free}$=25.7%) includes 3,279 protein atoms and 127 water molecules as shown in Table 1.

TABLE 1

| | 8ANC195 Fab/gp120/ sCD4 complex | 8ANC195 Fab |
|---|---|---|
| Data collection | | |
| Resolution range (Å) | 39.22-3.0 (3.22-3.0) | 29.73-2.1 (2.21-2.1) |
| Space group | $P 2_1 2_1 2_1$ | $P 4_1 2_1 2$ |

TABLE 1-continued

|  | 8ANC195 Fab/gp120/sCD4 complex | 8ANC195 Fab |
|---|---|---|
| Cell dimensions | | |
| a, b, c (Å) | 66.53, 132.49, 142.77 | 66.48, 66.48, 219.03 |
| α, β, γ (°) | 90, 90, 90 | 90, 90, 90 |
| Total refections | 229212 (12539) | 239217 (24708) |
| Unique reflections | 36730 (3064) | 28097 (2788) |
| Multiplicity | 6.2 (6.3) | 8.4 (8.9) |
| Completeness (%) | 97.65 (99.80) | 98.92 (91.00) |
| Mean I/σ(I) | 7.86 (2.1) | 11.90 (3.16) |
| Wilson B-factor | 61.95 | 32.47 |
| $R_{merge}$ | 0.1747 (0.765) | 0.1225 (0.5802) |
| $CC_{1/2}$ | 0.996 (0.854) | 0.996 (0.876) |
| CC* | 0.999 (0.960) | 0.999 (0.966) |
| Refinement | | |
| $R_{work}/R_{free}$ | 0.2655/0.3149 | 0.2431/0.2772 |
| Number of atoms | 7272 | 3311 |
| Protein | 6881 | 3311 |
| Ligands | 391 | 0 |
| Water | 0 | 0 |
| Protein residues | 939 | 437 |
| RMS (bonds) | 0.023 | 0.008 |
| RMS (angles) | 1.33 | 1.17 |
| Clashscore | 22.76 | 12.43 |
| Average B-factor | 81.5 | 36.5 |
| Protein | 81 | 36.5 |
| Ligands | 89 | — |
| Water | — | — |

Statistics for the highest-resolution shelf are shown in parentheses.

96.75%, 2.78% and 0.0% of the residues were in the favored, allowed and disallowed regions, respectively, of the Ramachandran plot. Disordered residues that were not included in the model include residues 146-153, 233-238 and the 6x-His tag of the 8ANC195 heavy chain, and residues 214-215 of the light chain.

The 8ANC195 Fab/93TH057 gp120/sCD4$_{K75T}$ complex structure was solved by molecular replacement using Phaser (Adams et al., Acta Crystallogr D Biol Crystallogr 66, 213 (2010)) and the $V_H V_L$ and $C_H 1 C_L$ domains of 8ANC195 (lacking all CDR loops), 93TH057 gp120 (taken from PDB code 3U7Y), and sCD4 (taken from PDB code 3LQA) as separate search models. The complex structure was refined to 3.0 Å resolution as described for the Fab structure. In addition to considering I/σ$_I$ and completeness of the highest resolution shell (2.1% and 99.9%, respectively), $CC_{1/2}$ statistic (Karplus et al., Science 336, 1030 (2012)) (correlation coefficient between two random halves of the data set where $CC_{1/2}$>10%) was used to determine the high-resolution cutoff for the data. Phenix was used to compute $CC_{1/2}$ (85.4% for the highest resolution shell and 99.8% for the entire data set), supporting our high-resolution cutoff determination.

The final model ($R_{work}$=23.4%; $R_{free}$=28.6%) includes x protein atoms and y atoms of carbohydrates (Table SI). 96.2%, 3.8% and 0.0°) of the residues were in the favored, allowed and disallowed regions, respectively, of the Ramachandran plot. Disordered residues that were not included in the model include residues 146-153, 206-208, 233-238 and the 6x-His tag of the 8ANC195 heavy chain, residues 213-215 of the light chain, residues 125-197 (V1/V2 substitution). 302-324 (V3 substitution), residues 397-409 (a total of 6 residues from V4). residues 492-494 and the 6x-His tag of 93TH057 gp120 and residues 106-111, 154-155, 177-186 of sCD4$_{K75T}$.

Buried surface areas were calculated using PDBePISA (Krissinel et al., Journal of molecular biology 372, 774 (2007)) and a 1.4 Å probe. Superimposition calculations were done and molecular representations were generated using PyMol (Schrödinger (The PyMOL Molecular Graphics System, 2011). Pairwise Cα alignments were performed using PDBeFold (Krissinel et al., Acta Crystallogr D Biol Crystallogr 60, 2256 (2004)).

ELISAs

High-binding 96-well ELISA plates (Costar) were coated overnight with 5 μg/well of purified gp120 in 100 mM sodium carbonate pH 9.6. After washing with TBS containing 0.05% Tween 20, the plates were blocked for 2 h with 1% BSA, 0.05% Tween-TBS (blocking buffer) and then incubated for 2 h with 8ANC195 IgG (1 μg/mL) mixed with 1:2 serially diluted solutions of potential antibody competitors (sCD4, J3 VHH, 3BNC60 Fab, NIH45-46 Fab) in blocking buffer (competitor concentration range from 5 to 320 μg/mL). After washing with TBS containing 0.05% Tween 20, the plates were incubated with HRP-conjugated goat anti-human IgG antibodies (Jackson ImmunoReseach) (at 0.8 μg/ml in blocking buffer) for 1 hour. The ELISAs were developed by addition of HRP chromogenic substrate (TMB solution, BioLegend) and the color development stopped by addition of 10% sulfuric acid. Experiments were performed in duplicate.

Surface Plasmon Resonance

Experiments were performed using a Biacore T100 (Biacore) using a standard single-cycle kinetics method. YU-2 and 93TH057 gp120 proteins were primary amine-coupled on CMS chips (Biacore) at a coupling density of 1,000 RUs and one flow cell was mock coupled using HBS-EP+ buffer. 8ANC195 and chimeric IgGs were injected over flow cells at increasing concentrations (62.5 to 1,000 nM), at flow rates of 20 μl/min with 5 consecutive cycles of 2 min association/1 min dissociation and a final 10 min dissociation phase. Flow cells were regenerated with 3 pulses of 10 mM glycine pH 2.5. Apparent binding constants ($K_D$ (M)) were calculated from single-cycle kinetic analyses after subtraction of backgrounds using a 1:1 binding model without a bulk reflective index (RI) correction (Biacore T100 Evaluation software). Binding constants for bivalent IgGs are referred to as "apparent" affinities to emphasize that the $K_D$ values include potential avidity effects.

Neutralization Assays

A TZM-bl/pseudovirus neutralization assay was used to evaluate the neutralization potencies of the antibodies as described (Montefiori, Current protocols in immunology edited by John E. Coligan et al., Chapter 12, Unit 12 11 (2005)). Pseudoviruses were generated by cotransfection of HEK 293T cells with an Env expression plasmid and a replication-defective backbone plasmid. Neutralization was determined by measuring the reduction in luciferase reporter gene expression in the presence of antibody following a single round of pseudovirus infection in TZM-bl cells. Nonlinear regression analysis was used to calculate the concentrations at which half-maximal inhibition was observed ($IC_{50}$ values).

Negative-Stain EM

The BG505 SOSIP.664/8ANC195 Fab complex and grids were prepared as described previously (Kong et al., Nat Struct Mol Biol 20, 796 (2013). The data were collected on an FEI Tecnai T12 electron microscope coupled with a Tietz TemCam-F416 4 k×4 k CMOS camera using the LEGINON interface. Images were collected in 10° increments from 0° to −40° using a defocus range of 0.6-0.9 μm at a magnification of 52,000×, resulting in a pixel size of 2.05 Å at the specimen plane. Particles were selected using DogPicker (Voss et al., Journal of structural biology 166, 205 (2009)) within the Appion software package (Lander et al., Journal of structural biology 166, 95 (2009)), and sorted from reference-free 2D class averages using the SPARX package (Penczek et al., *Ultramicroscopy* 40, 33 (1992). An initial model was generated by common lines from class averages using the EMAN2 package (Tang et al., *Journal of structural biology* 157, 38 (2007) and was refined using 11,637 unbinned particles. The refinement was carried out using the SPARX package (Penczek et al., *Ultramicroscopy* 53, 251 (1994)) with C3 symmetry applied. The resulting resolution at a 0.5 Fourier Shell Correlation (FSC) cut-off was 18.7 Å (FIGS. 6A,B).

Human Samples

Human samples were collected after signed informed consent in accordance with Institutional Review Board (IRB)-reviewed protocols by all participating institutions. Patient 8 was selected from a cohort of elite controllers that were followed at the Ragon Institute in Boston.

Isolation of 8ANC195 Variants

Single Cell clonal variants of 8ANC195 were isolated by 2CC core-specific single cell sorting, followed by reverse transcription and immunoglobulin gene amplification as described previously (Scheid et al., *Science* 333, 1633 (2011)). Immunoglobulin genes were cloned into heavy and light chain expression vectors and co-transfected for IgG production as described previously (Tiller et al., *Journal of immunological methods* 329, 112 (2008)).

IgG+ CD19+ memory B cells were bulk sorted on a FACS AriaIII cell sorter. Bulk mRNA was extracted using TRIzol (Invitrogen) and reverse transcribed as previously described (Scheid et al., *Science* 333, 1633 (2011)). 8ANC195-related heavy and light chain genes were PCR amplified using the following clone-specific primers:

```
For heavy chain amplification:
                                       (SEQ ID NO: 50)
5' GGTGTACATTCTCAGATACACCTCGTACAA 3'
and
                                       (SEQ ID NO: 51)
5' CAGGTGTCCAGTCTCAGATACA 3' as forward primers and (SEQ ID NO: 57)
5' GCGGAGACGGAGATGAGGGTT 3' as a reverse primer.

For light chain amplification:
                                       (SEQ ID NO: 52)
5' GACATCCAGATGACCCAGTCTCCTTCCACCCTGTCTGCATCTATAGGT
3'
and (SEQ ID NO: 53)
5' GACATCCAGATGACCCAGTCTCCTTCCACCCTGTCTGCATCT 3' as
forward and (SEQ ID NO: 58)
5' GTTTCACCTCAACTTTAGTCCCTT 3' as well as (SEQ ID NO: 59)
5' GTTTCACCTCAACTTTAGTCCCTTGGCCGAAGGTC 3' as
reverse primers.
```

Amplification products were gel purified and cloned into TOPO TA sequencing vectors (Invitrogen) and expression vectors as described previously (T. Tiller et al., *Journal of immunological methods* 329, 112 (2008)).

Phylogenetic Tree and Alignment Assembly.

Phylogenetic trees were assembled using Geneious Neighbor-Joining Tree Software. Sequence Alignments were performed using DNA Star Clustal W alignment software.

Computational Analysis.

The program AntibodyDatabase (West, Jr. et al., *Proceedings of the National Academy of Sciences of the United States of America* 110, 10598 (2013)) was used to analyze 8ANC195 neutralization panel data from Scheid et al., *Science* 333, 1633 (2011) and Chuang et al., *Journal of virology* 87, 10047 (2013). This method attempts to model the variation in neutralization potency across strains based on a sum of terms ("rules") corresponding to specific residues or potential N-linked glycosylation site (PNGS) positions. With the free residual option deselected, the analysis finds a rule corresponding to ~3-fold better 8ANC195 neutralization for strains with $Glu632_{gp41}$. This correlation appears to hold across clades based on neutralization data for strains having the most favorable glycosylation pattern (PNGS at $234_{gp120}$ and $276_{gp120}$, and not at $230_{gp120}$) (22). For all clades, the residue at $632_{gp41}$ versus geometric mean $IC_{50}$s for 8ANC195 on strains with the most favorable glycosylation pattern was as follows: Glu, 0.43 μg/mL (n=53) versus Asp, 1.31 μg/mL (n=51). For separate clades, the correlations were Clade A: Glu, 0.47 μg/mL (n=3); Asp, 1.30 μg/mL (n=24); Clade B: Glu, 0.18 μg/mL (n=15); Asp, 0.72 μg/mL (n=6); Clade C: Glu, 0.32 μg/mL (n=2); Asp, 1.31 μg/mL (n=20).

Statistical Analysis of Neutralization Potencies of 8ANC195 Variants $IC_{50}$ values derived from neutralization assays with 8ANC195 and $\gamma52_{HC}/\kappa5_{LC}$ variant against 11 sensitive virus strains ($IC_{50}$<50) were analyzed by G-test for the relationship between the amino acid identity at position $636_{gp41}$ and the antibody $IC_{50}$. For each antibody the partition between "high" and "low" $IC_{50}$s was chosen such that approximately half of the strains had high $IC_{50}$s (0.8 μg/mL for 8ANC195, 0.1 μg/mL for $\gamma52_{HC}/\kappa5_{LC}$).

Example 2

Determination of the Crystal Structure of the Fab Fragment of 8ANC195 Alone and Complexed with HIV-1 gp120 Core and CD4 Domains 1-2 (sCD4)

To determine the epitope recognized by 8ANC195 and investigate its neutralization mechanism, crystal structures were solved of the Fab fragment of 8ANC195 alone and complexed with an HIV-1 Glade A/E 93TH057 gp120 core and CD4 domains 1-2 (sCD4) at 1.9 Å and 2.9 Å resolution, respectively (FIG. 16A,B; Table 1). Five PNGSs on the core gp120 were removed by mutation ($Asn88Gln_{gp120}$, $Asn289Gln_{gp120}$, $Asn334Gln_{gp120}$, $Asn392Gln_{gp120}$, $Asn448Gln_{gp120}$) to reduce glycan heterogeneity.

Figure 2A:
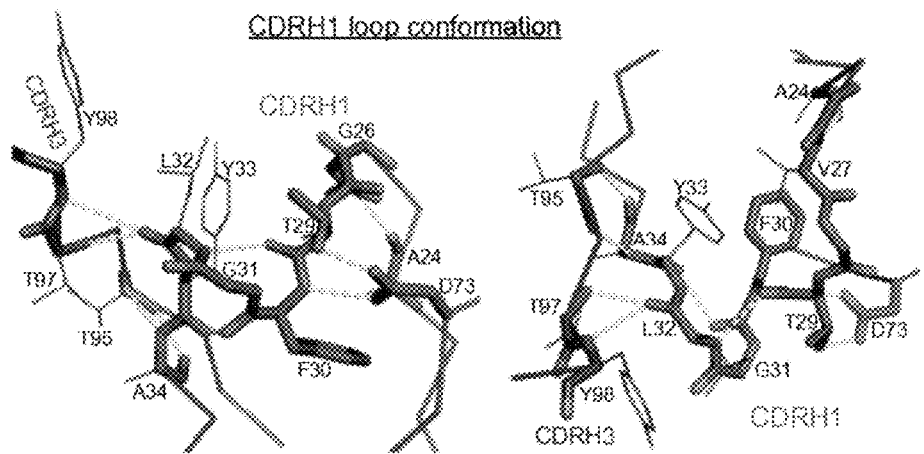
FIGS. 2A, 2B and 2C illustrates conformations of 8ANC195 CDRH1 and CDRH3 loops. (A) The hook-like conformation of CDRH1 is stabilized by burial of the hydrophobic Phe30HC side chain and hydrogen bonds within CDRH1 and with CDRH3 and FWR1 and FWR3 residues (Ala24HC and Asp73HC, respectively). (B) The complexed CDRH3 conformation consists of a protruding loop (residues 95HC-100HC) and a small β-sheet subdomain (residues 100dHC-100kHC) stabilized by multiple hydrogen bonds within CDRH3 as well as with CDRH1 and CDRL3. A hydrogen bond between Tyr92LC and Gly100cHC stabilized the bifurcation of CDRH3 into its two subdomains. CDRH1 and CDRH3 loop backbone atoms are shown as sticks and side chains of residues important for stabilizing the loop conformations are shown as sticks (involved in direct contacts) or lines (backbone involved in contacts) (other side chains Tyr98HC, Lys100HC and Trp100aHC, are shown for clarity). (C) Comparison of CDRH3 loops in 8ANC195 and other anti-HIV-1 bNAbs. CDRH3 residues corresponding to 8ANC195HC residues 90-105 of NIH45-46 (PDB 3U7Y), PG16 (PDB 4DQO), PGT121 (PDB 4FQC) and PGT128 (PDB 3TYG) are shown as Cα traces.
Figure 2B:
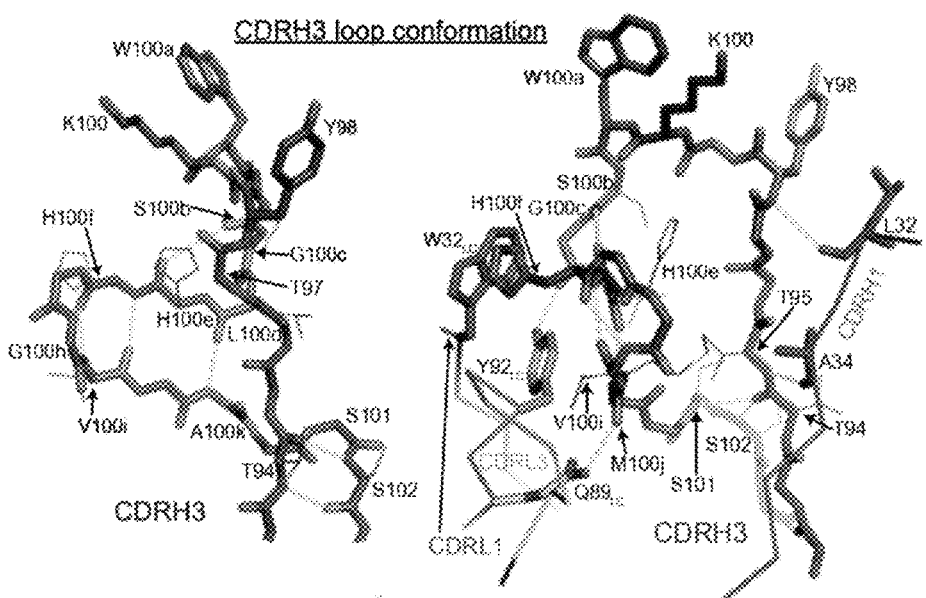
Figure 2C:
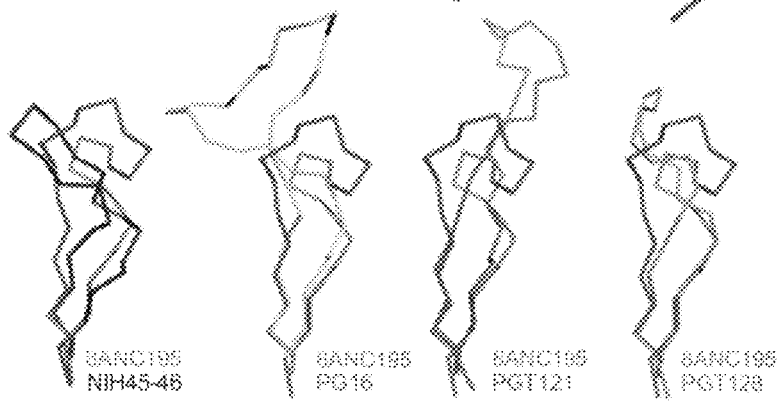

Comparison of 8ANC195 Fab in its free versus gp120-bound states revealed high structural similarity (RMSD=0.7 Å for 236 Cα atoms of $V_H$-$V_L$) except for a 3.5 Å displacement of the loop connecting strands D and E in HC FWR3 (FIG. 16A). The CDRH1 and CDRH3 loops were folded into hook-like tertiary structures in free and gp120-bound Fabs; therefore the conformations were not induced upon binding to gp120 (FIG. 16A and FIGS. 2A,B). The CDRH3 architecture differed from CDRH3s in other antibodies including anti-HIV-1 antibodies with long CDR loops (FIG. 2C). The CDRH1 loop conformation was stabilized by a hydrogen bond network among backbone atoms of CDRH1, burial of $Phe30_{HC}$, and hydrogen bonds with $Asp73_{HC}$ and $Thr104_{HC}$ (FIG. 2A). CDRH3 had a complex tertiary structure in which residues $102_{HC}$-$110_{HC}$ formed a loop protruding ~10 Å from the antibody surface, and residues $111_{HC}$-$118_{HC}$ formed a β-sheet subdomain that was stabilized by hydrophobic stacking between $His113_{HC}$ and $Trp33_{LC}$ and a hydrogen bond between Met117$_{HC}$ and Gln90$_{LC}$ (FIG. 2B). The side chain of Tyr92$_{LC}$ hydrogen bonded with the Gly110$_{HC}$ carbonyl oxygen, stabilizing a kink in the loop that formed the transition between these secondary structure elements (FIG. 2B).

Figure 3A:
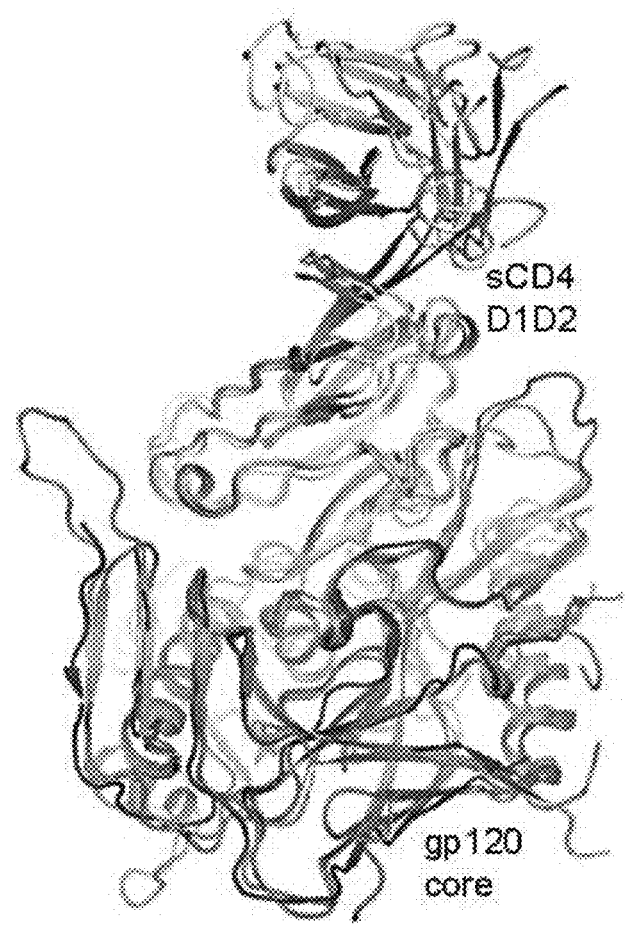
FIGS. 3A, 3B, 3C, 3D and 3E illustrates CD4 interactions with 8ANC195. (A) Superimposition of sCD4 D1D2/gp120 structures (ribbon diagrams) from complexes with 8ANC195, 17b (PDB 1GCI) and 21c PDB 3LQA). (B) Competition ELISA of 8ANC195 IgG binding to 93TH057 gp120 in the presence of increasing concentrations of potential competitors (sCD4, diamonds; J3 VHH, triangles; 3BNC60 Fab, squares; NIH45-46 Fab, circles). No competition was observed with small, single-Ig domain CD4-binding site ligands (sCD4, J3 VHH), but larger Fab fragments of CD4 binding site antibodies (3BNC60, NIH45-46) competed for binding. (C) In vitro assay comparing neutralization of YU2 by sCD4 (squares), 8ANC195 IgG (triangles), and an equimolar mixture of 8ANC195 and sCD4 (circles). (D) Packing of 8ANC195/sCD4/gp120 crystals. Several symmetry mates are shown as surface representations (8ANC195 HC; 8ANC195 LC; 93TH057 gp120; sCD4 D1D2). Areas where two complexes form crystal contacts are indicated. (E) In vitro assay comparing neutralization of YU2 by 8ANC195 IgG (squares), 3BNC60 IgG (triangles), and an 8ANC195 IgG mutant that lacks the FWR3 insertion (Ser77a-Pro77b-Pro77c-Ile77d) that results in the protruding "FWR3$_{HC}$ thumb" (circles).
Figure 3B:
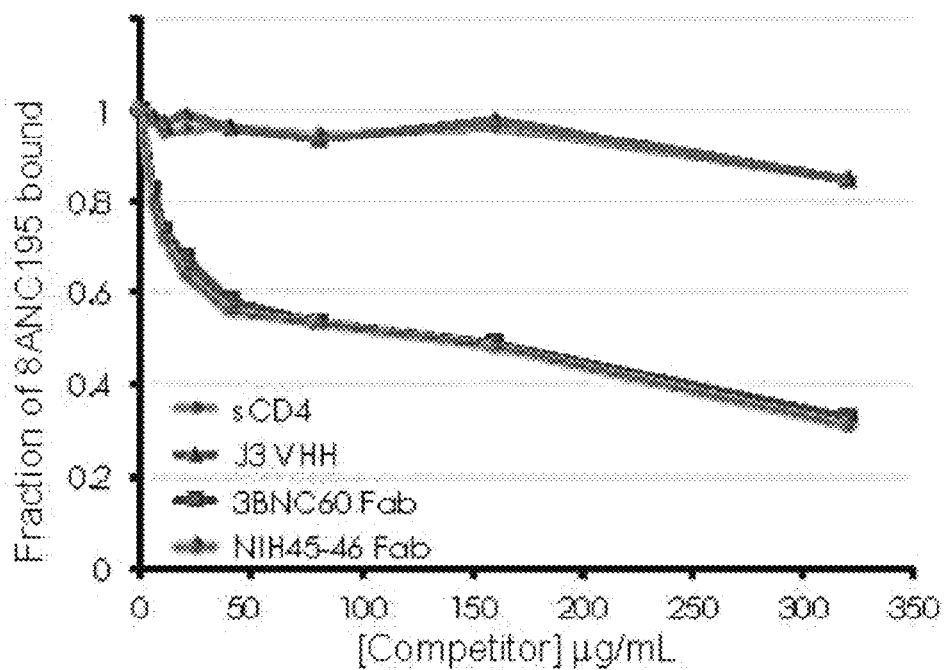
Figure 3C:
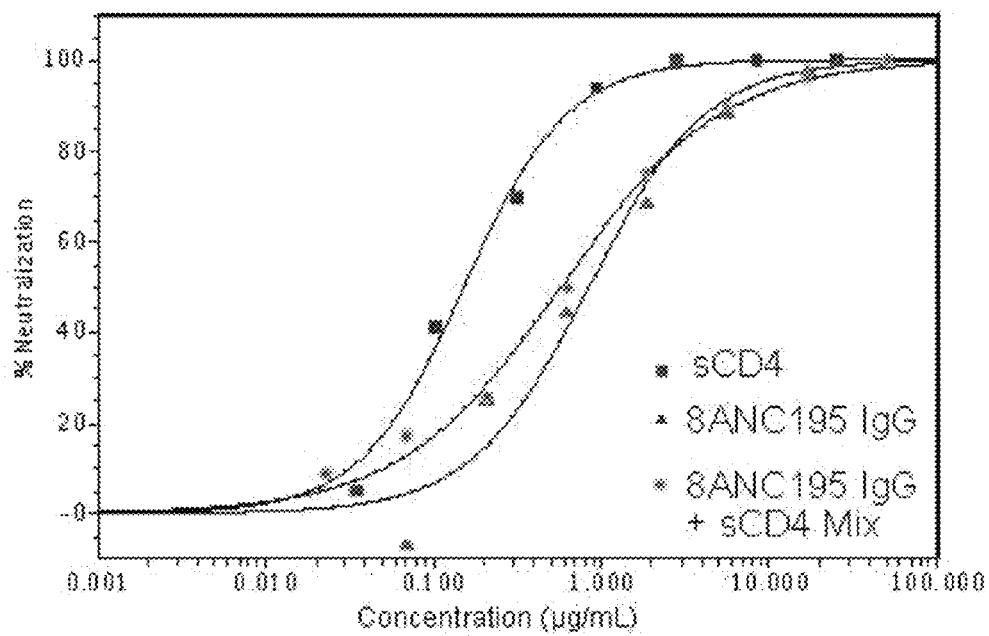
Figure 3D:
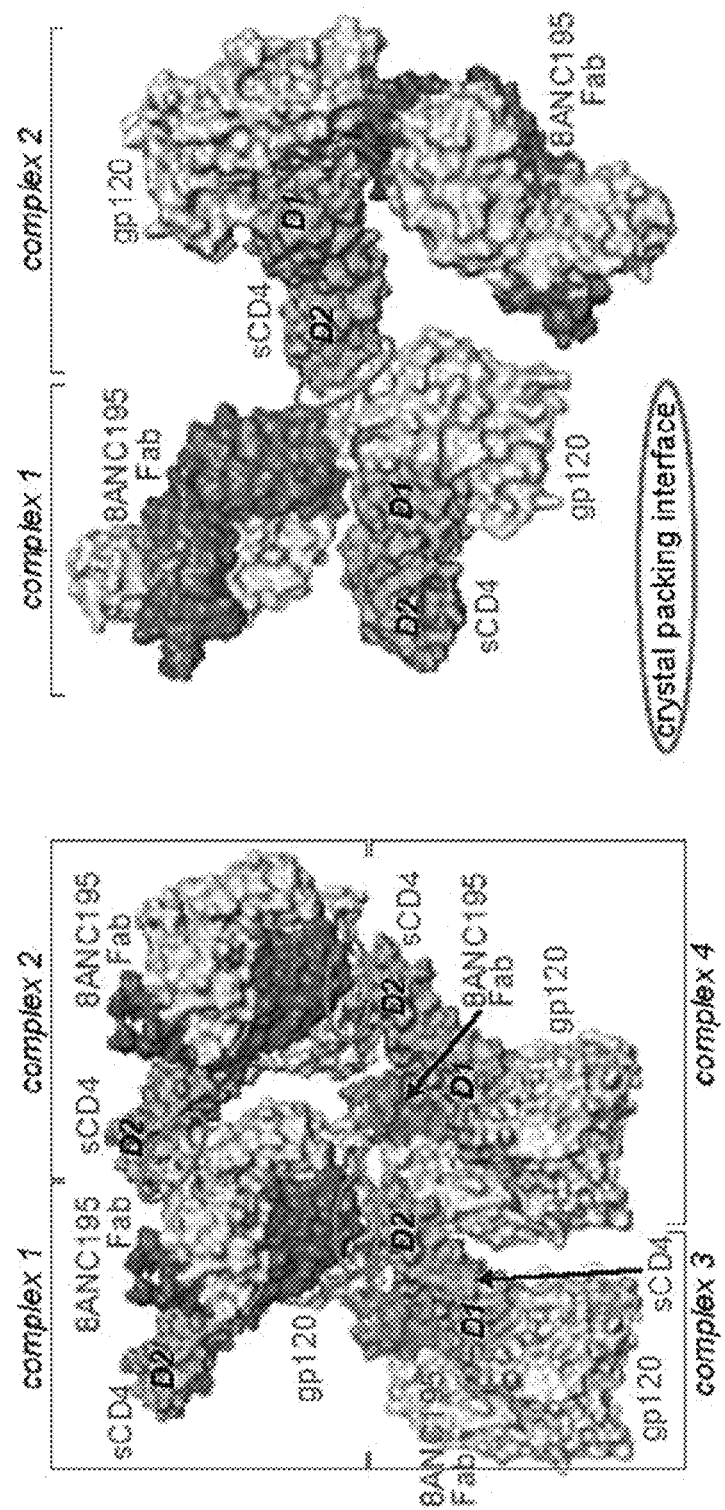
Figure 3E:
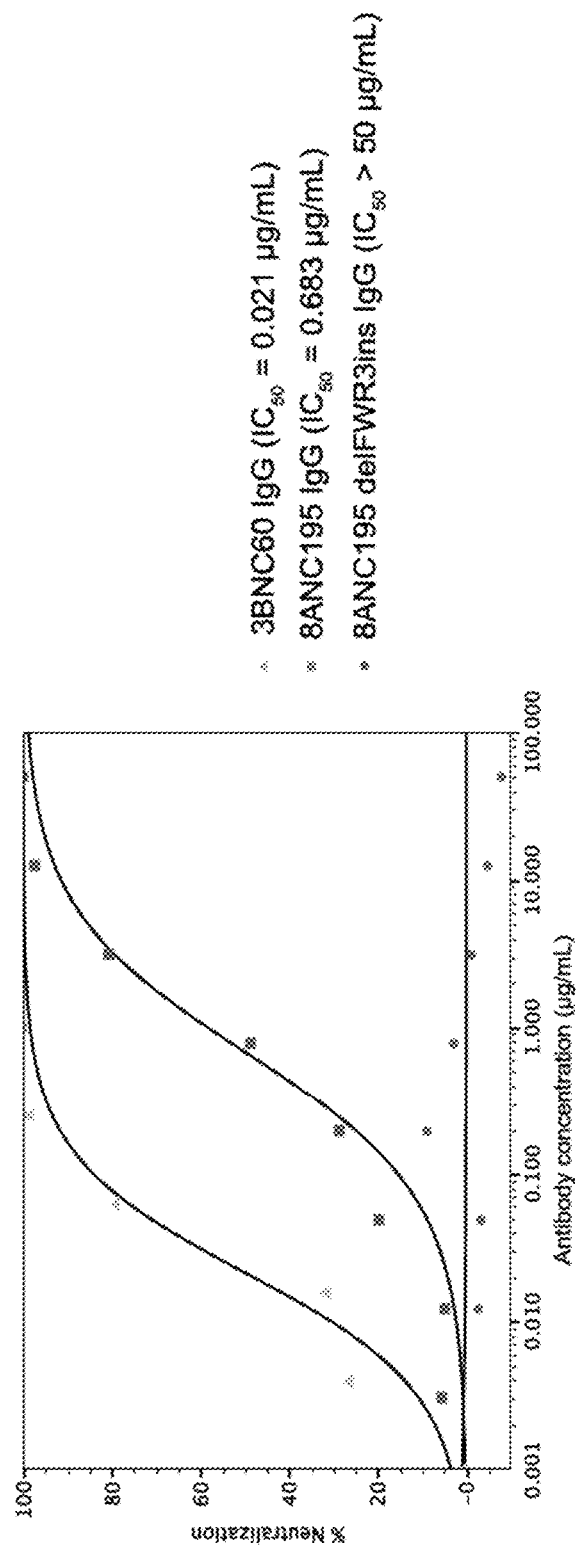

The complex structure showed independent binding of sCD4 and 8ANC195 Fab to distinct sites on gp120 (FIG. 16B). sCD4 interacted with the gp120 core as in other sCD4-gp120 structures (Kwong et al., Nature 393, 648 (1998)) (FIG. 3A), thus its binding was not altered by the presence of the adjacent antibody, consistent with binding and neutralization experiments showing no effects of CD4 addition on 8ANC195 activity (FIG. 3B,C). sCD4 did, however, contribute to crystal packing (FIG. 3D), rationalizing why diffraction-quality crystals failed to grow in its absence. In the ternary complex structure, 8ANC195 bound to a gp120 region adjacent to the CD4 binding site, contacting mainly the gp120 inner domain, loops D and V5, and a small patch of the gp120 outer domain (His352$_{gp120}$-Asn354$_{gp120}$) (FIG. 16B,C).

8ANC195 Fab bound gp120 core exclusively with its HC, using residues in FWRs and its three CDR loops to form an extensive interface (3,671 Å$^2$ total buried surface area; 1287 Å$^2$ HC gp120 protein contacts; 2,384 Å$^2$ HC-gp120 glycan contacts) (FIG. 16B, 2, FIG. 4; Table 2).

TABLE 2

Buried Surface Area (BSA) at Interfaces

| gp120 | BSA (Å$^2$) | 8ANC195 HC | BSA (Å$^2$) |
|---|---|---|---|
| VAL 44 | 19.4 | ASN 28 | 28.6 |
| TRP 45 | 17.4 | THR 29 | 22.9 |
| LYS 46 | 35.1 | GLY 31 | 26.3 |
| ASP 47 | 39.7 | LEU 32 | 56.0 |
| THR 90 | 39.1 | ARG 54 | 54.5 |
| GLU 91 | 5.7 | TRP 55 | 4.2 |
| ASN 92 | 87.3 | LYS 56 | 4.4 |
| PHE 93 | 9.0 | LEU 74 | 65.7 |
| ASN 94 | 38.0 | THR 75 | 44.3 |
| LYS 97 | 7.2 | GLY 76 | 81.0 |
| THR 236 | 27.7 | SER 77 | 33.9 |
| GLY 237 | 21.1 | SER 78 | 5.5 |
| PRO 238 | 51.6 | PRO 79 | 3.9 |
| LYS 240 | 4.1 | THR 104 | 11.7 |
| SER 274 | 0.2 | TYR 105 | 100.2 |
| GLU 275 | 7.0 | ASP 106 | 16.8 |
| ASN 276 | 15.9 | LYS 107 | 24.0 |
| LEU 277 | 37.8 | TRP 108 | 70.3 |
| THR 278 | 69.8 | | |
| HIS 352 | 17.0 | | |
| PHE 353 | 10.0 | | |
| ASN 354 | 48.1 | | |
| LYS 357 | 3.5 | | |
| ARG 456 | 13.8 | | |
| THR 463 | 0.2 | | |
| GLU 466 | 0.1 | | |
| LYS 487 | 8.0 | | |
| Total gp120 | 633.4 | Total 8ANC195 HC | 653.9 |
| gly276 NAG$^1$ | 121.2 | TYR 25 | 12.8 |
| | | GLY 26 | 36.7 |
| | | VAL 27 | 6.5 |
| | | ASN 28 | 15.3 |
| | | LEU 74 | 21.2 |
| | | PRO 79 | 4.2 |
| gly276 NAG$^2$ | 100.5 | GLN 1 | 18.8 |
| | | HIS 3 | 8.0 |
| | | TYR 25 | 40.8 |
| | | GLY 26 | 12.8 |
| gly276 BMA$^3$ | 65.5 | HIS 3 | 35.3 |
| | | VAL 5 | 6.5 |
| | | TYR 25 | 19.4 |
| gly276 MAN$^4$ | 66.5 | GLN 1 | 14.9 |
| | | ILE 2 | 1.6 |
| | | HIS 3 | 40.0 |
| gly276 MAN$^5$ | 45.2 | VAL 5 | 18.4 |
| | | TYR 25 | 18.7 |
| Total gly276 | 398.8 | Total 8ANC195 HC | 331.8 |
| gly234 NAG$^1$ | 108.4 | ASN 28 | 1.5 |
| | | THR 29 | 9.8 |
| | | TRP 55 | 24.9 |
| | | ASP 73 | 29.7 |
| | | LEU 74 | 16.8 |
| gly234 NAG$^2$ | 128.4 | ARG 54 | 1.0 |
| | | TRP 55 | 53.4 |
| | | ALA 71 | 2.8 |
| | | VAL 72 | 11.6 |
| | | ASP 73 | 13.1 |
| gly234 BMA$^3$ | 100.6 | ILE 52 | 9.5 |
| | | TRP 55 | 24.5 |
| | | LYS 56 | 0.2 |
| | | SER 57 | 3.4 |
| | | ILE 69 | 0.8 |
| | | SER 70 | 10.5 |
| | | ALA 71 | 11.4 |
| | | VAL 72 | 10.5 |
| gly234 MAN$^4$ | 55.2 | SER 70 | 8.8 |
| | | ALA 71 | 5.2 |
| | | VAL 72 | 31.0 |
| gly234 MAN$^5$ | 129.8 | SER 70 | 11.9 |
| | | ALA 71 | 1.8 |
| | | VAL 72 | 18.1 |
| | | ILE 81 | 18.5 |
| | | SER 83 | 18.6 |
| gly234 MAN$^6$ | 118.4 | THR 19 | 16.7 |
| | | LEU 68 | 24.3 |
| | | SER 70 | 8.9 |
| | | SER 83 | 7.6 |
| | | GLU 85 | 25.7 |
| gly234 MAN$^7$ | 84.2 | ILE 52 | 3.3 |
| | | TRP 55 | 13.4 |
| | | LYS 56 | 1.8 |
| | | SER 57 | 20.2 |
| | | LEU 68 | 16.2 |
| | | ILE 69 | 3.8 |
| | | SER 70 | 2.1 |
| gly234 MAN$^8$ | 68.3 | SER 57 | 30.2 |
| | | SER 58 | 0.2 |
| | | VAL 67 | 2.8 |
| | | LEU 68 | 24.4 |
| | | ILE 69 | 1.2 |
| gly234 MAN$^{10}$ | 198.7 | SER 57 | 20.9 |
| | | SER 58 | 11.0 |
| | | ALA 59 | 21.8 |
| | | ARG 64 | 14.3 |
| | | GLY 65 | 14.2 |
| | | VAL 67 | 13.3 |
| | | LEU 68 | 10.9 |
| | | ILE 69 | 3.5 |
| Total gly234 | 992.0 | Total 8ANC195 HC | 661.2 |

Hydrogen Bonds at Interfaces

| gp120 | | 8ANC195 HC | | Distance (Å) |
|---|---|---|---|---|
| THR 278 | Oγ1 | THR 75 | O | 2.43 |
| ARG 456 | NH2 | GLY 76 | O | 3.37 |
| ASN 354 | Nδ2 | SER 77 | Oγ | 2.88 |
| THR 278 | Oγ1 | SER 78 | O | 3.34 |
| ASN 92 | Nδ2 | THR 104 | O | 2.88 |
| ASN 92 | Nδ2 | TYR 105 | O | 3.08 |
| HIS 352 | O | THR 75 | Oγ1 | 3.14 |
| ASN 354 | Oδ1 | THR 75 | Oγ1 | 3.08 |
| ASP 47 | Oδ2 | TYR 105 | OH | 3.09 |
| LYS 487 | Nζ | TYR 105 | OH | 3.49 |
| gly234 NAG$^1$ | O4 | TRP 55 | Nε1 | 2.99 |
| gly234 NAG$^1$ | O3 | ASP 73 | Oδ2 | 3.30 |
| gly234 NAG$^2$ | O6 | ASP 73 | N | 3.13 |
| gly234 MAN$^5$ | O6 | VAL 72 | N | 2.76 |
| gly234 MAN$^5$ | O6 | ILE 81 | O | 2.64 |

TABLE 2-continued

| | | | | |
|---|---|---|---|---|
| gly234 MAN$^6$ | O3 | GLU 85 | Oε2 | 3.17 |
| gly234 MAN$^6$ | O4 | GLU 85 | Oε2 | 2.34 |
| gly234 MAN$^{10}$ | O3 | ALA 59 | N | 3.50 |
| gly234 MAN$^{10}$ | O2 | ALA 59 | N | 3.03 |
| gly234 MAN$^{10}$ | O6 | VAL 67 | O | 3.17 |
| gly234 MAN$^{10}$ | O6 | GLY 65 | N | 2.58 |
| gly234 MAN$^{10}$ | O2 | SER 58 | O | 3.28 |
| gly234 MAN$^{10}$ | O2 | SER 58 | N | 3.19 |
| gly234 MAN$^{10}$ | O3 | SER 57 | O | 2.79 |

A loop in FWR3$_{HC}$, consisting of somatically-mutated residues and extended by a four-residue insertion, reached like a thumb into the pocket formed by loops D, V5 and outer domain residues 352$_{gp120}$-358$_{gp120}$ (FIGS. 16A,B and 17A, FIG. 4B). CDRH1 and CDRH3 contacted the gp120 inner domain (FIG. 16B, FIG. 4B), contributing to a 1287 Å$^2$ interface between the 8ANC195 HC and gp120 protein residues. The CDRH1 and CDRH3 loop conformations, conserved in the free Fab (FIG. 16A, FIG. 2A,B), were necessary for binding gp120 since extending these loops would result in clashes with gp120. The resulting antibody combining site was exquisitely suited to contacting portions of the inner domain of gp120 not targeted by other bNAbs (FIG. 16C).

The 8ANC195 Fab also made extensive interfaces with glycans attached to Asn234$_{gp120}$ (buried surface area=1,653 Å$^2$) and Asn276$_{gp120}$ (buried surface area=731 Å$^2$), rationalizing its dependence on these PNGSs for neutralization (West, Jr. et al., *Proceedings of the National Academy of Sciences of the United States of America* 110, 10598 (2013); Chuang et al., *Journal of virology* 87, 10047 (2013)). Together with CDRH2, somatically-mutated FWR residues in strands B, C", D and E contributed to an extensive interface with the Asn234$_{gp120}$-associated N-glycan (usually high mannose in native HIV-1 Envs (Go et al., *Journal of virology* 85, 8270 (2011) that involved 10 sugar moieties, including specific interactions with terminal mannose residues (FIG. 17C,E, FIG. 4C,D). A two-residue deletion at the CDRH2FWR3$_{HC}$ boundary compared to the germline sequence permitted these interactions, since the longer loop would clash with inner domain residue Asn234$_{gp120}$ and its neighbors. The Asn276$_{gp120}$ glycan (a complex-type N-glycan in native HIV-1 Envs (Go et al., *Journal of virology* 85, 8270 (2011); Binley et al., *Journal of virology* 84, 5637 (2010)), but high mannose in the crystallized gp120) was wedged between 8ANC195 and sCD4, where it contacted FWR residues in strands A and B and the N-terminal portion of CDRH1, forming an interface involving only the core pentasaccharide common to both high mannose and complex-type N-glycans (FIG. 17D, FIG. 4E,F).

Figures 5A, 5B:
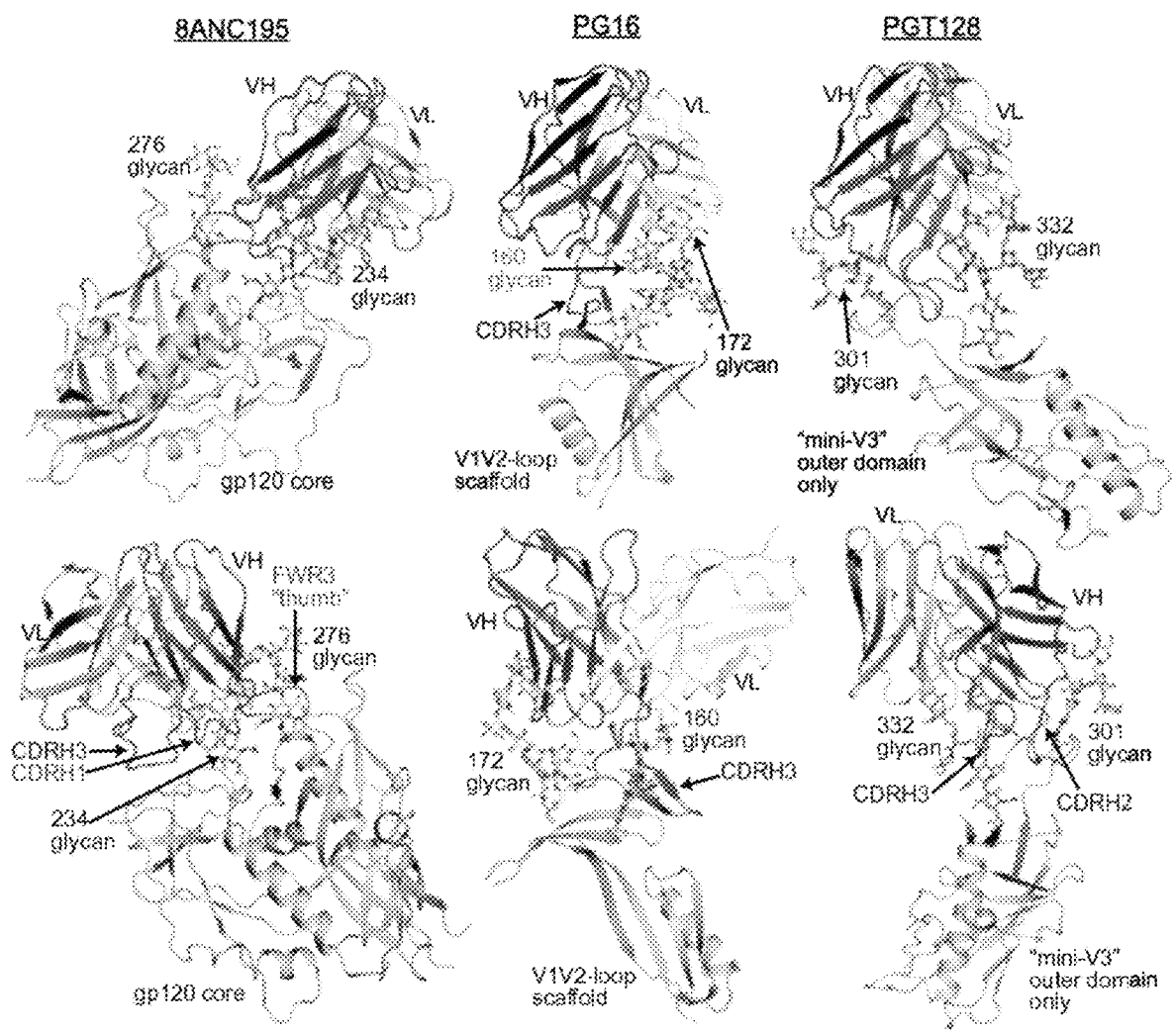
FIGS. 5A and 5B illustrates a comparison of glycan-dependent bNAbs. 8ANC195 is "bracketed" by two glycans (Asn234$_{gp120}$ glycan; Asn276$_{gp120}$ glycan) in the 8ANC195 Fab/gp120/sCD4 complex structure (left panels). For comparison, crystal structures of PG16 (middle panels, PDB 4DQO) bound to a V1/V2 loop scaffold and PGT128 (right panels, PDB 3TYG) bound to a V3 loop scaffold are shown with (A) the antibody HCs aligned to the 8ANC195 HC or (B) an alternative view showing their interactions with bracketing glycans (for PG16: Asn160$_{gp120}$ glycan/ Asn172$_{gp120}$ glycan; for PGT128: Asn301$_{gp120}$ glycan/ Asn332$_{gp120}$ glycan). The proteins are shown as ribbon diagrams and the glycans as stick representations.

The 8ANC195 HC was bracketed by the Asn234$_{gp120}$ and Asn276$_{gp120}$ glycans in a manner analogous to interactions of HIV-1 antibodies that penetrate the Env glycan shield, such as PG16 (interactions with Asn156$_{gp120}$/Asn173$_{gp120}$ and Asn160$_{gp120}$ glycans) (Pancera et al., *Nature structural & molecular biology* 20, 804 (2013), PGT128 (with Asn301$_{gp120}$ and Asn332$_{gp120}$ glycans) (Pejchal et al., *Science* 334, 1097 (2011)) and PGT121 (with Asn137$_{gp120}$ and Asn332$_{gp120}$ glycans) (Mouquet et al., *Proceedings of the National Academy of Sciences of the United States of America* 109, E3268 (2012); Julien et al., *Science* 342, 1477 (2013) Julien et al., *PLoS pathogens* 9, e1003342 (2013)) (FIG. 5). However, in contrast to these antibodies, 8ANC195 contacts with gp120 were made exclusively by its HC; indeed, 33% of 8ANC195 V$_H$ domain residues not buried at the LC interface contacted gp120. In summary, the 8ANC195-gp120 structure demonstrated that 8ANC195 recognizes a novel epitope involving the Asn234$_{gp120}$ and Asn276$_{gp120}$ glycans, the gp120 inner domain, loop D and loop V5, which would be adjacent to gp41 in Env trimer (Julien et al., *Science* 342, 1477 (2013); Lyumkis et al., *Science* 342, 1484 (2013)).

Example 3

Figures 7A, 7B:
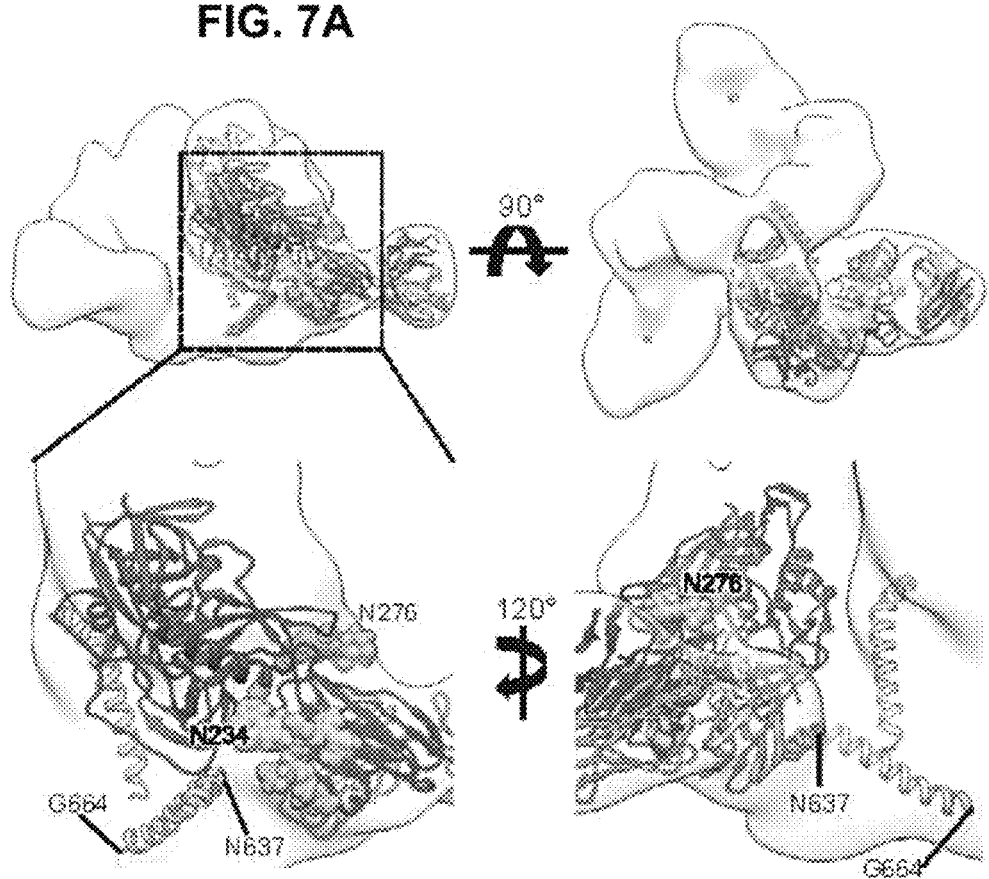
FIGS. 7A and 7B illustrates negative stain EM reconstruction of BG505 SOSIP.664 in complex with 8ANC195 Fab fit two ways. (A) When the gp120-8ANC195 Fab structure was fit into the EM density, the gp120 from the complex structure was displaced slightly outwards in comparison to the gp120 in the SOSIP trimer structure. The HC and LC of the Fab are shown. The Asn234$_{gp120}$ and Asn276$_{gp120}$ glycans are shown as spheres. (B) Close up of the Fab-Env interface. The position of Asn637$_{gp120}$ can be deduced from the position of the C-terminus of HR2, which corresponds to residue Gly664$_{gp41}$. This residue is in close proximity to the LC and the glycan at this position could interact with the 8ANC195 Fab.

Negative Stain Single Particle Electron Microscopy (EM) to Determine the Structure of 8ANC195 Fab Bound to a Soluble HIV-1 SOSIP Trimer To investigate portions of the 8ANC195 epitope beyond the gp120 core, including potential contacts with gp41, negative stain single particle EM was used to determine the structure of 8ANC195 Fab bound to a soluble HIV-1 SOSIP trimer derived from strain BG505 (FIG. 6) (Julien et al., *Science* 342, 1477 (2013); Lyumkis et al., *Science* 342, 1484 (2013); Sanders et al., *PLoS pathogens* 9, e1003618 (2013)). Independent docking of the BG505 Env trimer structure (PDB 4NCO) (Julien et al., *Science* 342, 1477 (2013)) and 8ANC195 Fab resulted in a model wherein the Fab contacted both gp120 and gp41 within a single protomer (FIG. 18A, FIG. 7). The EM model placed the CDRL1, CDRL2, and portions of FWR3$_{LC}$ and CDRH3 in close proximity to the HR2 helix of gp41 (FIG. 18B). Although gp41 residues were not definitively identified in the trimer crystal structure (Julien et al., *Science* 342, 1477 (2013)), based on the assignment of the HR2 C-terminus as Gly664$_{gp41}$ (Lyumkis et al., *Science* 342, 1484 (2013), the kink in the HR2 helix was assigned as Asn637$_{gp41}$ (FIG. 18B, FIG. 8), the asparagine of a highly conserved PNGS. The EM model predicted that the Asn637$_{gp41}$-linked glycan and adjacent amino acid residues on HR2 interacted with 8ANC195 CDRH3, CDRL1 and CDRL2.

Docking of the gp120-8ANC195 portion of the ternary crystal structure onto the SOSIP trimer structure resulted in a slightly different angular placement of the Fab in the EM density than when the 8ANC195 Fab was fit independently (FIG. 18A, FIG. 7). The Fab, especially the LC, was pushed further away from gp41 by comparison to the placement suggested by the complex crystal structure. The LC position in the EM model was more likely to be accurate since it left space for bulky side chains at positions 625$_{gp41}$-640$_{gp41}$ that were modeled as alanines in the trimer crystal structure (Julien et al., *Science* 342, 1477 (2013); Lyumkis et al., *Science* 342, 1484 (2013)). The slightly different placements could be due to crystal packing effects, spatial restraints imposed by the gp41 glycans that were not present in the 8ANC195-gp120 complex, removal of the PNGS at Asn88$_{gp120}$ in the gp120 core, which may have allowed for a closer association of 8ANC195 and gp120 in the crystal structure, and/or a small conformational change in the gp120 region of the trimer to accommodate the Fab orientation trapped by crystallization.

Example 4

Neutralization and Binding Assays

The EM reconstruction highlighted a potential role for 8ANC195 LC contacts to gp41. To assess LC contacts with trimeric Env, chimeras consisting of the 8ANC195 HC paired with different Lcs were tested in neutralization and binding assays. The chimeras included a full germline LC, a mature LC with individual CDR loops reverted to their germline sequences or CDRL3 partially mutated to alanines, or the LC from the CD4 binding site antibody 3BNC117 (FIG. 19A). As expected from the crystal structure in which all gp120 contacts were made by the 8ANC195 HC, the chimeras bound normally to gp120 core and to a full-length 93TH057 gp120 (FIG. 19B, table 3), thus changes in the LC did not disrupt the HC portion of the antibody combining site.

TABLE 3

| Antibody | Kp (nM) 93TH057 gp120 | Kp (nM) YU2 Gp120 | IC50 (µg/mL) YU2 | IC50 (µg/mL) Tro11 | IC50 (µg/mL) SF162 | IC50 (µg/mL) 6535_3 | IC50 (µg/mL) SC4226618 | IC50 (µg/mL) PV04 | IC50 (µg/mL) REJO4541 | IC50 (µg/mL) RHPA4259 |
|---|---|---|---|---|---|---|---|---|---|---|
| 8ANC195 IgG | 33.1 | 82.0 | 0.4 | 0.31 | 0.30 | 0.43 | 0.69 | 0.52 | 0.248 | 0.17 |
| 8ANC195 mHC/GILC | 38.0 | 56.1 | 6.76 | >100 | 12.9 | 8.9 | 8.1 | 11.5 | 11.2 | 14.6 |
| 8ANC195 gICDRL1 | 38.0 | 105.4 | 55 | >100 | 65 | 24 | 97 | >100 | 62.4 | 0.96 |
| 8ANC195 gICDRL2 | 40.5 | 119.5 | 6.26 | 18.9 | 44 | 13.3 | 69 | 97 | 82.9 | 0.82 |
| 8ANC195 gICDRL3 | 44.4 | 107.1 | 0.79 | 0.75 | 0.85 | 1.08 | 1.29 | 3.1 | 1.045 | 0.97 |
| 8ANC195 CDRL3Ala | ND | ND | 39 | ND | >100 | >100 | >100 | >100 | >100 | 0.81 |
| 8ANC195HC/3BNC117LC | ND | ND | 4.77 | 5.33 | 5.6 | >100 | 22 | ND | 10.9 | 4.52 |
| 3BNC60 | ND | ND | 0.027 | 0.04 | 0.05 | 0.335 | 0.07 | 0.06 | 0.063 | 0.02 |

In contrast to gp120 binding, neutralization potencies assayed against native Env spike trimers were decreased by changes in the 8ANC195 LC. For example, reverting CDRL1 and CDRL2 sequences to germline precursor sequences (changing 3 of 7 and 3 of 3 residues, respectively) almost completely abrogated neutralization of YU2, an 8ANC195-sensitive strain. Changes to CDRL3 led to a moderate reduction in neutralization potency, as did substituting the 3BNC117 LC for the cognate LC (FIG. 19B, table 3). A chimeric IgG with one of the most conservatively-substituted LCs (Thr-Gly-Asn, mature CDRL1 containing a one-residue insertion, reverted to Ser-Ser, germline CDRL1) displayed unchanged binding to gp120, yet showed reductions in neutralization potency of up to 250-fold Similarly, conservative changes in CDRL2 (Arg-Gly-Ala, the mature CDRL2, reverted to the germline Lys-Ala-Ser sequence) caused large reductions in neutralization potencies but had little effect on gp120 binding. Overall the data showed differential sensitivities of the binding and neutralization assays to changes in the 8ANC195 LC that were distant from the gp120 surface, which supported the EM results suggesting that LC, and CDRL1 and CDRL2 in particular, contacted gp41.

Example 5

Isolation of Antibodies

Figure 9A:
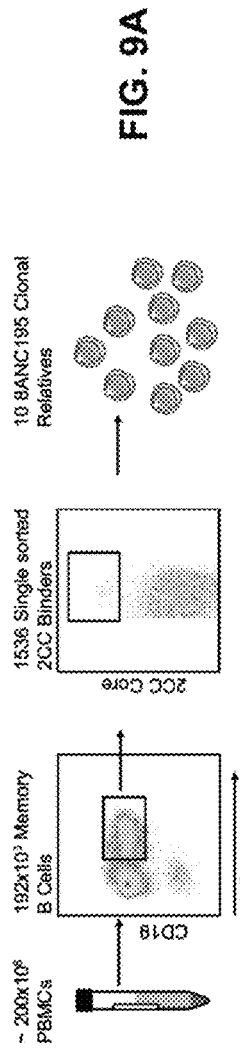
FIGS. 9A, 9B and 9C relate to Single Cell Variants of 8ANC195. (A) Strategy of large scale single cell sorting. (B) IgH and IgL chain genes from isolated single cell variants of 8ANC195. Identical members are grouped together. The HC CDR3 of 8ANC195 has the sequence of SEQ ID NO:38. The HC CDR3 of 8ANC142 has the sequence of SEQ ID NO:39. The HC CDR3 of 8ANC3430 has the sequence of SEQ ID NO:40. The HC CDR3 of 8ANC3484 has the sequence of SEQ ID NO:41. The HC CDR3 of 8ANC3044 has the sequence of SEQ ID NO:42. The HC CDR3 of 8ANC3630 has the sequence of SEQ ID NO:43. The LC CDR3 of 8ANC195 has the sequence of SEQ ID NO:44. The LC CDR3 of 8ANC142 has the sequence of SEQ ID NO:45. The LC CDR3 of 8ANC3430 has the sequence of SEQ ID NO:46. The LC CDR3 of 8ANC3484 has the sequence of SEQ ID NO:47. The LC CDR3 of 8ANC3044 has the sequence of SEQ ID NO:48. The LC CDR3 of 8ANC3630 has the sequence of SEQ ID NO:49. (C) IC$_{50}$ neutralization titers of distinct single cell versions of the 8ANC195 clone compared to 8ANC195 against a 15 virus Tier 2 panel.
Figure 9B:
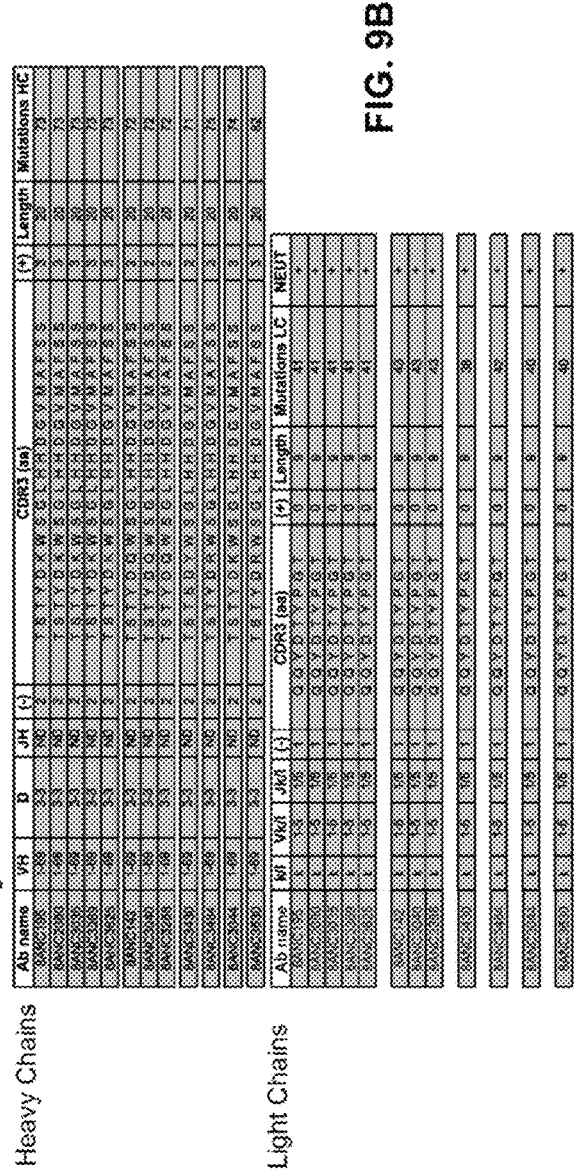
Figure 9C:
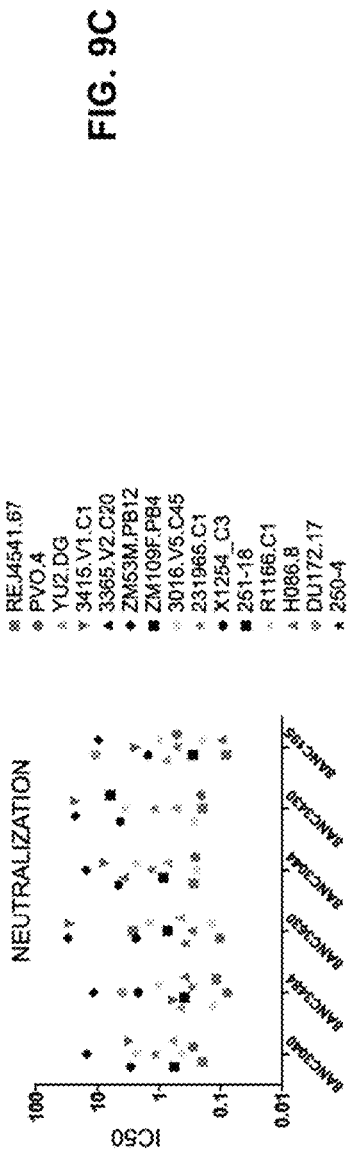

To further investigate Env recognition by 8ANC195, additional members of this antibody clone were isolated from the original donor by single cell sorting using gp120 stabilized in the CD4-bound conformation (2CC core) as bait (FIG. 9). From 1536 single 2CC core-binding B cells, 10 (0.7%) were clonally related to 8ANC195, and of these, only four differed slightly from the two previously-described members (1 to 3 and 1 to 7 residue differences in the HCs and LCs, respectively) (FIG. 10). Consistent with the limited sequence diversity, these antibodies exhibited similar potencies to 8ANC195 in neutralization assays against a panel of 15 Tier 2 viruses (FIG. 9C and Table 4).

TABLE 4

| Virus | 8ANC3040 | 8ANC3484 | 8ANC3630 | 8ANC3044 | 8ANC3430 | 8ANC195 |
|---|---|---|---|---|---|---|
| REJO4541.67 | 0.198 | 0.117 | 2.652 | 0.278 | 0.198 | 0.08 |
| PVO.4 | 0.284 | 0.077 | 0.102 | 0.260 | 0.206 | 0.52 |
| YU2.DG | 0.617 | 0.461 | 0.468 | 0.747 | 0.545 | 0.79 |
| 3415.v1.c1 | 3.059 | 0.589 | 27.977 | 7.557 | >23 | 2.404 |
| 3365.v2.c20 | >25 | >30 | >30 | >30 | >23 | >30 |
| ZM53M.PB12 | 14.910 | 11.581 | >30 | 15.164 | >23 | 9.626 |
| ZM109F.PB4 | NT | >30 | >30 | >30 | >23 | >30 |
| 3016.v5.c45 | 0.427 | 0.131 | 0.136 | 0.242 | 0.271 | 0.195 |
| 231965.c1 | 1.174 | 0.294 | 0.375 | 1.332 | 1.190 | 0.514 |
| X1254_c3 | 2.909 | 2.192 | 2.377 | 4.538 | 4.284 | 1.524 |
| 251-18 | 0.571 | 0.391 | 0.730 | 0.858 | 6.170 | 0.284 |
| R1166.c1 | 2.370 | 1.027 | 1.453 | 2.381 | 3.642 | 0.986 |
| H086.8 | NT | 0.394 | 0.300 | 3.830 | >23 | 0.095 |
| Du172.17 | NT | 4.011 | >30 | >30 | >23 | 10.797 |
| 250-4 | NT | >30 | >30 | >30 | >23 | >50 |
| MuLV | >30 | >30 | >30 | >30 | >23 | >23 |

Reasoning that the 2CC core bait might fail to capture some 8ANC195 family members, clone-specific primers were used to amplify 8ANC195 variants from purified populations of CD19+ IgG+ memory B cells (FIG. 11). 128 HC and 100 LC sequences were obtained that were clonally related to 8ANC195 and displayed greater sequence diversity than antibodies obtained using antigen-specific selection (FIGS. 10, 12). Of the 13 HC and 6 LC genes exhibiting greatest diversity, all combinations were co-transfected in order to evaluate their neutralizing activity against a 15-member Tier 2 virus panel. 3 of 39 (7.7%) new antibodies were at least as broad and potent as 8ANC195 (FIG. 19C and Table 5).

TABLE 5

| | γ3 | γ4 | γ8 | γ15 | γ20 | γ22 | γ23 | γ44 | γ46 | γ52 | γ59 |
|---|---|---|---|---|---|---|---|---|---|---|---|
| Virus | γ3κ3 | γ4κ3 | γ8κ3 | γ15κ3 | γ20κ3 | γ22κ3 | | | | γ52κ3 | γ59κ3 |
| REJO4541.67 | 0.260 | >15 | >15 | >15 | >15 | >15 | | | | >15 | 8.543 |
| PVO.4 | 0.170 | >15 | >15 | 5.316 | >15 | >15 | | | | 1.918 | >15 |
| YU2.DG | 0.420 | >15 | 5.418 | 1.068 | >15 | >15 | | | | 5.751 | 8.970 |
| 34 > 15.v1.c1 | >15 | >15 | >15 | >15 | >15 | >15 | | | | >15 | >15 |
| 3365.v2.c20 | >15 | >15 | >15 | >15 | >15 | >15 | | | | >15 | >15 |
| ZM53M.PB12 | >15 | >15 | >15 | >15 | >15 | >15 | | | | >15 | >15 |
| ZM109F.PB4 | >15 | >15 | >15 | >15 | >15 | >15 | | | | >15 | >15 |
| 3016.v5.c45 | 0.347 | >15 | 2.383 | 1.265 | >15 | >15 | | | | 3.050 | >15 |
| 231985.c1 | 0.727 | >15 | 3.477 | 1.611 | >15 | >15 | | | | 6.594 | >15 |
| X1254_c3 | 1.822 | 18.047 | 4.609 | 3.487 | 14.702 | >15 | | | | >15 | 3.392 |
| 251-18 | >15 | >15 | >15 | >15 | >15 | >15 | | | | 14.537 | >15 |
| R1166.c1 | 2.208 | >15 | 7.596 | 3.943 | >15 | >15 | | | | 23.408 | 24.225 |
| H086.8 | 3.307 | >15 | >15 | >15 | >15 | >15 | | | | >15 | >15 |
| Du172.17 | >15 | >15 | >35 | >15 | >15 | >15 | | | | >15 | >15 |
| 250-4 | >15 | >15 | >15 | >15 | >15 | >15 | | | | >15 | >15 |
| MuLV | >30 | NT | >18 | >30 | >21 | NT | | | | >30 | >30 |
| Virus | γ3κ5 | | | | | γ22κ5 | γ23κ5 | | γ46κ5 | γ52κ5 | γ59κ5 |
| REJO454.167 | 0.097 | | | | | 0.795 | 0.091 | | 0.196 | 0.035 | 4.669 |
| PVO.4 | 0.081 | | | | | 0.352 | 0.043 | | 0.129 | 0.018 | >15 |
| YU2.DG | 0.200 | | | | | 0.569 | 0.135 | | 0.359 | 0.066 | 7.279 |
| 34 > 15.v1.c1 | >15 | | | | | >15 | 1.479 | | >15 | 0.120 | >15 |
| 3365.v2.c20 | >15 | | | | | >15 | >15 | | >15 | >15 | >15 |
| ZM53M.PB12 | >15 | | | | | >15 | 6.675 | | 12.482 | 3.134 | 24.057 |
| ZM109F.PB4 | >15 | | | | | >15 | >15 | | >15 | >15 | >15 |
| 3016.v5.c45 | 0.314 | | | | | 0.103 | 0.091 | | 0.111 | 0.017 | >15 |
| 231985.c1 | 0.697 | | | | | 0.680 | 0.291 | | 0.525 | 0.094 | >15 |
| X1254_c3 | 1.717 | | | | | 1.521 | 0.919 | | 1.792 | 0.504 | 9.416 |
| 251-18 | 0.721 | | | | | 1.696 | 0.176 | | 0.609 | 0.048 | 6.959 |
| R1166.c1 | 2.074 | | | | | 2.395 | 1.075 | | 0.922 | 0.319 | 28.201 |
| H086.8 | 0.434 | | | | | >15 | 0.474 | | 1.750 | 0.175 | >15 |
| Du172.17 | 3.728 | | | | | >15 | 1.814 | | >15 | NT | >15 |
| 250-4 | >15 | | | | | >15 | >15 | | >15 | >15 | >15 |
| MuLV | >15 | | | | | >30 | >30 | | NT | NT | >30 |
| Virus | γ3κ11 | | γ8κ11 | γ15κ11 | γ20κ11 | γ22κ11 | γ23κ11 | γ44κ11 | γ46κ11 | γ52κ11 | γ59κ11 |
| REJO4541.67 | 0.091 | | >15 | >15 | >15 | >15 | 0.140 | >15 | >15 | 3.473 | 1.572 |
| PVO.4 | 0.074 | | 8.153 | 5.704 | >15 | >15 | 0.103 | >15 | 2.921 | 0.103 | >15 |
| YU2.DG | 0.276 | | 9.349 | 4.122 | >15 | >15 | 0.340 | >15 | 2.101 | 0.298 | 6.911 |
| 34 > 15.v1.c1 | >15 | | >35 | >15 | >15 | >15 | >15 | >15 | >15 | >15 | >15 |
| 3365.v2.c20 | >15 | | >15 | >15 | >15 | >15 | >15 | >15 | >15 | >15 | >15 |
| ZM53M.PB12 | >15 | | >15 | >15 | >15 | >15 | >15 | >15 | >15 | >15 | >15 |
| ZM109F.PB4 | >15 | | >15 | >15 | >15 | >15 | >15 | >15 | >15 | >15 | >15 |
| 3016.v5.c45 | 0.143 | | 2.463 | 1.325 | >15 | >15 | 0.159 | >15 | 1.932 | 1.161 | >15 |
| 231965.c1 | 0.455 | | 2.490 | 5.103 | >15 | >15 | 0.543 | >15 | 2.958 | 0.296 | >15 |
| X1254_c3 | 2.306 | | 4.144 | 13.687 | 7.583 | >15 | 1.695 | >15 | 5.662 | 2.419 | 4.669 |
| 251-18 | >15 | | >15 | >15 | >15 | >15 | 2.490 | >35 | >15 | 0.647 | >15 |
| R1166.c1 | 1.792 | | 3.883 | 9.813 | 20.237 | >15 | 1.611 | >15 | 3.390 | 1.159 | 12.680 |
| H086.8 | 0.778 | | >15 | >15 | >15 | >35 | >15 | >15 | >15 | 1.638 | >15 |
| Du172.17 | >15 | | >15 | >15 | >15 | >15 | 11.298 | >15 | >15 | >15 | >15 |
| 250-4 | >15 | | >15 | >15 | >15 | >15 | >15 | >15 | >15 | >15 | >15 |
| MuLV | >30 | | NT | >30 | >30 | >30 | >30 | >19 | >30 | >30 | >30 |
| Virus | γ3κ18 | γ4κ18 | | γ15κ18 | γ20κ18 | γ22κ18 | γ23κ18 | | γ46κ38 | γ52κ18 | γ59κ18 |
| REJO4541.67 | 0.049 | >15 | | >15 | >15 | >15 | 0.061 | | >15 | 2.132 | 1.227 |
| PVO.4 | 0.028 | >15 | | 1.588 | >15 | >15 | 0.047 | | 2.100 | 0.081 | >15 |
| VU2.DG | 0.070 | >15 | | 1.159 | >15 | 8.229 | 0.117 | | 2.360 | 0.265 | 7.707 |
| 34 > 15.v1.c1 | >15 | >15 | | >15 | >15 | >15 | >15 | | >15 | >15 | >15 |
| 3365.v2.c20 | >15 | >15 | | >15 | >15 | >15 | >15 | | >15 | >15 | >15 |
| ZM53M.PB12 | >15 | >15 | | >15 | >15 | >15 | >15 | | >15 | >15 | >15 |
| ZM109F.PB4 | >15 | >15 | | >15 | >15 | >15 | >15 | | >15 | >15 | >15 |
| 3016.v5.c45 | 0.057 | >15 | | 0.554 | >15 | 13.350 | 0.047 | | 2.993 | 0.129 | >15 |
| 231965.c1 | 0.163 | >15 | | 1.481 | >15 | 25.988 | 0.128 | | 4.157 | 0.264 | >15 |
| X1254_c3 | 0.616 | 16.224 | | 2.849 | 5.221 | 1.563 | 0.548 | | 4.202 | 1.567 | 4.066 |

TABLE 5-continued

| | | | | | | | | | |
|---|---|---|---|---|---|---|---|---|---|
| 251-18 | >15 | >15 | >15 | >15 | >15 | 1.678 | >15 | 0.116 | 25.839 |
| R1166.c1 | 0.578 | >15 | 1.986 | 20.036 | 7.311 | 0.708 | 4.096 | 1.381 | 11.701 |
| H086.8 | 0.209 | >15 | >15 | >15 | >15 | >15 | >15 | 0.464 | >15 |
| Du172.17 | 11.518 | >15 | >15 | >15 | >15 | 2.953 | >15 | >15 | >15 |
| 250-4 | >15 | >15 | >15 | >15 | >15 | >15 | >15 | >15 | >15 |
| MuLV | >30 | >30 | NT | >30 | >30 | >30 | >15 | >15 | >15 |

| Virus | $\gamma 20\kappa 19$ |
|---|---|
| REJO4541.67 | >15 |
| PVO.4 | >15 |
| YU2.DG | >15 |
| 34 > 15.v1.c1 | >15 |
| 3365.v2.c20 | >15 |
| ZM53M.PB12 | >15 |
| ZM109F.PB4 | >15 |
| 3016.v5.c45 | >15 |
| 231965.c1 | >15 |
| X1254_c3 | 2.991 |
| 251-18 | >15 |
| R1166.c1 | >15 |
| H086.8 | >15 |
| Du172.17 | >15 |
| 250-4 | >15 |
| MuLV | >15 |

| Virus | $\gamma 15\kappa 61$ | $\gamma 44\kappa 61$ | $\gamma 46\kappa 61$ | $\gamma 52\kappa 61$ | $\gamma 50\kappa 61$ |
|---|---|---|---|---|---|
| REJO4541.67 | 2.029 | >15 | 0.378 | 0.115 | 1.333 |
| PVO.4 | 1.258 | >15 | 0.244 | 0.078 | >15 |
| YU2.DG | 3.446 | >15 | 0.918 | 0.406 | 4.325 |
| 34 > 15.v1.c1 | >15 | >15 | >15 | 0.681 | >15 |
| 3365.v2.c20 | >15 | >15 | >15 | >15 | >15 |
| ZM53M.PB12 | >15 | >15 | 27.493 | 8.435 | 13.301 |
| ZM109F.PB4 | >15 | >15 | >15 | >15 | >15 |
| 3016.v5.c45 | 1.214 | >15 | 0.383 | 0.182 | >15 |
| 231965.c1 | 5.231 | >15 | 1.576 | 0.515 | >15 |
| X1254_c3 | 10.884 | >15 | 4.468 | 2.566 | 4.018 |
| 251-18 | 4.656 | >15 | 1.842 | 0.273 | 1.402 |
| R1166.c1 | 8.548 | >15 | 2.578 | 1.635 | 7.461 |
| H086.8 | >15 | >15 | 0.584 | 0.242 | >15 |
| Du172.17 | >15 | >15 | 26.083 | 7.275 | >15 |
| 250-4 | >15 | >15 | >15 | >15 | >15 |
| MuLV | >15 | >15 | >15 | >15 | >15 |

Of these, $\gamma 52_{HC}\kappa 5_{LC}$ was 5-fold more potent than 8ANC195 (neutralized 12 of 15 viruses with a mean IC$_{50}$ of 0.45 µg/ml as compared to 2.3 µg/ml for 8ANC195) (FIG. 13), a potency and breadth against this virus panel that was comparable to those of other bNAbs, such as VRC01 (neutralized 12 of 15 viruses with a 0.56 µg/ml mean IC$_{50}$) and 10-1074 (neutralized 6 of 15 viruses with a mean of 0.09 µg/ml), that target non-overlapping sites (Wu et al., *Science* 329, 856 (2010); Mouquet et al., *Proceedings of the National Academy of Sciences of the United States of America* 109, E3268 (2012)).

The LC was critical to the activity of more potent $\gamma 52_{HC}\kappa 5_{LC}$ variant, as demonstrated by diminished neutralization potencies when $K\kappa 5_{LC}$ was swapped for either $\kappa 3_{LC}$ or $\kappa 11_{LC}$ (FIG. 19C). The weaker neutralization could be explained by differences between $\kappa 5_{LC}$ and $\kappa 3_{LC}$ at solvent-exposed residues in CDRL2 ($53_{LC}$ and $54_{LC}$) and FWRL3 ($64_{LC}$), and a nearby buried residue ($34_{LC}$) that may affect the structural integrity of CDRL1. Modeling of YU2 gp41 residues into the Env trimer structure (Julien et al., *Science* 342, 1477 (2013)) suggested that 8ANC195 positions $53_{LC}$ and $54_{LC}$ were adjacent to the Asn637$_{gp41}$ PNGS (FIGS. 8, 14). The improved neutralizing activity of $\kappa 5_{LC}$ compared with the other newly-isolated LCs was associated with small side chains at positions $34_{LC}$ (Val), $53_{LC}$ (Ala) and $54_{LC}$ (Ala), whereas $\kappa 3_{LC}$ or $\kappa 11_{LC}$, which were less broadly neutralizing when paired with identical HCs, included bulkier and/or charged side chains that would clash with the nearby gp41 glycan. $\kappa 5_{LC}$ was the only LC containing an S64R$_{LC}$ substitution and this single change compared to the 8ANC195 LC may account for the 5-fold improved potency of $\gamma 52_{HC}\kappa 5_{LC}$. Residues in the immediate vicinity of Asn637$_{gp41}$ might also modify neutralization; all six viral strains that were potently neutralized by the $\gamma 52_{HC}\kappa 5_{LC}$ variant had Asp636$_{gp41}$ or Asn636$_{gp41}$ whereas the remaining eight strains had Ser636$_{gp41}$ ($p<0.001$ by G-test). The same association between Asp636$_{gp41}$/Asn636$_{gp41}$ and neutralization potency was also statistically significant for 8ANC195 ($p<0.01$ by G-test), consistent an interaction between the N-terminal portion of gp41 HR2 (residues ~625 to 640) and 8ANC195 LC (FIG. 8). Also consistent with changes in the gp41 HR2 region affecting 8ANC195 neutralization, a computational analysis of neutralization panel data using the Antibody Database program (West, Jr. et al., *Proceedings of the National Academy of Sciences of the United States of America* 110, 10598 (2013)) suggested that Glu632$_{gp41}$ was associated with stronger neutralization.

In conclusion, 8ANC195 defines a novel site of HIV-1 Env vulnerability to neutralizing antibodies that spans gp120 and gp41 (FIG. 15). Rather than penetrating the glycan shield using only a single CDR loop, a strategy employed by antibodies such as PG9 and PGT128 (Pejchal et al., *Science* 334, 1097 (2011); McLellan et al., *Nature* 480, 336 (2011)) 8ANC195 inserted its entire HC variable region into a gap in the shield to form a large interface, of which >50% involved contacts to gp120 glycans (FIG. 17).

Although it was not possible to obtain large numbers of 8ANC195 variants by standard single cell cloning techniques (Scheid et al., *J Immunol Methods* 343, 65 (2009)), randomly combining HCs and LCs obtained from memory B cells without antigen-specific sorting demonstrated that the target of this antibody supported neutralization activity comparable to that against the most vulnerable sites on Env. Potent variants of 8ANC195 are particularly since the epitope does not overlap with the targets of CD4 binding site, V2 loop, V3 loop or MPER antibodies.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein by reference in their entireties.

What is claimed is:

1. An isolated polynucleotide encoding an isolated polypeptide comprising the sequence of any one of SEQ ID NOs: 1-33.

2. A vector comprising the polynucleotide of claim 1.

3. A cultured cell comprising the vector of claim 2.

4. The polynucleotide of claim 1, wherein the polypeptide comprises an antibody heavy chain variable region comprising the sequence of any one of SEQ ID NOs: 1-18.

5. The polynucleotide of claim 1, wherein the polypeptide comprises an antibody light chain variable region comprising the sequence of any one of SEQ ID NOs: 19-33.

6. The polynucleotide of claim 1, wherein the polynucleotide encodes an anti-HIV-1 antibody comprising (i) a heavy chain variable region comprising the sequence of any one of SEQ ID NOs: 1-18 and (ii) a light chain variable region comprising the sequence of any one of SEQ ID NOs: 19-33.

7. The polynucleotide of claim 6, wherein the heavy chain variable region comprises SEQ ID NO: 1 and the light chain variable region comprises SEQ ID NO: 20.

8. The polynucleotide of claim 1, wherein the polynucleotide is a DNA, cDNA, or RNA molecule.

9. The vector of claim 2, wherein the vector is an expression vector.

10. The vector of claim 2, wherein the vector is a lentiviral vector.

11. A pharmaceutical composition comprising the vector of claim 2 and a pharmaceutically acceptable carrier.

* * * * *

SEQUENCE LISTING

```
<160> NUMBER OF SEQ ID NOS: 123

<210> SEQ ID NO 1
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
    50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Arg Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 2
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
    50                  55                  60
```

Gly Arg Val Ile Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Ser Asp Tyr Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 3
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Ile His Leu Val Gln Ser Gly Thr Gly Val Lys Lys Pro Gly Ser
1               5                   10                  15

Ser Val Thr Val Ser Cys Lys Ala Tyr Gly Val Asn Thr Phe Gly Leu
                20                  25                  30

Tyr Ala Val Asn Trp Val Arg Gln Ala Pro Gly Gln Gly Leu Glu Tyr
            35                  40                  45

Ile Gly Gln Ile Trp Arg Trp Lys Ser Ser Ala Ser His His Phe Arg
    50                  55                  60

Gly Arg Val Leu Ile Ser Ala Val Asp Leu Thr Gly Ser Ser Pro Pro
65                  70                  75                  80

Ile Thr Ser Leu Glu Ile Lys Asn Val Thr Ser Asp Asp Thr Ala Val
                85                  90                  95

Tyr Phe Cys Thr Thr Thr Ser Thr Tyr Asp Lys Trp Ser Gly Leu Tyr
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 4
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ile His Leu Val Gln Ser Gly Thr Glu Val Lys Lys Pro Gly Ser
1               5                   10                  15

Ser Val Ala Val Ser Cys Lys Ala Tyr Gly Val Asn Thr Phe Gly Leu
                20                  25                  30

Tyr Ala Val Asn Trp Val Arg Gln Ala Pro Gly Gln Ser Leu Glu Tyr
            35                  40                  45

Ile Gly Gln Ile Trp Arg Trp Lys Ser Ser Ala Ser His Asp Phe Arg
    50                  55                  60

Gly Arg Val Ile Ile Ser Ala Val Asp Leu Thr Gly Ser Ser Pro Pro
65                  70                  75                  80

```
Ile Ser Ser Leu Glu Ile Lys Asn Leu Thr Ser Asp Asp Thr Ala Val
                85                  90                  95

Tyr Phe Cys Thr Ala Thr Ser Thr Pro Asp Tyr Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 5
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Gly Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Val Thr Ser Asp Asp Thr Ala Val
                85                  90                  95

Tyr Phe Cys Thr Thr Thr Ser Thr Tyr Asp Glu Trp Ser Asp Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 6
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95
```

```
Tyr Phe Cys Thr Thr Thr Ser Thr Tyr Asp Lys Trp Ser Gly Leu His
                100                 105                 110

His Asp Gly Val Met Ala Phe Ser Ser Arg Gly Gln Gly Thr Leu Ile
        115                 120                 125

Ser Val Ser Ala Ala Ser Thr Lys Gly
    130                 135

<210> SEQ ID NO 7
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
    50                  55                  60

Gly Arg Val Leu Ile Ser Ala Val Asp Leu Thr Gly Pro Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
                100                 105                 110

His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 8
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
    50                  55                  60

Gly Arg Val Ile Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Ala Ser Thr Tyr Asp Lys Trp Ser Gly Leu His
                100                 105                 110
```

```
His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 9
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Ile Ile Ser Ala Val Asp Leu Thr Gly Ser Ser Pro Pro
65                  70                  75                  80

Ile Ser Pro Leu Glu Ile Lys Asn Leu Thr Ser Asp Thr Ala Val
            85                  90                  95

Tyr Phe Cys Thr Thr Thr Ser Thr Ser Asp Arg Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 10
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Gly Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Val Thr Ser Asp Asp Thr Ala Val
            85                  90                  95

Tyr Phe Cys Thr Thr Thr Ser Thr Tyr Asp Lys Trp Ser Gly Leu His
            100                 105                 110
```

```
His Asp Gly Val Val Ala Phe Ser Ser Trp Gly Gln Gly Thr Leu Ile
        115                 120                 125

Ser Val Ser Ala Ala Ser Thr Lys Gly
    130                 135

<210> SEQ ID NO 11
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Ile His Leu Val Gln Ser Gly Thr Glu Val Lys Lys Pro Gly Ser
1               5                   10                  15

Ser Val Thr Val Ser Cys Lys Ala Tyr Glu Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
    50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Val Thr Ser Asp Thr Ala Val
                85                  90                  95

Tyr Phe Cys Thr Thr Thr Ser Thr His Asp Lys Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 12
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Gly Leu Glu Tyr
        35                  40                  45

Ile Gly Gln Ile Trp Arg Trp Lys Ser Ser Ala Ser His His Phe Arg
    50                  55                  60

Gly Arg Val Leu Ile Ser Ala Ile Asp Leu Thr Gly Ser Ser Pro Pro
65                  70                  75                  80

Ile Ser Ser Leu Glu Ile Lys Asn Val Thr Ser Asp Asp Thr Ala Val
                85                  90                  95

Tyr Phe Cys Thr Thr Met Ser Thr Tyr Asp Lys Trp Ser Gly Leu His
            100                 105                 110
```

His Asp Gly Val Met Ala Phe Ser Ser Trp Gly Gln Gly Thr Leu Ile
            115                 120                 125

Ser Val Ser Ala Ala Ser Thr Lys Gly
        130                 135

<210> SEQ ID NO 13
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Ser Trp Val Arg Gln Ala Pro Gly Gln Arg Leu Glu Tyr
        35                  40                  45

Ile Gly Gln Ile Arg Arg Trp Lys Ser Ser Ala Ser His His Phe Arg
50                  55                  60

Gly Arg Val Thr Val Ser Ala Val Asp Pro Thr Gly Ser Ser Pro Pro
65                  70                  75                  80

Ile Ser Ser Leu Glu Ile Arg Asp Leu Thr Thr Asp Thr Ala Val
                85                  90                  95

Tyr Phe Cys Thr Thr Thr Ser Thr Ser Asp Tyr Trp Ser Gly Leu His
            100                 105                 110

Asn Glu Arg Gly Thr Ala Phe Ser Ser Trp Gly Gln Gly Thr Leu Ile
            115                 120                 125

Ser Val Ser Ala Ala Ser Thr Lys Gly
        130                 135

<210> SEQ ID NO 14
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Gln Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
        130                 135

<210> SEQ ID NO 15
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Ile Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Ser Asp Tyr Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
        130                 135

<210> SEQ ID NO 16
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Arg Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 17
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Ile His Leu Val Gln Ser Gly Thr Glu Val Arg Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 18
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Arg Trp Ser Gly Leu His
            100                 105                 110

His Asp Gly Val Met Ala Phe Ser Ser Trp Gly Gln Gly Thr Leu Ile
            115                 120                 125

Ser Val Ser Ala Ala Ser Thr Lys Gly
        130                 135

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Leu Ala Trp Tyr His Gln Arg Pro Gly Lys Ala Pro Arg Leu Leu
        35                  40                  45

Ile Tyr Arg Gly Ser Arg Leu Leu Gly Gly Val Pro Ser Arg Phe Ser
50                  55                  60

Gly Ser Ala Ala Gly Thr Asp Phe Thr Leu Thr Ile Ala Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
        115

<210> SEQ ID NO 20
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Thr Leu Ser Ala Ser Thr Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Arg
50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
        115

```
<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Arg Leu Leu Gly Gly Val Pro Ser Lys Phe Ser
    50                  55                  60

Gly Ser Ala Ala Gly Thr Asp Phe Thr Leu Thr Ile Ala Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
        115

<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Arg Leu Val Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
        115

<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 23

Asp Ile Gln Met Thr Gln Ser Pro Ser Thr Leu Ser Ala Ser Val Gly
1               5                   10                  15

Asp Thr Val Arg Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Arg Leu Leu Gly Gly Val Pro Ser Arg Phe Ser
50                  55                  60

Gly Ser Ala Ala Gly Ala Asp Phe Thr Leu Thr Ile Ala Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
        115

<210> SEQ ID NO 24
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Pro Ser Thr Leu Ser Ala Ser Ile Gly
1               5                   10                  15

Asp Thr Val Met Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Lys Leu Leu Gly Gly Val Pro Ser Arg Phe Ser
50                  55                  60

Gly Ser Ala Ala Gly Thr Gly Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
        115

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

```
Trp Val Ala Trp Tyr His Gln Arg Pro Gly Lys Ala Pro Arg Leu Leu
            35                  40                  45

Ile Tyr Arg Gly Ala Ala Leu Leu Gly Gly Val Pro Ser Arg Phe Ser
 50                  55                  60

Gly Ser Ala Ala Gly Thr Asp Phe Thr Leu Thr Ile Gly Asn Leu Gln
 65                  70                  75                  80

Ala Glu Asp Phe Gly Thr Phe Tyr Cys Gln Gln Tyr Asp Thr Tyr Pro
                 85                  90                  95

Gly Thr Phe Gly Gln Gly Thr Lys Val Glu Val Lys Arg Thr Val Ala
                100                 105                 110

Ala Pro Ser Val Phe
            115

<210> SEQ ID NO 26
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Thr Leu Ser Ala Ser Val Gly
 1               5                  10                  15

Gly Thr Val Arg Ile Ser Cys Arg Ala Ser Gln Ser Ile Thr Gly Gly
                20                  25                  30

Trp Leu Ala Trp Tyr His Gln Arg Pro Gly Lys Ala Pro Arg Leu Leu
            35                  40                  45

Ile Tyr Arg Gly Ser Arg Leu Leu Gly Gly Val Pro Ser Arg Phe Ser
 50                  55                  60

Gly Ser Ala Ala Gly Thr Asp Phe Thr Leu Thr Ile Ala Asn Leu Gln
 65                  70                  75                  80

Ala Glu Asp Phe Gly Thr Phe Tyr Cys Gln Gln Tyr Asp Thr Tyr Pro
                 85                  90                  95

Gly Thr Phe Gly Gln Gly Thr Lys Val Glu Val Lys Arg Thr Val Ala
                100                 105                 110

Ala Pro Ser Val Phe
            115

<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Thr Leu Ser Ala Ser Val Gly
 1               5                  10                  15

Asp Thr Val Arg Ile Ser Cys Arg Ala Ser Gln Ser Ile Thr Gly Gly
                20                  25                  30

Trp Leu Ala Trp Tyr His Gln Arg Pro Gly Lys Ala Pro Arg Leu Leu
            35                  40                  45

Ile Tyr Arg Gly Ser Arg Leu Leu Gly Gly Val Pro Ser Arg Phe Ser
 50                  55                  60

Gly Ser Ala Ala Gly Thr Gly Phe Thr Leu Thr Ile Ala Asn Leu Gln
 65                  70                  75                  80
```

-continued

Ala Glu Asp Phe Gly Thr Phe Tyr Cys Gln Gln Tyr Asp Thr Tyr Pro
            85                  90                  95

Gly Thr Phe Gly Gln Gly Thr Lys Val Glu Val Lys Arg Thr Val Ala
            100                 105                 110

Ala Pro Ser Val Phe
            115

<210> SEQ ID NO 28
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Gly
            20                  25                  30

Trp Val Ala Trp Tyr His Gln Arg Pro Gly Lys Ala Pro Arg Leu Leu
        35                  40                  45

Ile Tyr Arg Gly Ser Arg Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
            115

<210> SEQ ID NO 29
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
            115

```
<210> SEQ ID NO 30
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Thr Leu Ser Ala Ser Val Gly
1               5                   10                  15

Asp Thr Val Arg Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Arg Leu Leu Gly Gly Val Pro Ser Arg Phe Ser
    50                  55                  60

Gly Ser Ala Ala Gly Thr Asp Phe Thr Leu Thr Ile Ala Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
        115

<210> SEQ ID NO 31
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Arg
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
        115

<210> SEQ ID NO 32
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 32

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Thr Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
            115

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Arg Leu Leu Gly Gly Val Pro Ser Arg Phe Ser
    50                  55                  60

Gly Ser Ala Ala Gly Thr Asp Phe Thr Leu Thr Ile Ala Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe
            115

<210> SEQ ID NO 34
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
            35                  40                  45

Ile Gly Gln Ile Trp Arg Trp Lys Ser Ser Ala Ser His His Phe Arg
 50                  55                  60

Gly Arg Val Leu Ile Ser Ala Val Asp Leu Thr Gly Ser Ser Pro Pro
 65                  70                  75                  80

Ile Ser Ser Leu Glu Ile Lys Asn Leu Thr Ser Asp Asp Thr Ala Val
                 85                  90                  95

Tyr Phe Cys Thr Thr Thr Ser Thr Tyr Asp Lys Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala
        130

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Met Thr Gln Ser Pro Ser Thr Leu Ser Ala Ser Ile Gly
 1               5                  10                  15

Asp Thr Val Arg Ile Ser Cys Arg Ala Ser Gln Ser Ile Thr Gly Asn
                 20                  25                  30

Trp Val Ala Trp Tyr Gln Gln Arg Pro Gly Lys Ala Pro Arg Leu Leu
            35                  40                  45

Ile Tyr Arg Gly Ala Ala Leu Leu Gly Gly Val Pro Ser Arg Phe Ser
 50                  55                  60

Gly Ser Ala Ala Gly Thr Asp Phe Thr Leu Thr Ile Gly Asn Leu Gln
 65                  70                  75                  80

Ala Glu Asp Phe Gly Thr Phe Tyr Cys Gln Gln Tyr Asp Thr Tyr Pro
                 85                  90                  95

Gly Thr Phe Gly Gln Gly Thr Lys Val Glu Val
            100                 105

<210> SEQ ID NO 36
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Thr Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Thr

<210> SEQ ID NO 37
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Pro Ile
                85                  90                  95

Thr Phe Gly Gln Gly Thr Arg Leu Glu Ile
            100                 105

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Ser Thr Tyr Asp Lys Trp Ser Gly Leu His His Asp Gly Val Met
1               5                   10                  15

Ala Phe Ser Ser
            20

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Ser Thr Tyr Asp Gln Trp Ser Gly Leu His His Asp Gly Val Met
1               5                   10                  15

Ala Phe Ser Ser
            20

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 40

Thr Ser Thr Ser Asp Tyr Trp Ser Gly Leu His His Asp Gly Val Met
1               5                   10                  15

Ala Phe Ser Ser
            20

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Ser Thr Tyr Asp Arg Trp Ser Gly Leu His His Asp Gly Val Met
1               5                   10                  15

Ala Phe Ser Ser
            20

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Ser Thr Tyr Asp Lys Trp Ser Gly Leu His His Asp Gly Val Met
1               5                   10                  15

Ala Phe Ser Ser
            20

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Ser Thr Tyr Asp Arg Trp Ser Gly Leu His His Asp Gly Val Met
1               5                   10                  15

Ala Phe Ser Ser
            20

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gln Tyr Asp Thr Tyr Pro Gly Thr
1               5

<210> SEQ ID NO 45
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 45

Gln Gln Tyr Asp Thr Tyr Pro Gly Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Tyr Asp Thr Tyr Pro Gly Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Tyr Asp Thr Tyr Pro Gly Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Tyr Asp Thr Tyr Pro Gly Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Gln Tyr Asp Thr Tyr Pro Gly Thr
1               5

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ggtgtacatt ctcagataca cctcgtacaa                                         30
```

```
<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
caggtgtcca gtctcagata ca                                              22

<210> SEQ ID NO 52
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gacatccaga tgacccagtc tccttccacc ctgtctgcat ctataggt                  48

<210> SEQ ID NO 53
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gacatccaga tgacccagtc tccttccacc ctgtctgcat ct                        42

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cgcctctgcc tctactccca a                                               21

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
caaagtggag ttgaaatcag ggaa                                            24

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
caaagtggag ttgaaatcag ggaaccggct tccag                                35
```

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcggagacgg agatgagggt t                                             21

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gtttcacctc aactttagtc cctt                                          24

<210> SEQ ID NO 59
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtttcacctc aactttagtc ccttggccga aggtc                              35

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 60

His His His His His His
1               5

<210> SEQ ID NO 61
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg

<210> SEQ ID NO 62
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser
        115                 120

<210> SEQ ID NO 63
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser
        115                 120
```

```
<210> SEQ ID NO 64
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
                20                  25                  30

Tyr Ala Val Asn Trp Val Arg Gln Ala Pro Gly Gln Ser Leu Glu Tyr
            35                  40                  45

Ile Gly Gln Ile Trp Arg Trp Lys Ser Ser Ala Ser His His Phe Arg
    50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser
        115                 120

<210> SEQ ID NO 65
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
                20                  25                  30

Tyr Ala Val Asn Trp Val Arg Gln Ala Pro Gly Gln Ser Leu Glu Tyr
            35                  40                  45

Ile Gly Gln Ile Trp Arg Trp Lys Ser Ser Ala Ser His His Phe Arg
    50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser
        115                 120

<210> SEQ ID NO 66
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 66

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Gln Trp Ser Gly Leu His
            100                 105                 110

His Asp Gly Val Met Ala Phe Ser Ser
        115                 120

<210> SEQ ID NO 67
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Gln Trp Ser Gly Leu His
            100                 105                 110

His Asp Gly Val Met Ala Phe Ser Ser
        115                 120

<210> SEQ ID NO 68
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30
```

-continued

Tyr Ala Val Asn Trp Val Arg Gln Ala Pro Gly Gln Ser Leu Glu Tyr
           35                  40                  45

Ile Gly Gln Ile Trp Arg Trp Lys Ser Ser Ala Ser His His Phe Arg
 50                  55                  60

Gly Arg Val Leu Ile Ser Ala Val Asp Leu Thr Gly Ser Ser Pro Pro
 65                  70                  75                  80

Ile Ser Ser Leu Glu Ile Lys Asn Leu Thr Ser Asp Asp Thr Ala Val
               85                  90                  95

Tyr Phe Cys Thr Thr Thr Ser Thr Tyr Asp Arg Trp Ser Gly Leu His
               100                 105                 110

His Asp Gly Val Met Ala Phe Ser Ser
           115                 120

<210> SEQ ID NO 69
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Ile His Leu Val Gln Ser Gly Thr Glu Val Lys Lys Pro Gly Ser
 1               5                  10                  15

Ser Val Thr Val Ser Cys Lys Ala Tyr Gly Val Asn Thr Phe Gly Leu
                20                  25                  30

Tyr Ala Val Asn Trp Val Arg Gln Ala Pro Gly Gln Ser Leu Glu Tyr
           35                  40                  45

Ile Gly Gln Ile Trp Arg Trp Lys Ser Ser Ala Ser His His Phe Arg
 50                  55                  60

Gly Arg Val Ile Ile Ser Ala Val Asp Leu Thr Gly Ser Ser Pro Pro
 65                  70                  75                  80

Ile Ser Ser Leu Glu Ile Lys Asn Leu Thr Ser Asp Asp Thr Ala Val
               85                  90                  95

Tyr Phe Cys Thr Thr Thr Ser Thr Ser Asp Tyr Trp Ser Gly Leu His
               100                 105                 110

His Asp Gly Val Met Ala Phe Ser Ser
           115                 120

<210> SEQ ID NO 70
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Ile His Leu Val Gln Ser Gly Thr Glu Val Lys Lys Pro Gly Ser
 1               5                  10                  15

Ser Val Thr Val Ser Cys Lys Ala Tyr Gly Val Asn Thr Phe Gly Leu
                20                  25                  30

Tyr Ala Val Asn Trp Val Arg Gln Ala Pro Gly Gln Ser Leu Glu Tyr
           35                  40                  45

Ile Gly Gln Ile Trp Arg Trp Lys Ser Ser Ala Ser His His Phe Arg
 50                  55                  60

Gly Arg Val Leu Ile Ser Ala Val Asp Leu Thr Gly Ser Ser Pro Pro
 65                  70                  75                  80

```
Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Arg Trp Ser Gly Leu His
            100                 105                 110

His Asp Gly Val Met Ala Phe Ser Ser
        115                 120

<210> SEQ ID NO 71
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Ile His Leu Val Gln Ser Gly Thr Glu Val Arg Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
    50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser
        115                 120

<210> SEQ ID NO 72
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His Pro Phe Arg
    50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser
        115                 120
```

```
<210> SEQ ID NO 73
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 74
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly
            100

<210> SEQ ID NO 75
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45
```

```
Ile Tyr Arg Gly Ala Ala Leu Leu Gly Gly Val Pro Ser Arg Phe Ser
 50                  55                  60

Gly Ser Ala Ala Gly Thr Asp Phe Thr Leu Thr Ile Gly Asn Leu Gln
 65                  70                  75                  80

Ala Glu Asp Phe Gly Thr Phe Tyr Cys Gln Gln Tyr Asp Thr Tyr Pro
                 85                  90                  95

Gly Thr Phe Gly
            100

<210> SEQ ID NO 76
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
 50                  55                  60

Gly Ser Ala Ala Gly Thr Asp Phe Thr Leu Thr Ile Gly Asn Leu Gln
 65                  70                  75                  80

Ala Glu Asp Phe Gly Thr Phe Tyr Cys Gln Gln Tyr Asp Thr Tyr Pro
                 85                  90                  95

Gly Thr Phe Gly
            100

<210> SEQ ID NO 77
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
 50                  55                  60

Gly Ser Ala Ala Gly Thr Asp Phe Thr Leu Thr Ile Gly Asn Leu Gln
 65                  70                  75                  80

Ala Glu Asp Phe Gly Thr Phe Tyr Cys Gln Gln Tyr Asp Thr Tyr Pro
                 85                  90                  95

Gly Thr Phe Gly
            100
```

```
<210> SEQ ID NO 78
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78
```

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly
            100

```
<210> SEQ ID NO 79
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79
```

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly
            100

```
<210> SEQ ID NO 80
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80
```

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
 35                  40                  45

Ile Tyr Arg Gly Ser Arg Leu Leu Gly Gly Val Pro Ser Arg Phe Ser
 50                  55                  60

Gly Ser Ala Ala Gly Thr Asp Phe Thr Leu Thr Ile Ala Asn Leu Gln
 65                  70                  75                  80

Ala Glu Asp Phe Gly Thr Phe Tyr Cys Gln Gln Tyr Asp Thr Tyr Pro
                 85                  90                  95

Gly Thr Phe Gly
            100

<210> SEQ ID NO 81
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Gln Met Thr Gln Ser Pro Ser Thr Leu Ser Ala Ser Val Gly
1                5                  10                  15

Asp Thr Val Arg Ile Ser Cys Arg Ala Ser Gln Ser Ile Thr Gly Gly
                 20                  25                  30

Trp Leu Ala Trp Tyr His Gln Arg Pro Gly Lys Ala Pro Arg Leu Leu
 35                  40                  45

Ile Tyr Arg Gly Ser Arg Leu Leu Gly Gly Val Pro Ser Arg Phe Ser
 50                  55                  60

Gly Ser Ala Ala Gly Thr Asp Phe Thr Leu Thr Ile Ala Asn Leu Gln
 65                  70                  75                  80

Ala Glu Asp Phe Gly Thr Phe Tyr Cys Gln Gln Tyr Asp Thr Tyr Pro
                 85                  90                  95

Gly Thr Phe Gly
            100

<210> SEQ ID NO 82
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Ser Thr Leu Ser Ala Ser Ile Gly
1                5                  10                  15

Asp Thr Val Arg Ile Ser Cys Arg Ala Ser Gln Ser Ile Thr Gly Asn
                 20                  25                  30

Trp Val Ala Trp Tyr Gln Gln Arg Pro Gly Lys Ala Pro Arg Leu Leu
 35                  40                  45

Ile Tyr Arg Gly Ala Ala Leu Leu Gly Gly Val Pro Ser Arg Phe Arg
 50                  55                  60

Gly Ser Ala Ala Gly Thr Asp Phe Thr Leu Thr Ile Gly Asn Leu Gln
 65                  70                  75                  80

Ala Glu Asp Phe Gly Thr Phe Tyr Cys Gln Gln Tyr Asp Thr Tyr Pro
                 85                  90                  95

Gly Thr Phe Gly
            100

```
<210> SEQ ID NO 83
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83
```

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Thr Glu Asp Phe Gly Thr Phe Tyr Cys Gln Gln Tyr Asp Thr Tyr Pro
                85                  90                  95

Gly Thr Phe Gly
            100

```
<210> SEQ ID NO 84
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84
```

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly
            100

```
<210> SEQ ID NO 85
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
```
caggtgccca gtctcagata cacctcgtac aa                          32

<210> SEQ ID NO 86
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gacatccaga tgacccagtc tccttccacc ctggctgcat ctataggt            48

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ccggcgcctc tgcctctact cccaa                                     25

<210> SEQ ID NO 88
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
caaagtggag ttgaaatcag ggaaccggct tccagggacc                     40

<210> SEQ ID NO 89
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ala Ser His His Phe Arg
    50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser Trp Gly Gln
        115                 120

<210> SEQ ID NO 90
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Ser Trp Val Arg Gln Ala Pro Gly Gln Arg Leu Glu Tyr
        35                  40                  45

Ile Gly Gln Ile Arg Arg Trp Lys Ser Ser Ala Ser His His Phe Arg
50                  55                  60

Gly Arg Val Thr Val Ser Ala Val Asp Pro Thr Gly Ser Ser Pro Pro
65                  70                  75                  80

Ile Ser Ser Leu Glu Ile Arg Asp Leu Thr Thr Asp Asp Thr Ala Val
                85                  90                  95

Tyr Phe Cys Thr Thr Thr Ser Thr Ser Asp Tyr Trp Ser Gly Leu His
            100                 105                 110

Asn Glu Arg Gly Thr Ala Phe Ser Ser Trp Gly Gln
            115                 120

<210> SEQ ID NO 91
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Ile Ile Ser Ala Val Asp Leu Thr Gly Ser Ser Pro Pro
65                  70                  75                  80

Ile Ser Pro Leu Glu Ile Lys Asn Leu Thr Ser Asp Asp Thr Ala Val
                85                  90                  95

Tyr Phe Cys Thr Thr Thr Ser Thr Ser Asp Arg Trp Ser Gly Leu His
            100                 105                 110

His Asp Gly Val Met Ala Phe Ser Ser Trp Gly Gln
            115                 120

<210> SEQ ID NO 92
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Ile His Leu Val Gln Ser Gly Thr Gly Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Gly Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Thr Ser Leu Glu Ile Lys Asn Val Thr Ser Asp Asp Thr Ala Val
                85                  90                  95

Tyr Phe Cys Thr Thr Thr Ser Thr Tyr Asp Lys Trp Ser Gly Leu Tyr
            100                 105                 110

His Asp Gly Val Met Ala Phe Ser Ser Trp Gly Gln
        115                 120

<210> SEQ ID NO 93
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Ile Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Ala Ser Thr Tyr Asp Lys Trp Ser Gly Leu His
            100                 105                 110

His Asp Gly Val Met Ala Phe Ser Ser Trp Gly Gln
        115                 120

<210> SEQ ID NO 94
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Ile His Leu Val Gln Ser Gly Thr Glu Val Lys Lys Pro Gly Ser
1               5                   10                  15

Ser Val Ala Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
            35                  40                  45

Ile Gly Gln Ile Trp Arg Trp Lys Ser Ser Ala Ser His Asp Phe Arg
 50                  55                  60

Gly Arg Val Ile Ile Ser Ala Val Asp Leu Thr Gly Ser Ser Pro Pro
 65                  70                  75                  80

Ile Ser Ser Leu Glu Ile Lys Asn Leu Thr Ser Asp Asp Thr Ala Val
                85                  90                  95

Tyr Phe Cys Thr Ala Thr Ser Thr Pro Asp Tyr Trp Ser Gly Leu His
                100                 105                 110

His Asp Gly Val Met Ala Phe Ser Ser Trp Gly Gln
            115                 120

<210> SEQ ID NO 95
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Ile His Leu Val Gln Ser Gly Thr Glu Val Lys Lys Pro Gly Ser
 1               5                  10                  15

Ser Val Thr Val Ser Cys Lys Ala Tyr Gly Val Asn Thr Phe Gly Leu
                20                  25                  30

Tyr Ala Val Asn Trp Val Arg Gln Ala Pro Gly Gln Ser Leu Glu Tyr
            35                  40                  45

Ile Gly Gln Ile Trp Arg Trp Lys Ser Ser Ala Ser His His Phe Arg
 50                  55                  60

Gly Arg Val Leu Ile Ser Ala Val Asp Leu Thr Gly Pro Ser Pro Pro
 65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
                100                 105                 110

His Asp Gly Val Met Ala Phe Ser Ser Trp Gly Gln
            115                 120

<210> SEQ ID NO 96
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Ile His Leu Val Gln Ser Gly Thr Glu Val Lys Lys Pro Gly Ser
 1               5                  10                  15

Ser Val Thr Val Ser Cys Lys Ala Tyr Gly Val Asn Thr Phe Gly Leu
                20                  25                  30

Tyr Ala Val Asn Trp Val Arg Gln Ala Pro Gly Gln Ser Leu Glu Tyr
            35                  40                  45

Ile Gly Gln Ile Trp Arg Trp Lys Ser Ser Ala Ser His His Phe Arg
 50                  55                  60

Gly Arg Val Ile Ile Ser Ala Val Asp Leu Thr Gly Ser Ser Pro Pro
 65                  70                  75                  80

```
Ile Ser Ser Leu Glu Ile Lys Asn Leu Thr Ser Asp Asp Thr Ala Val
                85                  90                  95

Tyr Phe Cys Thr Thr Thr Ser Thr Ser Asp Tyr Trp Ser Gly Leu His
            100                 105                 110

His Asp Gly Val Met Ala Phe Ser Ser Trp Gly Gln
        115                 120

<210> SEQ ID NO 97
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Ile His Leu Val Gln Ser Gly Thr Glu Val Lys Lys Pro Gly Ser
1               5                   10                  15

Ser Val Thr Val Ser Cys Lys Ala Tyr Glu Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Val Thr Ser Asp Asp Thr Ala Val
                85                  90                  95

Tyr Phe Cys Thr Thr Thr Ser Thr His Asp Lys Trp Ser Gly Leu His
            100                 105                 110

His Asp Gly Val Met Ala Phe Ser Ser Trp Gly Gln
        115                 120

<210> SEQ ID NO 98
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Gly Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Val Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Val Ala Phe Ser Ser Trp Gly Gln
        115                 120
```

<210> SEQ ID NO 99
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Gly Leu Glu Tyr
        35                  40                  45

Ile Gly Gln Ile Trp Arg Trp Lys Ser Ser Ala Ser His His Phe Arg
    50                  55                  60

Gly Arg Val Leu Ile Ser Ala Ile Asp Leu Thr Gly Ser Ser Pro Pro
65                  70                  75                  80

Ile Ser Ser Leu Glu Ile Lys Asn Val Thr Ser Asp Asp Thr Ala Val
                85                  90                  95

Tyr Phe Cys Thr Thr Met Ser Thr Tyr Asp Lys Trp Ser Gly Leu His
            100                 105                 110

His Asp Gly Val Met Ala Phe Ser Ser Trp Gly Gln
        115                 120
```

<210> SEQ ID NO 100
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
    50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Arg Trp Ser Gly Leu His
            100                 105                 110

His Asp Gly Val Met Ala Phe Ser Ser Trp Gly Gln
        115                 120
```

<210> SEQ ID NO 101
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Gly Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Val Thr Ser Asp Asp Thr Ala Val
                85                  90                  95

Tyr Phe Cys Thr Thr Thr Ser Thr Tyr Asp Glu Trp Ser Asp Leu His
            100                 105                 110

His Asp Gly Val Met Ala Phe Ser Ser Trp Gly Gln
        115                 120

<210> SEQ ID NO 102
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser Arg Gly Gln
        115                 120

<210> SEQ ID NO 103
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

```
Leu Ala Trp Tyr Gln Gln Lys Pro Gly Lys Ala Pro Lys Leu Leu Ile
             35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Pro
                 85                  90                  95

<210> SEQ ID NO 104
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Gln Met Thr Gln Ser Pro Ser Thr Leu Ser Ala Ser Ile Gly
 1               5                  10                  15

Asp Thr Val Arg Ile Ser Cys Arg Ala Ser Gln Ser Ile Thr Gly Asn
                20                  25                  30

Trp Val Ala Trp Tyr Gln Gln Arg Pro Gly Lys Ala Pro Arg Leu Leu
             35                  40                  45

Ile Tyr Arg Gly Ala Ala Leu Leu Gly Val Pro Ser Arg Phe Ser
 50                  55                  60

Gly Ser Ala Ala Gly Thr Asp Phe Thr Leu Thr Ile Gly Asn Leu Gln
 65                  70                  75                  80

Ala Glu Asp Phe Gly Thr Phe Tyr Cys Gln Gln Tyr Asp Thr Tyr Pro
                 85                  90                  95

Gly Thr Phe

<210> SEQ ID NO 105
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Asp Ile Gln Met Thr Gln Ser Pro Ser Thr Leu Ser Ala Ser Ile Gly
 1               5                  10                  15

Asp Thr Val Arg Ile Ser Cys Arg Ala Ser Gln Ser Ile Thr Gly Asn
                20                  25                  30

Trp Leu Ala Trp Tyr His Gln Arg Pro Gly Lys Ala Pro Arg Leu Leu
             35                  40                  45

Ile Tyr Arg Gly Ser Arg Leu Leu Gly Gly Val Pro Ser Arg Phe Ser
 50                  55                  60

Gly Ser Ala Ala Gly Thr Asp Phe Thr Leu Thr Ile Ala Asn Leu Gln
 65                  70                  75                  80

Ala Glu Asp Phe Gly Thr Phe Tyr Cys Gln Gln Tyr Asp Thr Tyr Pro
                 85                  90                  95

Gly Thr Phe

<210> SEQ ID NO 106
<211> LENGTH: 99
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 106

```
Asp Ile Gln Met Thr Gln Ser Pro Ser Thr Leu Ser Ala Ser Thr Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Arg Pro Gly Lys Ala Pro Arg Leu Leu
        35                  40                  45

Ile Tyr Arg Gly Ala Ala Leu Leu Gly Gly Val Pro Ser Arg Phe Arg
50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe
```

<210> SEQ ID NO 107
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Asp Ile Gln Met Thr Gln Ser Pro Ser Thr Leu Ser Ala Ser Val Gly
1               5                   10                  15

Gly Thr Val Arg Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Arg Leu Leu Gly Gly Val Pro Ser Arg Phe Ser
50                  55                  60

Gly Ser Ala Ala Gly Thr Asp Phe Thr Leu Thr Ile Ala Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe
```

<210> SEQ ID NO 108
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Asp Ile Gln Met Thr Gln Ser Pro Ser Thr Leu Ser Ala Ser Val Gly
1               5                   10                  15

Asp Thr Val Arg Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Arg Leu Leu Gly Gly Val Pro Ser Arg Phe Ser
50                  55                  60
```

Gly Ser Ala Ala Gly Ala Asp Phe Thr Leu Thr Ile Ala Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe

<210> SEQ ID NO 109
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asp Ile Gln Met Thr Gln Ser Pro Ser Thr Leu Ser Ala Ser Val Gly
1               5                   10                  15

Asp Thr Val Arg Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Arg Leu Leu Gly Gly Val Pro Ser Arg Phe Ser
    50                  55                  60

Gly Ser Ala Ala Gly Thr Gly Phe Thr Leu Thr Ile Ala Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe

<210> SEQ ID NO 110
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Gln Met Thr Gln Ser Pro Ser Thr Leu Ser Ala Ser Ile Gly
1               5                   10                  15

Asp Thr Val Met Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Lys Leu Leu Gly Gly Val Pro Ser Arg Phe Ser
    50                  55                  60

Gly Ser Ala Ala Gly Thr Gly Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe

<210> SEQ ID NO 111
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 111

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Arg Leu Leu Gly Gly Val Pro Ser Lys Phe Ser
    50                  55                  60

Gly Ser Ala Ala Gly Thr Asp Phe Thr Leu Thr Ile Ala Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe

<210> SEQ ID NO 112
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr His Gln Arg Pro Gly Lys Ala Pro Arg Leu Leu
        35                  40                  45

Ile Tyr Arg Gly Ala Ala Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe

<210> SEQ ID NO 113
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Gly
            20                  25                  30

Trp Leu Ala Trp Tyr His Gln Arg Pro Gly Lys Ala Pro Arg Leu Leu
        35                  40                  45

Ile Tyr Arg Gly Ser Arg Leu Val Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80
```

```
Ala Glu Asp Phe Gly Thr Phe Tyr Cys Gln Gln Tyr Asp Thr Tyr Pro
                85                  90                  95

Gly Thr Phe

<210> SEQ ID NO 114
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Gly
            20                  25                  30

Trp Val Ala Trp Tyr His Gln Arg Pro Gly Lys Ala Pro Arg Leu Leu
        35                  40                  45

Ile Tyr Arg Gly Ser Arg Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln Ser Ile Thr Gly Asn Trp
1               5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Gln Tyr Asp Thr Tyr Pro Gly
1               5

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Ser Ile Ser Ser Trp
1               5
```

```
<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Gln Tyr Asn Thr Tyr Pro Ile
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Gln Ala Ala Ala Ala Pro Gly
1               5

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Ser Ile Ser Ser Trp
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Gln Tyr Asn Thr Tyr Pro Ile
1               5

<210> SEQ ID NO 122
<211> LENGTH: 685
<212> TYPE: PRT
<213> ORGANISM: Human immunodeficiency virus

<400> SEQUENCE: 122

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80
```

```
Pro Gln Glu Val Val Leu Val Asn Val Thr Glu Asn Phe Asn Met Trp
             85                  90                  95
Lys Asn Asp Met Val Glu Gln Met His Glu Asp Ile Ile Ser Leu Trp
            100                 105                 110
Asp Gln Ser Leu Lys Pro Cys Val Lys Leu Thr Pro Leu Cys Val Ser
            115                 120                 125
Leu Lys Cys Thr Asp Leu Lys Asn Asp Thr Asn Thr Asn Ser Ser Ser
130                 135                 140
Gly Arg Met Ile Met Glu Lys Gly Glu Ile Lys Asn Cys Ser Phe Asn
145                 150                 155                 160
Ile Ser Thr Ser Ile Arg Gly Lys Val Gln Lys Glu Tyr Ala Phe Phe
                165                 170                 175
Tyr Lys Leu Asp Ile Ile Pro Ile Asp Asn Asp Thr Thr Ser Tyr Lys
            180                 185                 190
Leu Thr Ser Cys Asn Thr Ser Val Ile Thr Gln Ala Cys Pro Lys Val
            195                 200                 205
Ser Phe Glu Pro Ile Pro Ile His Tyr Cys Ala Pro Ala Gly Phe Ala
210                 215                 220
Ile Leu Lys Cys Asn Asn Lys Thr Phe Asn Gly Thr Gly Pro Cys Thr
225                 230                 235                 240
Asn Val Ser Thr Val Gln Cys Thr His Gly Ile Arg Pro Val Val Ser
                245                 250                 255
Thr Gln Leu Leu Leu Asn Gly Ser Leu Ala Glu Glu Val Val Ile
            260                 265                 270
Arg Ser Val Asn Phe Thr Asp Asn Ala Lys Thr Ile Ile Val Gln Leu
            275                 280                 285
Asn Thr Ser Val Glu Ile Asn Cys Thr Arg Pro Asn Asn Asn Thr Arg
            290                 295                 300
Lys Arg Ile Arg Ile Gln Arg Gly Pro Gly Arg Ala Phe Val Thr Ile
305                 310                 315                 320
Gly Lys Ile Gly Asn Met Arg Gln Ala His Cys Asn Ile Ser Arg Ala
                325                 330                 335
Lys Trp Asn Asn Thr Leu Lys Gln Ile Ala Ser Lys Leu Arg Glu Gln
            340                 345                 350
Phe Gly Asn Asn Lys Thr Ile Ile Phe Lys Gln Ser Ser Gly Gly Asp
            355                 360                 365
Pro Glu Ile Val Thr His Ser Phe Asn Cys Gly Gly Glu Phe Phe Tyr
            370                 375                 380
Cys Asn Ser Thr Gln Leu Phe Asn Ser Thr Trp Phe Asn Ser Thr Trp
385                 390                 395                 400
Ser Thr Glu Gly Ser Asn Asn Thr Glu Gly Ser Asp Thr Ile Thr Leu
                405                 410                 415
Pro Cys Arg Ile Lys Gln Ile Ile Asn Met Trp Gln Lys Val Gly
            420                 425                 430
Lys Ala Met Tyr Ala Pro Pro Ile Ser Gly Gln Ile Arg Cys Ser Ser
            435                 440                 445
Asn Ile Thr Gly Leu Leu Leu Thr Arg Asp Gly Gly Asn Ser Asn Asn
            450                 455                 460
Glu Ser Glu Ile Phe Arg Pro Gly Gly Gly Asp Met Arg Asp Asn Trp
465                 470                 475                 480
Arg Ser Glu Leu Tyr Lys Tyr Lys Val Val Lys Ile Glu Pro Leu Gly
                485                 490                 495
```

```
Val Ala Pro Thr Lys Ala Lys Arg Arg Val Val Gln Arg Glu Lys Arg
            500                 505                 510

Ala Val Gly Ile Gly Ala Leu Phe Leu Gly Phe Leu Gly Ala Ala Gly
            515                 520                 525

Ser Thr Met Gly Ala Ala Ser Met Thr Leu Thr Val Gln Ala Arg Gln
            530                 535                 540

Leu Leu Ser Gly Ile Val Gln Gln Gln Asn Asn Leu Leu Arg Ala Ile
545                 550                 555                 560

Glu Ala Gln Gln His Leu Leu Gln Leu Thr Val Trp Gly Ile Lys Gln
                565                 570                 575

Leu Gln Ala Arg Ile Leu Ala Val Glu Arg Tyr Leu Lys Asp Gln Gln
            580                 585                 590

Leu Leu Gly Ile Trp Gly Cys Ser Gly Lys Leu Ile Cys Thr Thr Ala
            595                 600                 605

Val Pro Trp Asn Ala Ser Trp Ser Asn Lys Ser Leu Glu Gln Ile Trp
            610                 615                 620

Asn His Thr Thr Trp Met Glu Trp Asp Arg Glu Ile Asn Asn Tyr Thr
625                 630                 635                 640

Ser Leu Ile His Ser Leu Ile Glu Glu Ser Gln Asn Gln Gln Glu Lys
                645                 650                 655

Asn Glu Gln Glu Leu Leu Glu Leu Asp Lys Trp Ala Ser Leu Trp Asn
            660                 665                 670

Trp Phe Asn Ile Thr Asn Trp Leu Trp Tyr Ile Lys Leu
            675                 680                 685

<210> SEQ ID NO 123
<211> LENGTH: 679
<212> TYPE: PRT
<213> ORGANISM: Human immunodeficiency virus

<400> SEQUENCE: 123

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
            20                  25                  30

Leu Trp Val Thr Val Tyr Tyr Gly Val Pro Val Trp Lys Asp Ala Asp
        35                  40                  45

Thr Thr Leu Phe Cys Ala Ser Asp Ala Lys Ala His Glu Thr Glu Val
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Asn Phe Asn Met Trp Lys
                85                  90                  95

Asn Asn Met Val Glu Gln Met Gln Glu Asp Val Ile Ser Leu Trp Asp
            100                 105                 110

Gln Ser Leu Gln Pro Cys Val Lys Leu Thr Pro Leu Cys Val Thr Leu
        115                 120                 125

His Cys Thr Thr Ala Lys Leu Thr Asn Val Thr Asn Ile Thr Asn Val
    130                 135                 140

Pro Asn Ile Gly Asn Ile Thr Asp Glu Val Arg Asn Cys Ser Phe Asn
145                 150                 155                 160

Met Thr Thr Glu Ile Arg Asp Lys Lys Gln Lys Val His Ala Leu Phe
                165                 170                 175

Tyr Lys Leu Asp Ile Val Gln Ile Glu Asp Lys Asn Asp Ser Ser Lys
            180                 185                 190
```

```
Tyr Arg Leu Ile Asn Cys Asn Thr Ser Val Ile Lys Gln Ala Cys Pro
            195                 200                 205

Lys Ile Ser Phe Asp Pro Ile Pro Ile His Tyr Cys Thr Pro Ala Gly
    210                 215                 220

Tyr Val Ile Leu Lys Cys Asn Asp Lys Asn Phe Asn Gly Thr Gly Pro
225                 230                 235                 240

Cys Lys Asn Val Ser Ser Val Gln Cys Thr His Gly Ile Lys Pro Val
                245                 250                 255

Val Ser Thr Gln Leu Leu Leu Asn Gly Ser Leu Ala Glu Glu Glu Ile
            260                 265                 270

Ile Ile Arg Ser Glu Asn Leu Thr Asn Asn Ala Lys Thr Ile Ile Val
        275                 280                 285

His Leu Asn Lys Ser Val Glu Ile Asn Cys Thr Arg Pro Ser Asn Asn
    290                 295                 300

Met Arg Thr Ser Met Arg Ile Gly Pro Gly Gln Val Phe Tyr Arg Thr
305                 310                 315                 320

Gly Ser Ile Thr Gly Asp Ile Arg Lys Ala Tyr Cys Glu Ile Asn Gly
                325                 330                 335

Thr Lys Trp Asn Lys Val Leu Lys Gln Val Thr Glu Lys Leu Lys Glu
            340                 345                 350

His Phe Asn Asn Lys Thr Ile Ile Phe Gln Pro Pro Ser Gly Gly Asp
        355                 360                 365

Leu Glu Ile Thr Met His His Phe Asn Cys Arg Gly Glu Phe Phe Tyr
    370                 375                 380

Cys Asn Thr Thr Gln Leu Phe Asn Asn Thr Cys Ile Gly Asn Glu Thr
385                 390                 395                 400

Met Lys Gly Cys Asn Gly Thr Ile Thr Leu Pro Cys Lys Ile Lys Gln
                405                 410                 415

Ile Ile Ile Asn Met Trp Gln Gly Thr Gly Gln Ala Met Tyr Ala Pro
            420                 425                 430

Pro Ile Asp Gly Lys Ile Asn Cys Val Ser Asn Ile Thr Gly Ile Leu
        435                 440                 445

Leu Thr Arg Asp Gly Gly Ala Asn Asn Thr Ser Asn Glu Thr Phe Arg
    450                 455                 460

Pro Gly Gly Gly Asn Ile Lys Asp Asn Trp Arg Ser Glu Leu Tyr Lys
465                 470                 475                 480

Tyr Lys Val Val Gln Ile Glu Pro Leu Gly Ile Ala Pro Thr Arg Ala
                485                 490                 495

Lys Arg Arg Val Val Glu Arg Glu Lys Arg Ala Val Gly Ile Gly Ala
            500                 505                 510

Met Ile Phe Gly Phe Leu Gly Ala Ala Gly Ser Thr Met Gly Ala Ala
        515                 520                 525

Ser Ile Thr Leu Thr Val Gln Ala Arg Gln Leu Leu Ser Gly Ile Val
    530                 535                 540

Gln Gln Gln Ser Asn Leu Leu Arg Ala Ile Glu Ala Gln Gln His Leu
545                 550                 555                 560

Leu Gln Leu Thr Val Trp Gly Ile Lys Gln Leu Gln Ala Arg Val Leu
                565                 570                 575

Ala Val Glu Arg Tyr Leu Lys Asp Gln Lys Phe Leu Gly Leu Trp Gly
            580                 585                 590

Cys Ser Gly Lys Ile Ile Cys Thr Thr Ala Val Pro Trp Asn Ser Thr
        595                 600                 605
```

-continued

```
Trp Ser Asn Lys Ser Phe Glu Glu Ile Trp Asn Asn Met Thr Trp Ile
    610             615                 620
Glu Trp Glu Arg Glu Ile Ser Asn Tyr Thr Asn Gln Ile Tyr Glu Ile
625             630                 635             640
Leu Thr Glu Ser Gln Asn Gln Gln Asp Arg Asn Glu Lys Asp Leu Leu
            645                 650                 655
Glu Leu Asp Lys Trp Ala Ser Leu Trp Asn Trp Phe Asp Ile Thr Asn
            660             665                 670
Trp Leu Trp Tyr Ile Lys Ile
        675
```